United States Patent
El Andaloussi et al.

(10) Patent No.: US 11,649,272 B2
(45) Date of Patent: May 16, 2023

(54) THERAPEUTIC DELIVERY VESICLES

(71) Applicant: Evox Therapeutics Ltd., Oxford (GB)

(72) Inventors: Samir El Andaloussi, Huddinge (SE); Oscar Wiklander, Solna (SE); Joel Nordin, Stockholm (SE); Edvard Smith, Stockholm (SE); Karl-Henrik Grinnemo, Hägersten (SE); Oscar Simonson, Stockholm (SE)

(73) Assignee: Evox Therapeutics Ltd., Oxford (GB)

(*) Notice: Subject to any disclaimer, the term of this patent is extended or adjusted under 35 U.S.C. 154(b) by 206 days.

(21) Appl. No.: 16/795,429

(22) Filed: Feb. 19, 2020

(65) Prior Publication Data

US 2020/0207833 A1    Jul. 2, 2020

Related U.S. Application Data

(62) Division of application No. 14/784,015, filed as application No. PCT/SE2014/000047 on Apr. 10, 2014, now Pat. No. 11,274,139.

(30) Foreign Application Priority Data

Apr. 12, 2013 (SE) .................................. 1300271-2

(51) Int. Cl.
| | |
|---|---|
| A61K 47/69 | (2017.01) |
| A61K 47/62 | (2017.01) |
| A61K 9/00 | (2006.01) |
| A61K 38/17 | (2006.01) |
| A61K 38/00 | (2006.01) |

(Continued)

(52) U.S. Cl.
CPC ......... *C07K 14/70578* (2013.01); *A61K 9/00* (2013.01); *A61K 38/177* (2013.01); *A61K 47/62* (2017.08); *A61K 47/6911* (2017.08); *C07K 14/705* (2013.01); *C07K 14/70596* (2013.01); *F01C 1/3442* (2013.01); *F01C 21/102* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 6,899,863 B1 | 5/2005 | Dhellin et al. |
| 2004/0241176 A1 | 12/2004 | Lamparski et al. |

(Continued)

FOREIGN PATENT DOCUMENTS

| | | |
|---|---|---|
| EP | 2983721 | 2/2018 |
| WO | WO 94/21235 A1 | 9/1994 |

(Continued)

OTHER PUBLICATIONS

Alvarez-Erviti et al., "Delivery of siRNA to the Mouse Brain by Systemic Injection of Targeted Exosomes", Nature Biotechnology, (2011), vol. 29, No. 4, p. 341-345.

(Continued)

*Primary Examiner* — Kara M Peo
(74) *Attorney, Agent, or Firm* — Cooley LLP; Tanya Heare-Rowlands; Matthew Pavao

(57) ABSTRACT

The present invention pertains to inter alia methods for purifying extracellular vesicles including exposing a sample comprising at least one extracellular vesicle to ultrafiltration; and exposing the sample following the ultrafiltration in step (i) to size exclusion liquid chromatography.

13 Claims, 10 Drawing Sheets

Specification includes a Sequence Listing.

(51) Int. Cl.
    *C07K 14/705*     (2006.01)
    *F01C 21/10*     (2006.01)
    *F01C 1/344*     (2006.01)

(56) References Cited

U.S. PATENT DOCUMENTS

| | | |
|---|---|---|
| 2013/0028895 A1 | 1/2013 | Wulf |
| 2013/0059793 A1 | 3/2013 | Cardo-Vila et al. |
| 2016/0137716 A1 | 5/2016 | El Andaloussi et al. |

FOREIGN PATENT DOCUMENTS

| | | | |
|---|---|---|---|
| WO | WO 03/016522 | A2 | 2/2003 |
| WO | WO 2003/034275 | A2 | 4/2003 |
| WO | WO 2008/092153 | A3 | 7/2008 |
| WO | WO 2010/056337 | A2 | 5/2010 |
| WO | WO 2010/108048 | A2 | 9/2010 |
| WO | WO 2010/119256 | A1 | 10/2010 |
| WO | WO 2012/087241 | A1 | 6/2012 |
| WO | WO 2012/087241 | A9 | 6/2012 |
| WO | WO 2013/084000 | A2 | 6/2013 |
| WO | WO 2013/084001 | A1 | 6/2013 |

OTHER PUBLICATIONS

Clayton, Aled et al., "Antigen-presenting cell exosomes are protected from complementmediated lysis by expression of CD55 and CD59", Eur. J. Immunol., (2003), vol. 33, p. 522-531.

Danzer, Karin M. et al., "Exosomal cell-to-cell transmission of alpha synuclein oligomers", Molecular Neurodegeneration (2012), vol. 7, No. 42, p. 1-18.

El Andaloussi et al., "Exosomes for Targeted siRNA Delivery across Biological Barriers", Advanced Drug Delivery Reviews, vol. 65, No. 3, Mar. 2013, pp. 391-397.

El-Andaloussi et al., "Exosome-Mediated Delivery of siRNA in Vitro and in Vivo", Nature Protocols, (2012), vol. 7, No. 12, p. 2112-2126.

El Andaloussi, Samir, "Exosomes for macromolecular drug delivery". University of Oxford, ISIS Innovation, (2013), 20 pages.

Hawari, Feras I. et al., "Release of full-length 55-kDa TNF receptor 1 in exosome-like vesicles: A mechanism for generation of soluble cytokine receptors", PNAS, (2004), vol. 101, No. 5, p. 1297-1302.

Hedlund et al., "Thermal-and Oxidative Stress Causes Enhanced Release of NKG2D Ligand-Bearing Immunosuppressive Exosomes in Leukemia/Lymphoma T and B Cells", PLoS One, 2011, vol. 6, No. 2, 10 pages.

Lai, Ruenn Chai et al., "Derivation and characterization of human fetal MSCs: An alternative cell source for large-scale production of cardioprotective microparticles", Journal of Molecular and Cellular Cardiology, (2010), vol. 48, p. 1215-1224.

Nordin, Joel Z.M.D., et al., "Ultrafiltration with size-exclusion liquid chromatography for high yield isolation of extracellular vesicles preserving intact biophysical and functional properties", Nanomedicine: Nanotechnology, Biology and Medicine, (2015), vol. 11, p. 879-883.

Rood, Ilse M. et al., "Comparison of three methods for isolation of urinary microvesicles to idenitify biomarkers of nephrotic syndrome", Kidney International (2010), vol. 78, p. 810-816.

UniProt Database, Accession No. A0A0A0N0L2, 7 pages (last modified 2015).

International Preliminary Report on Patentability received for PCT Patent Application No. PCT/SE2014/000047, dated Oct. 22, 2015, 10 pages.

International Search Report and Written Opinion received for PCT Patent Application No. PCT/SE2014/000047, dated Oct. 21, 2014, 16 pages.

Invitation to Pay Additional Fees received for PCT Patent Application No. PCT/SE2014/000047, dated Sep. 5, 2014, 6 pages.

Battke, C. et al. "Tumour exosomes inhibit binding of tumour-reactive antibodies to tumour cells and reduce ADCC", Cancer Immunol Immunother, (2011), vol. 60, p. 639-648.

Ciravolo, V. et al. "Potential Role of HER2-Overexpressing Exosomes in Countering Trastuzumab-Based Therapy", Journal of Cellular Physiology, (2011), p. 658-667.

Fader, C. et al. "Induction of Autophagy Promotes Fusion of Multivesicular Bodies with Autophagic Vacuoles in K562 Cells", Traffic, (2008), vol. 9, p. 230-250.

Huang, C. "Receptor-Fc fusion therapeutics, traps, and MIMETIBODY™ technology", Current Opinion in Biotechnology, (2009), vol. 20, p. 692-699.

Maia, J. et al. "Exosome-Based Cell-Cell Communication in the Tumor Microenvironment", Frontiers in Cell and Developmental Biology, (2018), vol. 6, No. 18, 19 pages.

Latysheva et al., "Syntenin-1 Is a New Component of Tetraspanin-Enriched Microdomains: Mechanisms and Consequences of the Interaction of Syntenin-1 with CD63", Molecular and Cellular Biology, vol. 26, p. 7707-7718 (2006).

Lewis et al., "Interleukin-I and cancer progression: the emerging role of interleukin-1 receptor antagonist as a novel therapeutic agent in cancer treatment", Journal of Translational Medicine, vol. 4, p. 48-60 (2006).

Shen et al., "Protein Targeting to Exosomes/Microvesicles by Plasma Membrane Anchors", Journal of Biological Chemistry, vol. 286, No. 16, p. 14383-14395 (2011).

>murine CD63 (bold are sequences removed from CD63 to insert the constructs) (SEQ ID No 45)

MAVEGGMKCVKFLLYVLLLAFCACAVGLIAIGVAVQVVLKQAITHETTAGSLLPVVIIAVGAFLFLVAFVGCCGACKENYCLM
ITFAIFLSLIMLVEVAVAIAGYV**FRDQVKSEFNKSFQQQMQNYLKDNKTATILDKLQKENNCCGASNYTDWENIPGMAKDRVP
DSCCINITVGCGNDFKES**TIHTQGCVETIAIWLRKNILLVAAAALGIAFVEVLGIIFSCCLVKSIRSGYEVM

Below all parts in bold represent the insert (i.e. either TNFR1 or ACVR2b)

>psTNFR1a-Syt7-His TNFR1-Synaptotagmin (with His tag) (SEQ ID No 46)
MARG**IHPSGVTGLVPSLGDREKRDSLCPQGKYVHSKNNSICCTKCHKGTYLVSDCPSPGRDTVCRECEKGTFTASQNYLRQCL
SCKTCRKEMSQVEISPCQADKDTVCGCKENQFQRYLSETHFQCVDCSPCFNGTVTIPCKETQNTVCNCHAGFFLRESECVPCS
HCKKNEECMKLCLPPPLANVTNPQDSGT**SGGLYRDPEAASPGAPTRDVLLVSAIITVSLSVTIVLCGLCHWCQRKLGKRYKNS
LETVGTPDSHHHHHHGKLVWI >pLamp2b-sTNFR1a Lamp2b-TNFR1 (SEQ ID No 47)
MCLSPVKGAKLILIFLFLGAVQSNALIVNLTDSKGTCLYAR**GIHPSGVTGLVPSLGDREKRDSLCPQGKYVHSKNNSICCTKC
HKGTYLVSDCPSPGRDTVCRECEKGTFTASQNYLRQCLSCKTCRKEMSQVEISPCQADKDTVCGCKENQFQRYLSETHFQCVD
CSPCFNGTVTIPCKETQNTVCNCHAGFFLRESECVPCSHCKKNEECMKLCLPPPLANVTNPQDSGT**SGGAEWEMNFTITYETT
NQTNKTITIAVPDKATHDGSSCGDDRNSAKIMIQFGFAVSWAVNFTKEASHYSIHDIVLSYNTSDSTVFPGAVAKGVHTVKNP
ENFKVPLDVIFKCNSVLTYNLTPVVQKYWGIHLQAFVQNGTVSKNEQVCEEDQTPTTVAPIIHTTAPSTTTTLTPTSTPTPTP
TPTPTVGNYSIRNGNTTCLLATMGLQLNITEEKVPFIFNINPATTNFTGSCQPQSAQLRLNNSQIKYLDFIFAVKNEKRFYLK
EVNVYMYLANGSAFNISNKNLSFWDAPLGSSYMCNKEQVLSVSRAFQINTFNLKVQPFNVTKGQYSTAQECSLDDDTILIPII
VGAGLSGLIIVIVIAYLIGRRKTYAGYQTL >pmCD63-sTNFR1a (SEQ ID No 48)
MAVEGGMKCVKFLLYVLLLAFCACAVGLIAIGVAVQVVLKQAITHETTAGSLLPVVIIAVGAFLFLVAFVGCCGACKENYCLM
ITFAIFLSLIMLVEVAVAIAGYVGGSR**IHPSGVTGLVPSLGDREKRDSLCPQGKYVHSKNNSICCTKCHKGTYLVSDCPSPGR
DTVCRECEKGTFTASQNYLRQCLSCKTCRKEMSQVEISPCQADKDTVCGCKENQFQRYLSETHFQCVDCSPCFNGTVTIPCKE
TQNTVCNCHAGFFLRESECVPCSHCKKNEECMKLCLPPPLANVTNPQDSGT**EFGGIHTQGCVETIAIWLRKNILLVAAAALGI
AFVEVLGIIFSCCLVKSIRSGYEVMD >pSTNFR1a-Syt7-eGFP TNFR1-Synaptotagmin (with EGFP) (SEQ ID No 49)
MARG**IHPSGVTGLVPSLGDREKRDSLCPQGKYVHSKNNSICCTKCHKGTYLVSDCPSPGRDTVCRECEKGTFTASQNYLRQCL
SCKTCRKEMSQVEISPCQADKDTVCGCKENQFQRYLSETHFQCVDCSPCFNGTVTIPCKETQNTVCNCHAGFFLRESECVPCS
HCKKNEECMKLCLPPPLANVTNPQDSGT**SGGGSMYRDPEAASPGAPTRDVLLVSAIITVSLSVTIVLCGLCHWCQRKLGKRYK
NSLETVGTPDLPVATMVSKGEELFTGVVPILVELDGDVNGHKFSVSGEGEGDATYGKLTLKFICTTGKLPVPWPTLVTTLTYG
VQCFSRYPDHMKQHDFFKSAMPEGYVQERTIFFKDDGNYKTRAEVKFEGDTLVNRIELKGIDFKEDGNILGHKLEYNYNSHNV
YIMADKQKNGIKVNFKIRHNIEDGSVQLADHYQQNTPIGDGPVLLPDNHYLSTQSALSKDPNEKRDHMVLLEFVTAAGITLGM
DELYK >hACVR2b-Syndecan Activin-Syndecan construct (SEQ ID No 50)
MARAPWVALALLWGSLCA**GSGRGEAETRECIYYNANWELERTNQSGLERCEGEQDKRLHCYASWRNSSGTIELVKKGCWLDDF
NCYDRQECVATEENPQVYFCCCEGNFCNERFTHLPEAGGPEVTYEPPPTAPTLLT**VLAYSLLPIGGLSLIVLLAFWMYRHRKS
GGKDEGSYSLEEPKQANGGAYHKPTKQDEFYAGGGHHHHHHEFSKGEELFTGVVPILVELDGDVNGHKFSVSGEGEGDATYGK
LTLKFICTTGKLPVPWPTLVTTLTYGVQCFSRYPDHMKQHDFFKSAMPEGYVQERTIFFKDDGNYKTRAEVKFEGDTLVNRIE
LKGIDFKEDGNILGHKLEYNYNSHNVYIMADKQKNGIKVNFKIRHNIEDGSVQLADHYQQNTPIGDGPVLLPDNHYLSTQSAL
SKDPNEKRDHMVLLEFVTARRDHSRHGRAVQGI >pLamp2b-hACVR2b Lamp2b-Activin (SEQ ID No 51)
MCLSPVKGAKLILIFLFLGAVQSNALIVNLTDSKGTCLYAR**GSGRGEAETRECIYYNANWELERTNQSGLERCEGEQDKRLHC
YASWRNSSGTIELVKKGCWLDDFNCYDRQECVATEENPQVYFCCCEGNFCNERFTHLPEAGGPEVTYEPPPTAPTLLT**SGGAE
WEMNFTITYETTNQTNKTITIAVPDKATHDGSSCGDDRNSAKIMIQFGFAVSWAVNFTKEASHYSIHDIVLSYNTSDSTVFPG
AVAKGVHTVKNPENFKVPLDVIFKCNSVLTYNLTPVVQKYWGIHLQAFVQNGTVSKNEQVCEEDQTPTTVAPIIHTTAPSTTT
TLTPTSTPTPTPTPTPTVGNYSIRNGNTTCLLATMGLQLNITEEKVPFIFNINPATTNFTGSCQPQSAQLRLNNSQIKYLDFI
FAVKNEKRFYLKEVNVYMYLANGSAFNISNKNLSFWDAPLGSSYMCNKEQVLSVSRAFQINTFNLKVQPFNVTKGQYSTAQEC
SLDDDTILIPIIVGAGLSGLIIVIVIAYLIGRRKTYAGYQTL >phACVR2b-Syt7-His Activin-Synaptotagmin (SEQ ID No 52)
MARG**SGRGEAETRECIYYNANWELERTNQSGLERCEGEQDKRLHCYASWRNSSGTIELVKKGCWLDDFNCYDRQECVATEENP
QVYFCCCEGNFCNERFTHLPEAGGPEVTYEPPPTAPTLLT**SGGLYRDPEAASPGAPTRDVLLVSAIITVSLSVTIVLCGLCHW
CQRKLGKRYKNSLETVGTPDSHHHHHHGKLVWI

FIG. 6

SEQUENCE LISTING

<160> NUMBER OF SEQ ID NOS: 52

<210> SEQ ID NO 1
<211> LENGTH: 468
<212> TYPE: PRT
<213> ORGANISM: Homo sapiens

<400> SEQUENCE: 1

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255
```

-continued

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
        450                 455                 460

Phe Phe Pro Arg
465

<210> SEQ ID NO 2
<211> LENGTH: 857
<212> TYPE: PRT
<213> ORGANISM: Homo sapiens

<400> SEQUENCE: 2

Met Leu Thr Leu Gln Thr Trp Leu Val Gln Ala Leu Phe Ile Phe Leu
1                   5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
        50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

```
Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
                195                 200                 205

Ser Asp His Ile Asn Phe Asp Pro Val Tyr Lys Val Lys Pro Asn Pro
            210                 215                 220

Pro His Asn Leu Ser Val Ile Asn Ser Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
                290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
                355                 360                 365

Thr Leu Thr Arg Trp Lys Ser His Leu Gln Asn Tyr Thr Val Asn Ala
                370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Gly Asn Leu Ala Glu Ser Lys Cys Tyr Leu
                420                 425                 430

Ile Thr Val Thr Pro Val Tyr Ala Asp Gly Pro Gly Ser Pro Glu Ser
                435                 440                 445

Ile Lys Ala Tyr Leu Lys Gln Ala Pro Pro Ser Lys Gly Pro Thr Val
                450                 455                 460

Arg Thr Lys Lys Val Gly Lys Asn Glu Ala Val Leu Glu Trp Asp Gln
465                 470                 475                 480

Leu Pro Val Asp Val Gln Asn Gly Phe Ile Arg Asn Tyr Thr Ile Phe
                485                 490                 495

Tyr Arg Thr Ile Ile Gly Asn Glu Thr Ala Val Asn Val Asp Ser Ser
                500                 505                 510

His Thr Glu Tyr Thr Leu Ser Ser Leu Thr Ser Asp Thr Leu Tyr Met
                515                 520                 525

Val Arg Met Ala Ala Tyr Thr Asp Glu Gly Gly Lys Asp Gly Pro Glu
                530                 535                 540

Phe Thr Phe Thr Thr Pro Lys Phe Ala Gln Gly Glu Ile Glu Ala Ile
545                 550                 555                 560

Val Val Pro Val Cys Leu Ala Phe Leu Leu Thr Thr Leu Leu Gly Val
                565                 570                 575
```

-continued

```
Leu Phe Cys Phe Asn Lys Arg Asp Leu Ile Lys Lys His Ile Trp Pro
                580                 585                 590
Asn Val Pro Asp Pro Ser Lys Ser His Ile Ala Gln Trp Ser Pro His
            595                 600                 605
Thr Pro Pro Arg His Asn Phe Asn Ser Lys Asp Gln Met Tyr Ser Asp
        610                 615                 620
Gly Asn Phe Thr Asp Val Ser Val Glu Ile Glu Ala Asn Asp Lys
625                 630                 635                 640
Lys Pro Phe Pro Glu Asp Leu Lys Ser Leu Asp Leu Phe Lys Lys Glu
                645                 650                 655
Lys Ile Asn Thr Glu Gly His Ser Ser Gly Ile Gly Gly Ser Ser Cys
            660                 665                 670
Met Ser Ser Ser Arg Pro Ser Ile Ser Ser Ser Asp Glu Asn Glu Ser
        675                 680                 685
Ser Gln Asn Thr Ser Ser Thr Val Gln Tyr Ser Thr Val Val His Ser
    690                 695                 700
Gly Tyr Arg His Gln Val Pro Ser Val Gln Val Phe Ser Arg Ser Glu
705                 710                 715                 720
Ser Thr Gln Pro Leu Leu Asp Ser Glu Glu Arg Pro Glu Asp Leu Gln
                725                 730                 735
Leu Val Asp His Val Asp Gly Asp Gly Ile Leu Pro Arg Gln Gln
            740                 745                 750
Tyr Phe Lys Gln Asn Cys Ser Gln His Glu Ser Ser Pro Asp Ile Ser
        755                 760                 765
His Phe Glu Arg Ser Lys Gln Val Ser Ser Val Asn Glu Glu Asp Phe
    770                 775                 780
Val Arg Leu Lys Gln Gln Ile Ser Asp His Ile Ser Gln Ser Cys Gly
785                 790                 795                 800
Ser Gly Gln Met Lys Met Phe Gln Glu Val Ser Ala Ala Asp Ala Phe
                805                 810                 815
Gly Pro Gly Thr Glu Gly Gln Val Glu Arg Phe Glu Thr Val Gly Met
            820                 825                 830
Glu Ala Ala Thr Asp Glu Gly Met Pro Lys Ser Tyr Leu Pro Gln Thr
        835                 840                 845
Val Arg Gln Gly Gly Tyr Met Pro Gln
    850                 855

<210> SEQ ID NO 3
<211> LENGTH: 569
<212> TYPE: PRT
<213> ORGANISM: Homo sapiens

<400> SEQUENCE: 3

Met Lys Val Leu Leu Arg Leu Ile Cys Phe Ile Ala Leu Leu Ile Ser
1               5                   10                  15
Ser Leu Glu Ala Asp Lys Cys Lys Glu Arg Glu Glu Lys Ile Ile Leu
                20                  25                  30
Val Ser Ser Ala Asn Glu Ile Asp Val Arg Pro Cys Pro Leu Asn Pro
            35                  40                  45
Asn Glu His Lys Gly Thr Ile Thr Trp Tyr Lys Asp Asp Ser Lys Thr
        50                  55                  60
Pro Val Ser Thr Glu Gln Ala Ser Arg Ile His Gln His Lys Glu Lys
65                  70                  75                  80
Leu Trp Phe Val Pro Ala Lys Val Glu Asp Ser Gly His Tyr Tyr Cys
                85                  90                  95
```

```
Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
            130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
            210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
            290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
            450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510
```

```
Ile Arg Trp Ser Gly Asp Phe Thr Gln Gly Pro Gln Ser Ala Lys Thr
            515                 520                 525
Arg Phe Trp Lys Asn Val Arg Tyr His Met Pro Val Gln Arg Arg Ser
        530                 535                 540
Pro Ser Ser Lys His Gln Leu Leu Ser Pro Ala Thr Lys Glu Lys Leu
545                 550                 555                 560
Gln Arg Glu Ala His Val Pro Leu Gly
                565

<210> SEQ ID NO 4
<211> LENGTH: 660
<212> TYPE: PRT
<213> ORGANISM: Homo sapiens

<400> SEQUENCE: 4

Met Glu Pro Leu Val Thr Trp Val Val Pro Leu Leu Phe Leu Phe Leu
1               5                   10                  15
Leu Ser Arg Gln Gly Ala Ala Cys Arg Thr Ser Glu Cys Cys Phe Gln
                20                  25                  30
Asp Pro Pro Tyr Pro Asp Ala Asp Ser Gly Ser Ala Ser Gly Pro Arg
            35                  40                  45
Asp Leu Arg Cys Tyr Arg Ile Ser Ser Asp Arg Tyr Glu Cys Ser Trp
    50                  55                  60
Gln Tyr Glu Gly Pro Thr Ala Gly Val Ser His Phe Leu Arg Cys Cys
65                  70                  75                  80
Leu Ser Ser Gly Arg Cys Cys Tyr Phe Ala Ala Gly Ser Ala Thr Arg
                85                  90                  95
Leu Gln Phe Ser Asp Gln Ala Gly Val Ser Val Leu Tyr Thr Val Thr
            100                 105                 110
Leu Trp Val Glu Ser Trp Ala Arg Asn Gln Thr Glu Lys Ser Pro Glu
        115                 120                 125
Val Thr Leu Gln Leu Tyr Asn Ser Val Lys Tyr Glu Pro Pro Leu Gly
    130                 135                 140
Asp Ile Lys Val Ser Lys Leu Ala Gly Gln Leu Arg Met Glu Trp Glu
145                 150                 155                 160
Thr Pro Asp Asn Gln Val Gly Ala Glu Val Gln Phe Arg His Arg Thr
                165                 170                 175
Pro Ser Ser Pro Trp Lys Leu Gly Asp Cys Gly Pro Gln Asp Asp Asp
            180                 185                 190
Thr Glu Ser Cys Leu Cys Pro Leu Glu Met Asn Val Ala Gln Glu Phe
        195                 200                 205
Gln Leu Arg Arg Arg Gln Leu Gly Ser Gln Gly Ser Ser Trp Ser Lys
    210                 215                 220
Trp Ser Ser Pro Val Cys Val Pro Pro Glu Asn Pro Pro Gln Pro Gln
225                 230                 235                 240
Val Arg Phe Ser Val Glu Gln Leu Gly Gln Asp Gly Arg Arg Arg Leu
                245                 250                 255
Thr Leu Lys Glu Gln Pro Thr Gln Leu Glu Leu Pro Glu Gly Cys Gln
            260                 265                 270
Gly Leu Ala Pro Gly Thr Glu Val Thr Tyr Arg Leu Gln Leu His Met
        275                 280                 285
Leu Ser Cys Pro Cys Lys Ala Lys Ala Thr Arg Thr Leu His Leu Gly
    290                 295                 300
Lys Met Pro Tyr Leu Ser Gly Ala Ala Tyr Asn Val Ala Val Ile Ser
305                 310                 315                 320
```

Ser Asn Gln Phe Gly Pro Gly Leu Asn Gln Thr Trp His Ile Pro Ala
            325                 330                 335

Asp Thr His Thr Glu Pro Val Ala Leu Asn Ile Ser Val Gly Thr Asn
            340                 345                 350

Gly Thr Thr Met Tyr Trp Pro Arg Ala Gln Ser Met Thr Tyr Cys
            355                 360                 365

Ile Glu Trp Gln Pro Val Gly Gln Asp Gly Leu Ala Thr Cys Ser
    370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
                420                 425                 430

Val Leu Ser Thr Tyr His Phe Gly Gly Asn Ala Ser Ala Ala Gly Thr
            435                 440                 445

Pro His His Val Ser Val Lys Asn His Ser Leu Asp Ser Val Ser Val
    450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
                500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
            530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
                580                 585                 590

Pro Gly Gly Lys Glu Thr Trp Gln Trp Ile Asn Pro Val Asp Phe Gln
                595                 600                 605

Glu Glu Ala Ser Leu Gln Glu Ala Leu Val Val Glu Met Ser Trp Asp
            610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
                645                 650                 655

Arg Cys Asp Arg
            660

<210> SEQ ID NO 5
<211> LENGTH: 659
<212> TYPE: PRT
<213> ORGANISM: Homo sapiens

<400> SEQUENCE: 5

Met Ala His Thr Phe Arg Gly Cys Ser Leu Ala Phe Met Phe Ile Ile
1               5                   10                  15

Thr Trp Leu Leu Ile Lys Ala Lys Ile Asp Ala Cys Lys Arg Gly Asp

```
            20                  25                  30
Val Thr Val Lys Pro Ser His Val Ile Leu Gly Ser Thr Val Asn
         35                  40                  45
Ile Thr Cys Ser Leu Lys Pro Arg Gln Gly Cys Phe His Tyr Ser Arg
 50                  55                  60
Arg Asn Lys Leu Ile Leu Tyr Lys Phe Asp Arg Ile Asn Phe His
 65                  70                  75                  80
His Gly His Ser Leu Asn Ser Gln Val Thr Gly Leu Pro Leu Gly Thr
                     85                  90                  95
Thr Leu Phe Val Cys Lys Leu Ala Cys Ile Asn Ser Asp Glu Ile Gln
                100                 105                 110
Ile Cys Gly Ala Glu Ile Phe Val Gly Val Ala Pro Glu Gln Pro Gln
                115                 120                 125
Asn Leu Ser Cys Ile Gln Lys Gly Glu Gln Gly Thr Val Ala Cys Thr
                130                 135                 140
Trp Glu Arg Gly Arg Asp Thr His Leu Tyr Thr Glu Tyr Thr Leu Gln
145                 150                 155                 160
Leu Ser Gly Pro Lys Asn Leu Thr Trp Gln Lys Gln Cys Lys Asp Ile
                165                 170                 175
Tyr Cys Asp Tyr Leu Asp Phe Gly Ile Asn Leu Thr Pro Glu Ser Pro
                180                 185                 190
Glu Ser Asn Phe Thr Ala Lys Val Thr Ala Val Asn Ser Leu Gly Ser
                195                 200                 205
Ser Ser Ser Leu Pro Ser Thr Phe Thr Phe Leu Asp Ile Val Arg Pro
        210                 215                 220
Leu Pro Pro Trp Asp Ile Arg Ile Lys Phe Gln Lys Ala Ser Val Ser
225                 230                 235                 240
Arg Cys Thr Leu Tyr Trp Arg Asp Glu Gly Leu Val Leu Leu Asn Arg
                245                 250                 255
Leu Arg Tyr Arg Pro Ser Asn Ser Arg Leu Trp Asn Met Val Asn Val
                260                 265                 270
Thr Lys Ala Lys Gly Arg His Asp Leu Leu Asp Leu Lys Pro Phe Thr
                275                 280                 285
Glu Tyr Glu Phe Gln Ile Ser Ser Lys Leu His Leu Tyr Lys Gly Ser
        290                 295                 300
Trp Ser Asp Trp Ser Glu Ser Leu Arg Ala Gln Thr Pro Glu Glu Glu
305                 310                 315                 320
Pro Thr Gly Met Leu Asp Val Trp Tyr Met Lys Arg His Ile Asp Tyr
                325                 330                 335
Ser Arg Gln Gln Ile Ser Leu Phe Trp Lys Asn Leu Ser Val Ser Glu
                340                 345                 350
Ala Arg Gly Lys Ile Leu His Tyr Gln Val Thr Leu Gln Glu Leu Thr
                355                 360                 365
Gly Gly Lys Ala Met Thr Gln Asn Ile Thr Gly His Thr Ser Trp Thr
        370                 375                 380
Thr Val Ile Pro Arg Thr Gly Asn Trp Ala Val Ala Val Ser Ala Ala
385                 390                 395                 400
Asn Ser Lys Gly Ser Ser Leu Pro Thr Arg Ile Asn Ile Met Asn Leu
                405                 410                 415
Cys Glu Ala Gly Leu Leu Ala Pro Arg Gln Val Ser Ala Asn Ser Glu
                420                 425                 430
Gly Met Asp Asn Ile Leu Val Thr Trp Gln Pro Pro Arg Lys Asp Pro
                435                 440                 445
```

-continued

```
Ser Ala Val Gln Glu Tyr Val Glu Trp Arg Glu Leu His Pro Gly
    450                 455                 460
Gly Asp Thr Gln Val Pro Leu Asn Trp Leu Arg Ser Arg Pro Tyr Asn
465                 470                 475                 480
Val Ser Ala Leu Ile Ser Glu Asn Ile Lys Ser Tyr Ile Cys Tyr Glu
                485                 490                 495
Ile Arg Val Tyr Ala Leu Ser Gly Asp Gln Gly Gly Cys Ser Ser Ile
                500                 505                 510
Leu Gly Asn Ser Lys His Lys Ala Pro Leu Ser Gly Pro His Ile Asn
            515                 520                 525
Ala Ile Thr Glu Glu Lys Gly Ser Ile Leu Ile Ser Trp Asn Ser Ile
530                 535                 540
Pro Val Gln Glu Gln Met Gly Cys Leu Leu His Tyr Arg Ile Tyr Trp
545                 550                 555                 560
Lys Glu Arg Asp Ser Asn Ser Gln Pro Gln Leu Cys Glu Ile Pro Tyr
                565                 570                 575
Arg Val Ser Gln Asn Ser His Pro Ile Asn Ser Leu Gln Pro Arg Val
                580                 585                 590
Thr Tyr Val Leu Trp Met Thr Ala Leu Thr Ala Ala Gly Glu Ser Ser
            595                 600                 605
His Gly Asn Glu Arg Glu Phe Cys Leu Gln Gly Lys Ala Asn Trp Met
610                 615                 620
Ala Phe Val Ala Pro Ser Ile Cys Ile Ala Ile Met Val Gly Ile
625                 630                 635                 640
Phe Ser Thr His Tyr Phe Gln Gln Lys Arg His Ser Cys Pro Trp
                645                 650                 655
Thr Gly Ser

<210> SEQ ID NO 6
<211> LENGTH: 832
<212> TYPE: PRT
<213> ORGANISM: Homo sapiens

<400> SEQUENCE: 6

Met Gly Ala Ala Arg Ser Pro Pro Ser Ala Val Pro Gly Pro Leu Leu
1               5                   10                  15
Gly Leu Leu Leu Leu Leu Leu Gly Val Leu Ala Pro Gly Gly Ala Ser
                20                  25                  30
Leu Arg Leu Leu Asp His Arg Ala Leu Val Cys Ser Gln Pro Gly Leu
            35                  40                  45
Asn Cys Thr Val Lys Asn Ser Thr Cys Leu Asp Asp Ser Trp Ile His
        50                  55                  60
Pro Arg Asn Leu Thr Pro Ser Ser Pro Lys Asp Leu Gln Ile Gln Leu
65                  70                  75                  80
His Phe Ala His Thr Gln Gln Gly Asp Leu Phe Pro Val Ala His Ile
                85                  90                  95
Glu Trp Thr Leu Gln Thr Asp Ala Ser Ile Leu Tyr Leu Glu Gly Ala
                100                 105                 110
Glu Leu Ser Val Leu Gln Leu Asn Thr Asn Glu Arg Leu Cys Val Arg
            115                 120                 125
Phe Glu Phe Leu Ser Lys Leu Arg His His His Arg Arg Trp Arg Phe
        130                 135                 140
Thr Phe Ser His Phe Val Val Asp Pro Asp Gln Glu Tyr Glu Val Thr
145                 150                 155                 160
```

```
Val His His Leu Pro Lys Pro Ile Pro Asp Gly Asp Pro Asn His Gln
            165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
            275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Gly Pro Gly Ser Glu Lys
305                 310                 315                 320

Tyr Ser Asp Asp Thr Lys Tyr Thr Asp Gly Leu Pro Ala Ala Asp Leu
                325                 330                 335

Ile Pro Pro Pro Leu Lys Pro Arg Lys Val Trp Ile Ile Tyr Ser Ala
                340                 345                 350

Asp His Pro Leu Tyr Val Asp Val Val Leu Lys Phe Ala Gln Phe Leu
            355                 360                 365

Leu Thr Ala Cys Gly Thr Glu Val Ala Leu Asp Leu Leu Glu Glu Gln
    370                 375                 380

Ala Ile Ser Glu Ala Gly Val Met Thr Trp Val Gly Arg Gln Lys Gln
385                 390                 395                 400

Glu Met Val Glu Ser Asn Ser Lys Ile Ile Val Leu Cys Ser Arg Gly
                405                 410                 415

Thr Arg Ala Lys Trp Gln Ala Leu Leu Gly Arg Gly Ala Pro Val Arg
                420                 425                 430

Leu Arg Cys Asp His Gly Lys Pro Val Gly Asp Leu Phe Thr Ala Ala
            435                 440                 445

Met Asn Met Ile Leu Pro Asp Phe Lys Arg Pro Ala Cys Phe Gly Thr
    450                 455                 460

Tyr Val Val Cys Tyr Phe Ser Glu Val Ser Cys Asp Gly Asp Val Pro
465                 470                 475                 480

Asp Leu Phe Gly Ala Ala Pro Arg Tyr Pro Leu Met Asp Arg Phe Glu
                485                 490                 495

Glu Val Tyr Phe Arg Ile Gln Asp Leu Glu Met Phe Gln Pro Gly Arg
                500                 505                 510

Met His Arg Val Gly Glu Leu Ser Gly Asp Asn Tyr Leu Arg Ser Pro
            515                 520                 525

Gly Gly Arg Gln Leu Arg Ala Ala Leu Asp Arg Phe Arg Asp Trp Gln
    530                 535                 540

Val Arg Cys Pro Asp Trp Phe Glu Cys Glu Asn Leu Tyr Ser Ala Asp
545                 550                 555                 560

Asp Gln Asp Ala Pro Ser Leu Asp Glu Glu Val Phe Glu Glu Pro Leu
                565                 570                 575
```

Leu Pro Pro Gly Thr Gly Ile Val Lys Arg Ala Pro Leu Val Arg Glu
            580                 585                 590

Pro Gly Ser Gln Ala Cys Leu Ala Ile Asp Pro Leu Val Gly Glu Glu
        595                 600                 605

Gly Gly Ala Ala Val Ala Lys Leu Glu Pro His Leu Gln Pro Arg Gly
    610                 615                 620

Gln Pro Ala Pro Gln Pro Leu His Thr Leu Val Leu Ala Ala Glu Glu
625                 630                 635                 640

Gly Ala Leu Val Ala Ala Val Glu Pro Gly Pro Leu Ala Asp Gly Ala
                645                 650                 655

Ala Val Arg Leu Ala Leu Ala Gly Glu Gly Glu Ala Cys Pro Leu Leu
            660                 665                 670

Gly Ser Pro Gly Ala Gly Arg Asn Ser Val Leu Phe Leu Pro Val Asp
        675                 680                 685

Pro Glu Asp Ser Pro Leu Gly Ser Ser Thr Pro Met Ala Ser Pro Asp
    690                 695                 700

Leu Leu Pro Glu Asp Val Arg Glu His Leu Glu Gly Leu Met Leu Ser
705                 710                 715                 720

Leu Phe Glu Gln Ser Leu Ser Cys Gln Ala Gln Gly Gly Cys Ser Arg
                725                 730                 735

Pro Ala Met Val Leu Thr Asp Pro His Thr Pro Tyr Glu Glu Glu Gln
            740                 745                 750

Arg Gln Ser Val Gln Ser Asp Gln Gly Tyr Ile Ser Arg Ser Ser Pro
        755                 760                 765

Gln Pro Pro Glu Gly Leu Thr Glu Met Glu Glu Glu Glu Glu Glu Glu
    770                 775                 780

Gln Asp Pro Gly Lys Pro Ala Leu Pro Leu Ser Pro Glu Asp Leu Glu
785                 790                 795                 800

Ser Leu Arg Ser Leu Gln Arg Gln Leu Leu Phe Arg Gln Leu Gln Lys
                805                 810                 815

Asn Ser Gly Trp Asp Thr Met Gly Ser Glu Ser Glu Gly Pro Ser Ala
            820                 825                 830

<210> SEQ ID NO 7
<211> LENGTH: 502
<212> TYPE: PRT
<213> ORGANISM: Homo sapiens

<400> SEQUENCE: 7

Met Ser Leu Val Leu Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
            260                 265                 270

Gln Thr Gly Val Pro Phe Pro Leu Asp Asn Asn Lys Ser Lys Pro Gly
        275                 280                 285

Gly Trp Leu Pro Leu Leu Leu Ser Leu Leu Val Ala Thr Trp Val
    290                 295                 300

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
                325                 330                 335

Val Tyr Pro Ser Glu Ile Cys Phe His His Thr Ile Cys Tyr Phe Thr
            340                 345                 350

Glu Phe Leu Gln Asn His Cys Arg Ser Glu Val Ile Leu Glu Lys Trp
        355                 360                 365

Gln Lys Lys Lys Ile Ala Glu Met Gly Pro Val Gln Trp Leu Ala Thr
    370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
                405                 410                 415

Glu Asn Ser Gln Asp Leu Phe Pro Leu Ala Phe Asn Leu Phe Cys Ser
            420                 425                 430

Asp Leu Arg Ser Gln Ile His Leu His Lys Tyr Val Val Val Tyr Phe
        435                 440                 445

Arg Glu Ile Asp Thr Lys Asp Asp Tyr Asn Ala Leu Ser Val Cys Pro
    450                 455                 460

Lys Tyr His Leu Met Lys Asp Ala Thr Ala Phe Cys Ala Glu Leu Leu
465                 470                 475                 480

His Val Lys Gln Gln Val Ser Ala Gly Lys Arg Ser Gln Ala Cys His
                485                 490                 495

Asp Gly Cys Cys Ser Leu
            500

<210> SEQ ID NO 8
<211> LENGTH: 707
<212> TYPE: PRT
<213> ORGANISM: Homo sapiens

<400> SEQUENCE: 8

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
        420                 425                 430

Glu Tyr Leu Leu Gln Asp Leu Gln Ser Gly Gln Cys Leu Gln Leu Trp
            435                 440                 445

Asp Asp Asp Leu Gly Ala Leu Trp Ala Cys Pro Met Asp Lys Tyr Ile
        450                 455                 460

His Lys Arg Trp Ala Leu Val Trp Leu Ala Cys Leu Leu Phe Ala Ala
465                 470                 475                 480

Ala Leu Ser Leu Ile Leu Leu Lys Lys Asp His Ala Lys Ala Ala
                485                 490                 495

Ala Arg Gly Arg Ala Ala Leu Leu Tyr Ser Ala Asp Ser Gly
                500                 505                 510

Phe Glu Arg Leu Val Gly Ala Leu Ala Ser Ala Leu Cys Gln Leu Pro
            515                 520                 525

Leu Arg Val Ala Val Asp Leu Trp Ser Arg Arg Glu Leu Ser Ala Gln
530                 535                 540

Gly Pro Val Ala Trp Phe His Ala Gln Arg Arg Gln Thr Leu Gln Glu
545                 550                 555                 560

Gly Gly Val Val Val Leu Leu Phe Ser Pro Gly Ala Val Ala Leu Cys
                565                 570                 575

Ser Glu Trp Leu Gln Asp Gly Val Ser Gly Pro Gly Ala His Gly Pro
            580                 585                 590

His Asp Ala Phe Arg Ala Ser Leu Ser Cys Val Leu Pro Asp Phe Leu
        595                 600                 605

Gln Gly Arg Ala Pro Gly Ser Tyr Val Gly Ala Cys Phe Asp Arg Leu
    610                 615                 620

Leu His Pro Asp Ala Val Pro Ala Leu Phe Arg Thr Val Pro Val Phe
625                 630                 635                 640

Thr Leu Pro Ser Gln Leu Pro Asp Phe Leu Gly Ala Leu Gln Gln Pro
                645                 650                 655

Arg Ala Pro Arg Ser Gly Arg Leu Gln Glu Arg Ala Glu Gln Val Ser
            660                 665                 670

Arg Ala Leu Gln Pro Ala Leu Asp Ser Tyr Phe His Pro Pro Gly Thr
        675                 680                 685

Pro Ala Pro Gly Arg Gly Val Gly Pro Gly Ala Gly Pro Gly Ala Gly
    690                 695                 700

Asp Gly Thr
705

<210> SEQ ID NO 9
<211> LENGTH: 711
<212> TYPE: PRT
<213> ORGANISM: Homo sapiens

<400> SEQUENCE: 9

Met Lys Ala Ala Ala Arg Pro Arg Leu Cys Val Ala Asn Glu Gly Val
1               5                   10                  15

Gly Pro Ala Ser Arg Asn Ser Gly Leu Tyr Asn Ile Thr Phe Lys Tyr
            20                  25                  30

Asp Asn Cys Thr Thr Tyr Leu Asn Pro Val Gly Lys His Val Ile Ala
        35                  40                  45

Asp Ala Gln Asn Ile Thr Ile Ser Gln Tyr Ala Cys His Asp Gln Val
    50                  55                  60

Ala Val Thr Ile Leu Trp Ser Pro Gly Ala Leu Gly Ile Glu Phe Leu

```
            65                  70                  75                  80
Lys Gly Phe Arg Val Ile Leu Glu Glu Leu Lys Ser Glu Gly Arg Gln
                    85                  90                  95
Cys Gln Gln Leu Ile Leu Lys Asp Pro Lys Gln Leu Asn Ser Ser Phe
                100                 105                 110
Lys Arg Thr Gly Met Glu Ser Gln Pro Phe Leu Asn Met Lys Phe Glu
                115                 120                 125
Thr Asp Tyr Phe Val Lys Val Pro Phe Pro Ser Ile Lys Asn Glu
            130                 135                 140
Ser Asn Tyr His Pro Phe Phe Arg Thr Arg Ala Cys Asp Leu Leu
145                 150                 155                 160
Leu Gln Pro Asp Asn Leu Ala Cys Lys Pro Phe Trp Lys Pro Arg Asn
                165                 170                 175
Leu Asn Ile Ser Gln His Gly Ser Asp Met Gln Val Ser Phe Asp His
                180                 185                 190
Ala Pro His Asn Phe Gly Phe Arg Phe Phe Tyr Leu His Tyr Lys Leu
                195                 200                 205
Lys His Glu Gly Pro Phe Lys Arg Lys Thr Cys Lys Gln Glu Gln Thr
            210                 215                 220
Thr Glu Thr Thr Ser Cys Leu Leu Gln Asn Val Ser Pro Gly Asp Tyr
225                 230                 235                 240
Ile Ile Glu Leu Val Asp Asp Thr Asn Thr Thr Arg Lys Val Met His
                245                 250                 255
Tyr Ala Leu Lys Pro Val His Ser Pro Trp Ala Gly Pro Ile Arg Ala
                260                 265                 270
Val Ala Ile Thr Val Pro Leu Val Val Ile Ser Ala Phe Ala Thr Leu
            275                 280                 285
Phe Thr Val Met Cys Arg Lys Lys Gln Gln Glu Asn Ile Tyr Ser His
            290                 295                 300
Leu Asp Glu Glu Ser Ser Glu Ser Ser Thr Tyr Thr Ala Ala Leu Pro
305                 310                 315                 320
Arg Glu Arg Leu Arg Pro Arg Pro Lys Val Phe Leu Cys Tyr Ser Ser
                325                 330                 335
Lys Asp Gly Gln Asn His Met Asn Val Val Gln Cys Phe Ala Tyr Phe
                340                 345                 350
Leu Gln Asp Phe Cys Gly Cys Glu Val Ala Leu Asp Leu Trp Glu Asp
            355                 360                 365
Phe Ser Leu Cys Arg Glu Gly Gln Arg Glu Trp Val Ile Gln Lys Ile
370                 375                 380
His Glu Ser Gln Phe Ile Ile Val Val Cys Ser Lys Gly Met Lys Tyr
385                 390                 395                 400
Phe Val Asp Lys Lys Asn Tyr Lys His Lys Gly Gly Arg Gly Ser
                405                 410                 415
Gly Lys Gly Glu Leu Phe Leu Val Ala Val Ser Ala Ile Ala Glu Lys
            420                 425                 430
Leu Arg Gln Ala Lys Gln Ser Ser Ala Ala Leu Ser Lys Phe Ile
            435                 440                 445
Ala Val Tyr Phe Asp Tyr Ser Cys Glu Gly Asp Val Pro Gly Ile Leu
            450                 455                 460
Asp Leu Ser Thr Lys Tyr Arg Leu Met Asp Asn Leu Pro Gln Leu Cys
465                 470                 475                 480
Ser His Leu His Ser Arg Asp His Gly Leu Gln Glu Pro Gly Gln His
                485                 490                 495
```

```
Thr Arg Gln Gly Ser Arg Arg Asn Tyr Phe Arg Ser Lys Ser Gly Arg
                500                 505                 510

Ser Leu Tyr Val Ala Ile Cys Asn Met His Gln Phe Ile Asp Glu Glu
            515                 520                 525

Pro Asp Trp Phe Glu Lys Gln Phe Val Pro His Pro Pro Leu
530                 535                 540

Arg Tyr Arg Glu Pro Val Leu Glu Lys Phe Asp Ser Gly Leu Val Leu
545                 550                 555                 560

Asn Asp Val Met Cys Lys Pro Gly Pro Glu Ser Asp Phe Cys Leu Lys
                565                 570                 575

Val Glu Ala Ala Val Leu Gly Ala Thr Gly Pro Ala Asp Ser Gln His
            580                 585                 590

Glu Ser Gln His Gly Gly Leu Asp Gln Asp Gly Glu Ala Arg Pro Ala
        595                 600                 605

Leu Asp Gly Ser Ala Ala Leu Gln Pro Leu Leu His Thr Val Lys Ala
610                 615                 620

Gly Ser Pro Ser Asp Met Pro Arg Asp Ser Gly Ile Tyr Asp Ser Ser
625                 630                 635                 640

Val Pro Ser Ser Glu Leu Ser Leu Pro Leu Met Glu Gly Leu Ser Thr
                645                 650                 655

Asp Gln Thr Glu Thr Ser Ser Leu Thr Glu Ser Val Ser Ser Ser Ser
            660                 665                 670

Gly Leu Gly Glu Glu Pro Pro Ala Leu Pro Ser Lys Leu Leu Ser
        675                 680                 685

Ser Gly Ser Cys Lys Ala Asp Leu Gly Cys Arg Ser Tyr Thr Asp Glu
690                 695                 700

Leu His Ala Val Ala Pro Leu
705                 710

<210> SEQ ID NO 10
<211> LENGTH: 667
<212> TYPE: PRT
<213> ORGANISM: Homo sapiens

<400> SEQUENCE: 10

Met Gly Ser Ser Arg Leu Ala Ala Leu Leu Pro Leu Leu Leu Leu Ile
1               5                   10                  15

Val Ile Asp Leu Ser Asp Ser Ala Gly Ile Gly Phe Arg His Leu Pro
            20                  25                  30

His Trp Asn Thr Arg Cys Pro Leu Ala Ser His Thr Asp Asp Ser Phe
        35                  40                  45

Thr Gly Ser Ser Ala Tyr Ile Pro Cys Arg Thr Trp Trp Ala Leu Phe
    50                  55                  60

Ser Thr Lys Pro Trp Cys Val Arg Val Trp His Cys Ser Arg Cys Leu
65                  70                  75                  80

Cys Gln His Leu Leu Ser Gly Gly Ser Gly Leu Gln Arg Gly Leu Phe
                85                  90                  95

His Leu Leu Val Gln Lys Ser Lys Lys Ser Thr Phe Lys Phe Tyr
            100                 105                 110

Arg Arg His Lys Met Pro Ala Pro Ala Gln Arg Lys Leu Leu Pro Arg
        115                 120                 125

Arg His Leu Ser Glu Lys Ser His His Ile Ser Ile Pro Ser Pro Asp
    130                 135                 140

Ile Ser His Lys Gly Leu Arg Ser Lys Arg Thr Gln Pro Ser Asp Pro
```

```
            145                 150                 155                 160
        Glu Thr Trp Glu Ser Leu Pro Arg Leu Asp Ser Gln Arg His Gly Gly
                        165                 170                 175

Pro Glu Phe Ser Phe Asp Leu Leu Pro Glu Ala Arg Ala Ile Arg Val
                        180                 185                 190

Thr Ile Ser Ser Gly Pro Glu Val Ser Val Arg Leu Cys His Gln Trp
                        195                 200                 205

Ala Leu Glu Cys Glu Glu Leu Ser Ser Pro Tyr Asp Val Gln Lys Ile
                        210                 215                 220

Val Ser Gly Gly His Thr Val Glu Leu Pro Tyr Glu Phe Leu Leu Pro
        225                 230                 235                 240

Cys Leu Cys Ile Glu Ala Ser Tyr Leu Gln Glu Asp Thr Val Arg Arg
                        245                 250                 255

Lys Lys Cys Pro Phe Gln Ser Trp Pro Glu Ala Tyr Gly Ser Asp Phe
                        260                 265                 270

Trp Lys Ser Val His Phe Thr Asp Tyr Ser Gln His Thr Gln Met Val
                        275                 280                 285

Met Ala Leu Thr Leu Arg Cys Pro Leu Lys Leu Glu Ala Ala Leu Cys
        290                 295                 300

Gln Arg His Asp Trp His Thr Leu Cys Lys Asp Leu Pro Asn Ala Thr
        305                 310                 315                 320

Ala Arg Glu Ser Asp Gly Trp Tyr Val Leu Glu Lys Val Asp Leu His
                        325                 330                 335

Pro Gln Leu Cys Phe Lys Phe Ser Phe Gly Asn Ser Ser His Val Glu
                        340                 345                 350

Cys Pro His Gln Thr Gly Ser Leu Thr Ser Trp Asn Val Ser Met Asp
                        355                 360                 365

Thr Gln Ala Gln Gln Leu Ile Leu His Phe Ser Ser Arg Met His Ala
                        370                 375                 380

Thr Phe Ser Ala Ala Trp Ser Leu Pro Gly Leu Gly Gln Asp Thr Leu
        385                 390                 395                 400

Val Pro Pro Val Tyr Thr Val Ser Gln Ala Arg Gly Ser Ser Pro Val
                        405                 410                 415

Ser Leu Asp Leu Ile Ile Pro Phe Leu Arg Pro Gly Cys Cys Val Leu
                        420                 425                 430

Val Trp Arg Ser Asp Val Gln Phe Ala Trp Lys His Leu Leu Cys Pro
                        435                 440                 445

Asp Val Ser Tyr Arg His Leu Gly Leu Leu Ile Leu Ala Leu Leu Ala
                        450                 455                 460

Leu Leu Thr Leu Leu Gly Val Val Leu Ala Leu Thr Cys Arg Arg Pro
        465                 470                 475                 480

Gln Ser Gly Pro Gly Pro Ala Arg Pro Val Leu Leu Leu His Ala Ala
                        485                 490                 495

Asp Ser Glu Ala Gln Arg Arg Leu Val Gly Ala Leu Ala Glu Leu Leu
                        500                 505                 510

Arg Ala Ala Leu Gly Gly Gly Arg Asp Val Ile Val Asp Leu Trp Glu
                        515                 520                 525

Gly Arg His Val Ala Arg Val Gly Pro Leu Pro Trp Leu Trp Ala Ala
                        530                 535                 540

Arg Thr Arg Val Ala Arg Glu Gln Gly Thr Val Leu Leu Leu Trp Ser
        545                 550                 555                 560

Gly Ala Asp Leu Arg Pro Val Ser Gly Pro Asp Pro Arg Ala Ala Pro
                        565                 570                 575
```

```
Leu Leu Ala Leu Leu His Ala Ala Pro Arg Pro Leu Leu Leu Leu Ala
            580                 585                 590

Tyr Phe Ser Arg Leu Cys Ala Lys Gly Asp Ile Pro Pro Pro Leu Arg
        595                 600                 605

Ala Leu Pro Arg Tyr Arg Leu Leu Arg Asp Leu Pro Arg Leu Leu Arg
    610                 615                 620

Ala Leu Asp Ala Arg Pro Phe Ala Glu Ala Thr Ser Trp Gly Arg Leu
625                 630                 635                 640

Gly Ala Arg Gln Arg Arg Gln Ser Arg Leu Glu Leu Cys Ser Arg Leu
                645                 650                 655

Glu Arg Glu Ala Ala Arg Leu Ala Asp Leu Gly
            660                 665

<210> SEQ ID NO 11
<211> LENGTH: 629
<212> TYPE: PRT
<213> ORGANISM: Homo sapiens

<400> SEQUENCE: 11

Met Asn Gln Val Thr Ile Gln Trp Asp Ala Val Ile Ala Leu Tyr Ile
1               5                   10                  15

Leu Phe Ser Trp Cys His Gly Gly Ile Thr Asn Ile Asn Cys Ser Gly
            20                  25                  30

His Ile Trp Val Glu Pro Ala Thr Ile Phe Lys Met Gly Met Asn Ile
        35                  40                  45

Ser Ile Tyr Cys Gln Ala Ala Ile Lys Asn Cys Gln Pro Arg Lys Leu
50                  55                  60

His Phe Tyr Lys Asn Gly Ile Lys Glu Arg Phe Gln Ile Thr Arg Ile
65                  70                  75                  80

Asn Lys Thr Thr Ala Arg Leu Trp Tyr Lys Asn Phe Leu Glu Pro His
                85                  90                  95

Ala Ser Met Tyr Cys Thr Ala Glu Cys Pro Lys His Phe Gln Glu Thr
            100                 105                 110

Leu Ile Cys Gly Lys Asp Ile Ser Ser Gly Tyr Pro Pro Asp Ile Pro
        115                 120                 125

Asp Glu Val Thr Cys Val Ile Tyr Glu Tyr Ser Gly Asn Met Thr Cys
    130                 135                 140

Thr Trp Asn Ala Gly Lys Leu Thr Tyr Ile Asp Thr Lys Tyr Val Val
145                 150                 155                 160

His Val Lys Ser Leu Glu Thr Glu Glu Gln Gln Tyr Leu Thr Ser Ser
                165                 170                 175

Ser Tyr Ile Asn Ile Ser Thr Asp Ser Leu Gln Gly Gly Lys Lys Tyr
            180                 185                 190

Leu Val Trp Val Gln Ala Ala Asn Ala Leu Gly Met Glu Glu Ser Lys
        195                 200                 205

Gln Leu Gln Ile His Leu Asp Asp Ile Val Ile Pro Ser Ala Ala Val
    210                 215                 220

Ile Ser Arg Ala Glu Thr Ile Asn Ala Thr Val Pro Lys Thr Ile Ile
225                 230                 235                 240

Tyr Trp Asp Ser Gln Thr Thr Ile Glu Lys Val Ser Cys Glu Met Arg
                245                 250                 255

Tyr Lys Ala Thr Thr Asn Gln Thr Trp Asn Val Lys Glu Phe Asp Thr
            260                 265                 270

Asn Phe Thr Tyr Val Gln Gln Ser Glu Phe Tyr Leu Glu Pro Asn Ile
```

```
                275                 280                 285
Lys Tyr Val Phe Gln Val Arg Cys Gln Glu Thr Gly Lys Arg Tyr Trp
            290                 295                 300
Gln Pro Trp Ser Ser Leu Phe Phe His Lys Thr Pro Glu Thr Val Pro
305                 310                 315                 320
Gln Val Thr Ser Lys Ala Phe Gln His Asp Thr Trp Asn Ser Gly Leu
            325                 330                 335
Thr Val Ala Ser Ile Ser Thr Gly His Leu Thr Ser Asp Asn Arg Gly
            340                 345                 350
Asp Ile Gly Leu Leu Gly Met Ile Val Phe Ala Val Met Leu Ser
            355                 360                 365
Ile Leu Ser Leu Ile Gly Ile Phe Asn Arg Ser Phe Arg Thr Gly Ile
370                 375                 380
Lys Arg Arg Ile Leu Leu Leu Ile Pro Lys Trp Leu Tyr Glu Asp Ile
385                 390                 395                 400
Pro Asn Met Lys Asn Ser Asn Val Val Lys Met Leu Gln Glu Asn Ser
            405                 410                 415
Glu Leu Met Asn Asn Asn Ser Ser Glu Gln Val Leu Tyr Val Asp Pro
            420                 425                 430
Met Ile Thr Glu Ile Lys Glu Ile Phe Ile Pro Glu His Lys Pro Thr
            435                 440                 445
Asp Tyr Lys Lys Glu Asn Thr Gly Pro Leu Glu Thr Arg Asp Tyr Pro
            450                 455                 460
Gln Asn Ser Leu Phe Asp Asn Thr Thr Val Val Tyr Ile Pro Asp Leu
465                 470                 475                 480
Asn Thr Gly Tyr Lys Pro Gln Ile Ser Asn Phe Leu Pro Glu Gly Ser
            485                 490                 495
His Leu Ser Asn Asn Asn Glu Ile Thr Ser Leu Thr Leu Lys Pro Pro
            500                 505                 510
Val Asp Ser Leu Asp Ser Gly Asn Asn Pro Arg Leu Gln Lys His Pro
            515                 520                 525
Asn Phe Ala Phe Ser Val Ser Ser Val Asn Ser Leu Ser Asn Thr Ile
            530                 535                 540
Phe Leu Gly Glu Leu Ser Leu Ile Leu Asn Gln Gly Glu Cys Ser Ser
545                 550                 555                 560
Pro Asp Ile Gln Asn Ser Val Glu Glu Thr Thr Met Leu Leu Glu
            565                 570                 575
Asn Asp Ser Pro Ser Glu Thr Ile Pro Glu Gln Thr Leu Leu Pro Asp
            580                 585                 590
Glu Phe Val Ser Cys Leu Gly Ile Val Asn Glu Glu Leu Pro Ser Ile
            595                 600                 605
Asn Thr Tyr Phe Pro Gln Asn Ile Leu Glu Ser His Phe Asn Arg Ile
            610                 615                 620
Ser Leu Leu Glu Lys
625

<210> SEQ ID NO 12
<211> LENGTH: 228
<212> TYPE: PRT
<213> ORGANISM: Homo sapiens

<400> SEQUENCE: 12

Met Pro Val Lys Gly Gly Thr Lys Cys Ile Lys Tyr Leu Leu Phe Gly
1               5                   10                  15
```

```
Phe Asn Phe Ile Phe Trp Leu Ala Gly Ile Ala Val Leu Ala Ile Gly
             20                  25                  30

Leu Trp Leu Arg Phe Asp Ser Gln Thr Lys Ser Ile Phe Glu Gln Glu
         35                  40                  45

Thr Asn Asn Asn Ser Ser Phe Tyr Thr Gly Val Tyr Ile Leu Ile
 50                  55                  60

Gly Ala Gly Ala Leu Met Met Leu Val Gly Phe Leu Gly Cys Cys Gly
 65                  70                  75                  80

Ala Val Gln Glu Ser Gln Cys Met Leu Gly Leu Phe Phe Gly Phe Leu
                 85                  90                  95

Leu Val Ile Phe Ala Ile Glu Ile Ala Ala Ala Ile Trp Gly Tyr Ser
                 100                 105                 110

His Lys Asp Glu Val Ile Lys Glu Val Gln Glu Phe Tyr Lys Asp Thr
             115                 120                 125

Tyr Asn Lys Leu Lys Thr Lys Asp Glu Pro Gln Arg Glu Thr Leu Lys
 130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                 165                 170                 175

Thr Val Lys Ser Cys Pro Asp Ala Ile Lys Glu Val Phe Asp Asn Lys
             180                 185                 190

Phe His Ile Ile Gly Ala Val Gly Ile Gly Ile Ala Val Val Met Ile
 195                 200                 205

Phe Gly Met Ile Phe Ser Met Ile Leu Cys Cys Ala Ile Arg Arg Asn
 210                 215                 220

Arg Glu Met Val
225

<210> SEQ ID NO 13
<211> LENGTH: 236
<212> TYPE: PRT
<213> ORGANISM: Homo sapiens

<400> SEQUENCE: 13

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
             20                  25                  30

Leu Trp Leu Arg His Asp Pro Gln Thr Thr Asn Leu Leu Tyr Leu Glu
         35                  40                  45

Leu Gly Asp Lys Pro Ala Pro Asn Thr Phe Tyr Val Gly Ile Tyr Ile
 50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                 85                  90                  95

Cys Leu Val Ile Leu Phe Ala Cys Glu Val Ala Ala Gly Ile Trp Gly
                 100                 105                 110

Phe Val Asn Lys Asp Gln Ile Ala Lys Asp Val Lys Gln Phe Tyr Asp
             115                 120                 125

Gln Ala Leu Gln Gln Ala Val Val Asp Asp Asp Ala Asn Asn Ala Lys
 130                 135                 140

Ala Val Val Lys Thr Phe His Glu Thr Leu Asp Cys Cys Gly Ser Ser
145                 150                 155                 160
```

```
Thr Leu Thr Ala Leu Thr Thr Ser Val Leu Lys Asn Asn Leu Cys Pro
                165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235
```

<210> SEQ ID NO 14
<211> LENGTH: 238
<212> TYPE: PRT
<213> ORGANISM: Homo sapiens

<400> SEQUENCE: 14

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Phe Asn Asn Asn Phe Arg Gln Gln Met Glu Asn Tyr Pro Lys
            115                 120                 125

Asn Asn His Thr Ala Ser Ile Leu Asp Arg Met Gln Ala Asp Phe Lys
        130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
            180                 185                 190

Glu Lys Ile Gly Gly Trp Leu Arg Lys Asn Val Leu Val Val Ala Ala
        195                 200                 205

Ala Ala Leu Gly Ile Ala Phe Val Glu Val Leu Gly Ile Val Phe Ala
    210                 215                 220

Cys Cys Leu Val Lys Ser Ile Arg Ser Gly Tyr Glu Val Met
225                 230                 235
```

<210> SEQ ID NO 15
<211> LENGTH: 1106
<212> TYPE: PRT
<213> ORGANISM: Homo sapiens

<400> SEQUENCE: 15

```
Met Arg Leu Pro Gly Ala Met Pro Ala Leu Ala Leu Lys Gly Glu Leu
1               5                   10                  15
```

```
Leu Leu Leu Ser Leu Leu Leu Leu Glu Pro Gln Ile Ser Gln Gly
             20                  25                  30

Leu Val Val Thr Pro Pro Gly Pro Glu Leu Val Leu Asn Val Ser Ser
         35                  40                  45

Thr Phe Val Leu Thr Cys Ser Gly Ser Ala Pro Val Val Trp Glu Arg
50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
             85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
            115                 120                 125

Pro Asn Asp Ala Glu Glu Leu Phe Ile Phe Leu Thr Glu Ile Thr Glu
130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
            165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
            195                 200                 205

Leu Gln Val Ser Ser Ile Asn Val Ser Val Asn Ala Val Gln Thr Val
            210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
            245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
            275                 280                 285

Tyr Thr Cys Asn Val Thr Glu Ser Val Asn Asp His Gln Asp Glu Lys
            290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
            325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
            355                 360                 365

Thr Arg Asn Val Ser Glu Thr Arg Tyr Val Ser Glu Leu Thr Leu Val
            370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
            405                 410                 415

Val Arg Val Leu Glu Leu Ser Glu Ser His Pro Asp Ser Gly Glu Gln
            420                 425                 430
```

-continued

Thr Val Arg Cys Arg Gly Arg Gly Met Pro Gln Pro Asn Ile Ile Trp
            435                 440                 445

Ser Ala Cys Arg Asp Leu Lys Arg Cys Pro Arg Glu Leu Pro Pro Thr
450                 455                 460

Leu Leu Gly Asn Ser Ser Glu Glu Ser Gln Leu Glu Thr Asn Val
465                 470                 475                 480

Thr Tyr Trp Glu Glu Gln Glu Phe Glu Val Val Ser Thr Leu Arg
            485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
            515                 520                 525

Pro Phe Lys Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
            565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
            595                 600                 605

Gly Ala Phe Gly Gln Val Val Glu Ala Thr Ala His Gly Leu Ser His
            610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
            645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
            675                 680                 685

Leu Val Asp Tyr Leu His Arg Asn Lys His Thr Phe Leu Gln His His
            690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
            725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
            755                 760                 765

Ser Asn Tyr Met Ala Pro Tyr Asp Asn Tyr Val Pro Ser Ala Pro Glu
770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
            805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
            835                 840                 845

Arg Asp Ile Met Arg Asp Ser Asn Tyr Ile Ser Lys Gly Ser Thr Phe

```
                850              855             860
Leu Pro Leu Lys Trp Met Ala Pro Glu Ser Ile Phe Asn Ser Leu Tyr
865             870             875             880

Thr Thr Leu Ser Asp Val Trp Ser Phe Gly Ile Leu Leu Trp Glu Ile
            885             890             895

Phe Thr Leu Gly Gly Thr Pro Tyr Pro Glu Leu Pro Met Asn Glu Gln
            900             905             910

Phe Tyr Asn Ala Ile Lys Arg Gly Tyr Arg Met Ala Gln Pro Ala His
            915             920             925

Ala Ser Asp Glu Ile Tyr Glu Ile Met Gln Lys Cys Trp Glu Glu Lys
        930             935             940

Phe Glu Ile Arg Pro Pro Phe Ser Gln Leu Val Leu Leu Leu Glu Arg
945             950             955             960

Leu Leu Gly Glu Gly Tyr Lys Lys Lys Tyr Gln Gln Val Asp Glu Glu
            965             970             975

Phe Leu Arg Ser Asp His Pro Ala Ile Leu Arg Ser Gln Ala Arg Leu
            980             985             990

Pro Gly Phe His Gly Leu Arg Ser Pro Leu Asp Thr Ser Ser Val Leu
            995             1000            1005

Tyr Thr Ala Val Gln Pro Asn Glu Gly Asp Asn Asp Tyr Ile Ile
        1010            1015            1020

Pro Leu Pro Asp Pro Lys Pro Glu Val Ala Asp Glu Gly Pro Leu
        1025            1030            1035

Glu Gly Ser Pro Ser Leu Ala Ser Ser Thr Leu Asn Glu Val Asn
        1040            1045            1050

Thr Ser Ser Thr Ile Ser Cys Asp Ser Pro Leu Glu Pro Gln Asp
        1055            1060            1065

Glu Pro Glu Pro Glu Pro Gln Leu Glu Leu Gln Val Glu Pro Glu
        1070            1075            1080

Pro Glu Leu Glu Gln Leu Pro Asp Ser Gly Cys Pro Ala Pro Arg
        1085            1090            1095

Ala Glu Ala Glu Asp Ser Phe Leu
        1100            1105

<210> SEQ ID NO 16
<211> LENGTH: 1089
<212> TYPE: PRT
<213> ORGANISM: Homo sapiens

<400> SEQUENCE: 16

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110
```

-continued

Glu Gly Arg His Ile Tyr Ile Tyr Val Pro Asp Pro Asp Val Ala Phe
            115                 120                 125

Val Pro Leu Gly Met Thr Asp Tyr Leu Val Ile Val Glu Asp Asp
130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Pro Arg Ile Ser Trp Leu Lys Asn
            340                 345                 350

Asn Leu Thr Leu Ile Glu Asn Leu Thr Glu Ile Thr Thr Asp Val Glu
        355                 360                 365

Lys Ile Gln Glu Ile Arg Tyr Arg Ser Lys Leu Lys Leu Ile Arg Ala
    370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
    450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val

```
            530                 535                 540
Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                    565                 570                 575

Pro Met Gln Leu Pro Tyr Asp Ser Arg Trp Glu Phe Pro Arg Asp Gly
                580                 585                 590

Leu Val Leu Gly Arg Val Leu Gly Ser Gly Ala Phe Gly Lys Val Val
            595                 600                 605

Glu Gly Thr Ala Tyr Gly Leu Ser Arg Ser Gln Pro Val Met Lys Val
        610                 615                 620

Ala Val Lys Met Leu Lys Pro Thr Ala Arg Ser Ser Glu Lys Gln Ala
625                 630                 635                 640

Leu Met Ser Glu Leu Lys Ile Met Thr His Leu Gly Pro His Leu Asn
                    645                 650                 655

Ile Val Asn Leu Leu Gly Ala Cys Thr Lys Ser Gly Pro Ile Tyr Ile
                660                 665                 670

Ile Thr Glu Tyr Cys Phe Tyr Gly Asp Leu Val Asn Tyr Leu His Lys
            675                 680                 685

Asn Arg Asp Ser Phe Leu Ser His His Pro Glu Lys Pro Lys Lys Glu
690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                    725                 730                 735

Ala Asp Thr Thr Gln Tyr Val Pro Met Leu Glu Arg Lys Glu Val Ser
                740                 745                 750

Lys Tyr Ser Asp Ile Gln Arg Ser Leu Tyr Asp Arg Pro Ala Ser Tyr
            755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                    805                 810                 815

Arg Asp Leu Ala Ala Arg Asn Val Leu Leu Ala Gln Gly Lys Ile Val
                820                 825                 830

Lys Ile Cys Asp Phe Gly Leu Ala Arg Asp Ile Met His Asp Ser Asn
            835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                    885                 890                 895

Pro Gly Met Met Val Asp Ser Thr Phe Tyr Asn Lys Ile Lys Ser Gly
                900                 905                 910

Tyr Arg Met Ala Lys Pro Asp His Ala Thr Ser Glu Val Tyr Glu Ile
            915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960
```

```
Ser Tyr Glu Lys Ile His Leu Asp Phe Leu Lys Ser Asp His Pro Ala
            965                 970                 975

Val Ala Arg Met Arg Val Asp Ser Asp Asn Ala Tyr Ile Gly Val Thr
        980                 985                 990

Tyr Lys Asn Glu Glu Asp Lys Leu  Lys Asp Trp Glu Gly  Gly Leu Asp
        995                 1000                1005

Glu Gln  Arg Leu Ser Ala Asp  Ser Gly Tyr Ile Ile  Pro Leu Pro
    1010                1015                1020

Asp Ile  Asp Pro Val Pro Glu  Glu Asp Leu Gly  Lys Arg Asn
    1025                1030                1035

Arg His  Ser Ser Gln Thr Ser  Glu Glu Ser Ala Ile  Glu Thr Gly
    1040                1045                1050

Ser Ser  Ser Ser Thr Phe Ile  Lys Arg Glu Asp Glu  Thr Ile Glu
    1055                1060                1065

Asp Ile  Asp Met Met Asp Asp  Ile Gly Ile Asp Ser  Ser Asp Leu
    1070                1075                1080

Val Glu  Asp Ser Phe Leu
    1085

<210> SEQ ID NO 17
<211> LENGTH: 1356
<212> TYPE: PRT
<213> ORGANISM: Homo sapiens

<400> SEQUENCE: 17

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
```

```
            225                 230                 235                 240
Lys Leu Val Leu Asn Cys Thr Ala Arg Thr Glu Leu Asn Val Gly Ile
                245                 250                 255
Asp Phe Asn Trp Glu Tyr Pro Ser Ser Lys His Gln His Lys Lys Leu
                260                 265                 270
Val Asn Arg Asp Leu Lys Thr Gln Ser Gly Ser Glu Met Lys Lys Phe
                275                 280                 285
Leu Ser Thr Leu Thr Ile Asp Gly Val Thr Arg Ser Asp Gln Gly Leu
            290                 295                 300
Tyr Thr Cys Ala Ala Ser Ser Gly Leu Met Thr Lys Lys Asn Ser Thr
305                 310                 315                 320
Phe Val Arg Val His Glu Lys Pro Phe Val Ala Phe Gly Ser Gly Met
                325                 330                 335
Glu Ser Leu Val Glu Ala Thr Val Gly Glu Arg Val Arg Ile Pro Ala
                340                 345                 350
Lys Tyr Leu Gly Tyr Pro Pro Pro Glu Ile Lys Trp Tyr Lys Asn Gly
                355                 360                 365
Ile Pro Leu Glu Ser Asn His Thr Ile Lys Ala Gly His Val Leu Thr
            370                 375                 380
Ile Met Glu Val Ser Glu Arg Asp Thr Gly Asn Tyr Thr Val Ile Leu
385                 390                 395                 400
Thr Asn Pro Ile Ser Lys Glu Lys Gln Ser His Val Val Ser Leu Val
                405                 410                 415
Val Tyr Val Pro Pro Gln Ile Gly Glu Lys Ser Leu Ile Ser Pro Val
                420                 425                 430
Asp Ser Tyr Gln Tyr Gly Thr Thr Gln Thr Leu Thr Cys Thr Val Tyr
            435                 440                 445
Ala Ile Pro Pro Pro His His Ile His Trp Tyr Trp Gln Leu Glu Glu
            450                 455                 460
Glu Cys Ala Asn Glu Pro Ser Gln Ala Val Ser Val Thr Asn Pro Tyr
465                 470                 475                 480
Pro Cys Glu Glu Trp Arg Ser Val Glu Asp Phe Gln Gly Gly Asn Lys
                485                 490                 495
Ile Glu Val Asn Lys Asn Gln Phe Ala Leu Ile Glu Gly Lys Asn Lys
                500                 505                 510
Thr Val Ser Thr Leu Val Ile Gln Ala Ala Asn Val Ser Ala Leu Tyr
            515                 520                 525
Lys Cys Glu Ala Val Asn Lys Val Gly Arg Gly Glu Arg Val Ile Ser
            530                 535                 540
Phe His Val Thr Arg Gly Pro Glu Ile Thr Leu Gln Pro Asp Met Gln
545                 550                 555                 560
Pro Thr Glu Gln Glu Ser Val Ser Leu Trp Cys Thr Ala Asp Arg Ser
                565                 570                 575
Thr Phe Glu Asn Leu Thr Trp Tyr Lys Leu Gly Pro Gln Pro Leu Pro
                580                 585                 590
Ile His Val Gly Glu Leu Pro Thr Pro Val Cys Lys Asn Leu Asp Thr
            595                 600                 605
Leu Trp Lys Leu Asn Ala Thr Met Phe Ser Asn Ser Thr Asn Asp Ile
            610                 615                 620
Leu Ile Met Glu Leu Lys Asn Ala Ser Leu Gln Asp Gln Gly Asp Tyr
625                 630                 635                 640
Val Cys Leu Ala Gln Asp Arg Lys Thr Lys Lys Arg His Cys Val Val
                645                 650                 655
```

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Gly Leu Tyr Thr
            725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
            755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

-continued

```
Leu Lys Trp Met Ala Pro Glu Thr Ile Phe Asp Arg Val Tyr Thr
    1070                1075                1080

Ile Gln Ser Asp Val Trp Ser Phe Gly Val Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 18
<211> LENGTH: 1210
<212> TYPE: PRT
<213> ORGANISM: Homo sapiens

<400> SEQUENCE: 18

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60
```

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
        210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Lys Asn Leu Cys Tyr Ala Asn Thr Ile Asn Trp Lys Lys Leu
465                 470                 475                 480
```

```
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
            660                 665                 670
Ile Val Arg Lys Arg Thr Leu Arg Arg Leu Leu Gln Glu Arg Glu Leu
        675                 680                 685
Val Glu Pro Leu Thr Pro Ser Gly Glu Ala Pro Asn Gln Ala Leu Leu
    690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
            740                 745                 750
Pro Lys Ala Asn Lys Glu Ile Leu Asp Glu Ala Tyr Val Met Ala Ser
        755                 760                 765
Val Asp Asn Pro His Val Cys Arg Leu Leu Gly Ile Cys Leu Thr Ser
    770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
        835                 840                 845
Gln His Val Lys Ile Thr Asp Phe Gly Leu Ala Lys Leu Leu Gly Ala
    850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
```

```
                900             905             910
Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
            930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
        1130                1135                1140

Pro Thr Cys Val Asn Ser Thr Phe Asp Ser Pro Ala His Trp Ala
        1145                1150                1155

Gln Lys Gly Ser His Gln Ile Ser Leu Asp Asn Pro Asp Tyr Gln
        1160                1165                1170

Gln Asp Phe Phe Pro Lys Glu Ala Lys Pro Asn Gly Ile Phe Lys
        1175                1180                1185

Gly Ser Thr Ala Glu Asn Ala Glu Tyr Leu Arg Val Ala Pro Gln
        1190                1195                1200

Ser Ser Glu Phe Ile Gly Ala
        1205                1210

<210> SEQ ID NO 19
<211> LENGTH: 610
<212> TYPE: PRT
<213> ORGANISM: Homo sapiens

<400> SEQUENCE: 19

Met Ile Ala Ser Gln Phe Leu Ser Ala Leu Thr Leu Val Leu Leu Ile
1               5                   10                  15

Lys Glu Ser Gly Ala Trp Ser Tyr Asn Thr Ser Thr Glu Ala Met Thr
            20                  25                  30

Tyr Asp Glu Ala Ser Ala Tyr Cys Gln Gln Arg Tyr Thr His Leu Val
        35                  40                  45
```

-continued

```
Ala Ile Gln Asn Lys Glu Glu Ile Glu Tyr Leu Asn Ser Ile Leu Ser
 50                  55                  60

Tyr Ser Pro Ser Tyr Tyr Trp Ile Gly Ile Arg Lys Val Asn Asn Val
 65                  70                  75                  80

Trp Val Trp Val Gly Thr Gln Lys Pro Leu Thr Glu Glu Ala Lys Asn
                 85                  90                  95

Trp Ala Pro Gly Glu Pro Asn Asn Arg Gln Lys Asp Glu Asp Cys Val
                100                 105                 110

Glu Ile Tyr Ile Lys Arg Glu Lys Asp Val Gly Met Trp Asn Asp Glu
            115                 120                 125

Arg Cys Ser Lys Lys Lys Leu Ala Leu Cys Tyr Thr Ala Ala Cys Thr
130                 135                 140

Asn Thr Ser Cys Ser Gly His Gly Glu Cys Val Glu Thr Ile Asn Asn
145                 150                 155                 160

Tyr Thr Cys Lys Cys Asp Pro Gly Phe Ser Gly Leu Lys Cys Glu Gln
                165                 170                 175

Ile Val Asn Cys Thr Ala Leu Glu Ser Pro Glu His Gly Ser Leu Val
            180                 185                 190

Cys Ser His Pro Leu Gly Asn Phe Ser Tyr Asn Ser Ser Cys Ser Ile
        195                 200                 205

Ser Cys Asp Arg Gly Tyr Leu Pro Ser Ser Met Glu Thr Met Gln Cys
    210                 215                 220

Met Ser Ser Gly Glu Trp Ser Ala Pro Ile Pro Ala Cys Asn Val Val
225                 230                 235                 240

Glu Cys Asp Ala Val Thr Asn Pro Ala Asn Gly Phe Val Glu Cys Phe
                245                 250                 255

Gln Asn Pro Gly Ser Phe Pro Trp Asn Thr Thr Cys Thr Phe Asp Cys
            260                 265                 270

Glu Glu Gly Phe Glu Leu Met Gly Ala Gln Ser Leu Gln Cys Thr Ser
        275                 280                 285

Ser Gly Asn Trp Asp Asn Glu Lys Pro Thr Cys Lys Ala Val Thr Cys
    290                 295                 300

Arg Ala Val Arg Gln Pro Gln Asn Gly Ser Val Arg Cys Ser His Ser
305                 310                 315                 320

Pro Ala Gly Glu Phe Thr Phe Lys Ser Ser Cys Asn Phe Thr Cys Glu
                325                 330                 335

Glu Gly Phe Met Leu Gln Gly Pro Ala Gln Val Glu Cys Thr Thr Gln
            340                 345                 350

Gly Gln Trp Thr Gln Gln Ile Pro Val Cys Glu Ala Phe Gln Cys Thr
        355                 360                 365

Ala Leu Ser Asn Pro Glu Arg Gly Tyr Met Asn Cys Leu Pro Ser Ala
    370                 375                 380

Ser Gly Ser Phe Arg Tyr Gly Ser Ser Cys Glu Phe Ser Cys Glu Gln
385                 390                 395                 400

Gly Phe Val Leu Lys Gly Ser Lys Arg Leu Gln Cys Gly Pro Thr Gly
                405                 410                 415

Glu Trp Asp Asn Glu Lys Pro Thr Cys Glu Ala Val Arg Cys Asp Ala
            420                 425                 430

Val His Gln Pro Pro Lys Gly Leu Val Arg Cys Ala His Ser Pro Ile
        435                 440                 445

Gly Glu Phe Thr Tyr Lys Ser Ser Cys Ala Phe Ser Cys Glu Glu Gly
    450                 455                 460

Phe Glu Leu His Gly Ser Thr Gln Leu Glu Cys Thr Ser Gln Gly Gln
```

```
            465                 470                 475                 480
Trp Thr Glu Glu Val Pro Ser Cys Gln Val Lys Cys Ser Ser Leu
                485                 490                 495

Ala Val Pro Gly Lys Ile Asn Met Ser Cys Ser Gly Glu Pro Val Phe
                500                 505                 510

Gly Thr Val Cys Lys Phe Ala Cys Pro Glu Gly Trp Thr Leu Asn Gly
                515                 520                 525

Ser Ala Ala Arg Thr Cys Gly Ala Thr Gly His Trp Ser Gly Leu Leu
                530                 535                 540

Pro Thr Cys Glu Ala Pro Thr Glu Ser Asn Ile Pro Leu Val Ala Gly
545                 550                 555                 560

Leu Ser Ala Ala Gly Leu Ser Leu Leu Thr Leu Ala Pro Phe Leu Leu
                565                 570                 575

Trp Leu Arg Lys Cys Leu Arg Lys Ala Lys Lys Phe Val Pro Ala Ser
                580                 585                 590

Ser Cys Gln Ser Leu Glu Ser Asp Gly Ser Tyr Gln Lys Pro Ser Tyr
                595                 600                 605

Ile Leu
    610

<210> SEQ ID NO 20
<211> LENGTH: 830
<212> TYPE: PRT
<213> ORGANISM: Homo sapiens

<400> SEQUENCE: 20

Met Ala Asn Cys Gln Ile Ala Ile Leu Tyr Gln Arg Phe Gln Arg Val
1               5                   10                  15

Val Phe Gly Ile Ser Gln Leu Leu Cys Phe Ser Ala Leu Ile Ser Glu
                20                  25                  30

Leu Thr Asn Gln Lys Glu Val Ala Ala Trp Thr Tyr His Tyr Ser Thr
                35                  40                  45

Lys Ala Tyr Ser Trp Asn Ile Ser Arg Lys Tyr Cys Gln Asn Arg Tyr
            50                  55                  60

Thr Asp Leu Val Ala Ile Gln Asn Lys Asn Glu Ile Asp Tyr Leu Asn
65                  70                  75                  80

Lys Val Leu Pro Tyr Tyr Ser Ser Tyr Tyr Trp Ile Gly Ile Arg Lys
                85                  90                  95

Asn Asn Lys Thr Trp Thr Trp Val Gly Thr Lys Lys Ala Leu Thr Asn
                100                 105                 110

Glu Ala Glu Asn Trp Ala Asp Asn Glu Pro Asn Asn Lys Arg Asn Asn
                115                 120                 125

Glu Asp Cys Val Glu Ile Tyr Ile Lys Ser Pro Ser Ala Pro Gly Lys
            130                 135                 140

Trp Asn Asp Glu His Cys Leu Lys Lys His Ala Leu Cys Tyr Thr
145                 150                 155                 160

Ala Ser Cys Gln Asp Met Ser Cys Ser Lys Gln Gly Glu Cys Leu Glu
                165                 170                 175

Thr Ile Gly Asn Tyr Thr Cys Ser Cys Tyr Pro Gly Phe Tyr Gly Pro
                180                 185                 190

Glu Cys Glu Tyr Val Arg Glu Cys Gly Glu Leu Glu Leu Pro Gln His
                195                 200                 205

Val Leu Met Asn Cys Ser His Pro Leu Gly Asn Phe Ser Phe Asn Ser
                210                 215                 220
```

```
-continued

Gln Cys Ser Phe His Cys Thr Asp Gly Tyr Gln Val Asn Gly Pro Ser
225                 230                 235                 240

Lys Leu Glu Cys Leu Ala Ser Gly Ile Trp Thr Asn Lys Pro Pro Gln
                245                 250                 255

Cys Leu Ala Ala Gln Cys Pro Pro Leu Lys Ile Pro Glu Arg Gly Asn
                260                 265                 270

Met Thr Cys Leu His Ser Ala Lys Ala Phe Gln His Gln Ser Ser Cys
            275                 280                 285

Ser Phe Ser Cys Glu Glu Gly Phe Ala Leu Val Gly Pro Glu Val Val
            290                 295                 300

Gln Cys Thr Ala Ser Gly Val Trp Thr Ala Pro Ala Pro Val Cys Lys
305                 310                 315                 320

Ala Val Gln Cys Gln His Leu Glu Ala Pro Ser Glu Gly Thr Met Asp
                325                 330                 335

Cys Val His Pro Leu Thr Ala Phe Ala Tyr Gly Ser Ser Cys Lys Phe
                340                 345                 350

Glu Cys Gln Pro Gly Tyr Arg Val Arg Gly Leu Asp Met Leu Arg Cys
            355                 360                 365

Ile Asp Ser Gly His Trp Ser Ala Pro Leu Pro Thr Cys Glu Ala Ile
370                 375                 380

Ser Cys Glu Pro Leu Glu Ser Pro Val His Gly Ser Met Asp Cys Ser
385                 390                 395                 400

Pro Ser Leu Arg Ala Phe Gln Tyr Asp Thr Asn Cys Ser Phe Arg Cys
                405                 410                 415

Ala Glu Gly Phe Met Leu Arg Gly Ala Asp Ile Val Arg Cys Asp Asn
                420                 425                 430

Leu Gly Gln Trp Thr Ala Pro Ala Pro Val Cys Gln Ala Leu Gln Cys
            435                 440                 445

Gln Asp Leu Pro Val Pro Asn Glu Ala Arg Val Asn Cys Ser His Pro
450                 455                 460

Phe Gly Ala Phe Arg Tyr Gln Ser Val Cys Ser Phe Thr Cys Asn Glu
465                 470                 475                 480

Gly Leu Leu Leu Val Gly Ala Ser Val Leu Gln Cys Leu Ala Thr Gly
                485                 490                 495

Asn Trp Asn Ser Val Pro Pro Glu Cys Gln Ala Ile Pro Cys Thr Pro
            500                 505                 510

Leu Leu Ser Pro Gln Asn Gly Thr Met Thr Cys Val Gln Pro Leu Gly
            515                 520                 525

Ser Ser Tyr Lys Ser Thr Cys Gln Phe Ile Cys Asp Glu Gly Tyr
530                 535                 540

Ser Leu Ser Gly Pro Glu Arg Leu Asp Cys Thr Arg Ser Gly Arg Trp
545                 550                 555                 560

Thr Asp Ser Pro Pro Met Cys Glu Ala Ile Lys Cys Pro Glu Leu Phe
                565                 570                 575

Ala Pro Glu Gln Gly Ser Leu Asp Cys Ser Asp Thr Arg Gly Glu Phe
                580                 585                 590

Asn Val Gly Ser Thr Cys His Phe Ser Cys Asp Asn Gly Phe Lys Leu
                595                 600                 605

Glu Gly Pro Asn Asn Val Glu Cys Thr Thr Ser Gly Arg Trp Ser Ala
            610                 615                 620

Thr Pro Pro Thr Cys Lys Gly Ile Ala Ser Leu Pro Thr Pro Gly Val
625                 630                 635                 640

Gln Cys Pro Ala Leu Thr Thr Pro Gly Gln Gly Thr Met Tyr Cys Arg
```

His His Pro Gly Thr Phe Gly Phe Asn Thr Thr Cys Tyr Phe Gly Cys
              645                 650                 655

Asn Ala Gly Phe Thr Leu Ile Gly Asp Ser Thr Leu Ser Cys Arg Pro
        660                 665                 670

Ser Gly Gln Trp Thr Ala Val Thr Pro Ala Cys Arg Ala Val Lys Cys
    675                 680                 685

Ser Glu Leu His Val Asn Lys Pro Ile Ala Met Asn Cys Ser Asn Leu
690                 695                 700

Trp Gly Asn Phe Ser Tyr Gly Ser Ile Cys Ser Phe His Cys Leu Glu
705                 710                 715                 720

Gly Gln Leu Leu Asn Gly Ser Ala Gln Thr Ala Cys Gln Glu Asn Gly
        725                 730                 735

His Trp Ser Thr Thr Val Pro Thr Cys Gln Ala Gly Pro Leu Thr Ile
            740                 745                 750

Gln Glu Ala Leu Thr Tyr Phe Gly Gly Ala Val Ala Ser Thr Ile Gly
                755                 760                 765

Leu Ile Met Gly Gly Thr Leu Leu Ala Leu Leu Arg Lys Arg Phe Arg
770                 775                 780

Gln Lys Asp Asp Gly Lys Cys Pro Leu Asn Pro His Ser His Leu Gly
785                 790                 795                 800

Thr Tyr Gly Val Phe Thr Asn Ala Ala Phe Asp Pro Ser Pro
        805                 810                 815

820                 825                 830

<210> SEQ ID NO 21
<211> LENGTH: 385
<212> TYPE: PRT
<213> ORGANISM: Homo sapiens

<400> SEQUENCE: 21

Met Gly Cys Arg Arg Thr Arg Glu Gly Pro Ser Lys Ala Met Ile Phe
1               5                   10                  15

Pro Trp Lys Cys Gln Ser Thr Gln Arg Asp Leu Trp Asn Ile Phe Lys
            20                  25                  30

Leu Trp Gly Trp Thr Met Leu Cys Cys Asp Phe Leu Ala His His Gly
        35                  40                  45

Thr Asp Cys Trp Thr Tyr His Tyr Ser Glu Lys Pro Met Asn Trp Gln
    50                  55                  60

Arg Ala Arg Arg Phe Cys Arg Asp Asn Tyr Thr Asp Leu Val Ala Ile
65                  70                  75                  80

Gln Asn Lys Ala Glu Ile Glu Tyr Leu Glu Lys Thr Leu Pro Phe Ser
                85                  90                  95

Arg Ser Tyr Tyr Trp Ile Gly Ile Arg Lys Ile Gly Gly Ile Trp Thr
            100                 105                 110

Trp Val Gly Thr Asn Lys Ser Leu Thr Glu Glu Ala Glu Asn Trp Gly
        115                 120                 125

Asp Gly Glu Pro Asn Asn Lys Lys Asn Lys Glu Asp Cys Val Glu Ile
    130                 135                 140

Tyr Ile Lys Arg Asn Lys Asp Ala Gly Lys Trp Asn Asp Asp Ala Cys
145                 150                 155                 160

His Lys Leu Lys Ala Ala Leu Cys Tyr Thr Ala Ser Cys Gln Pro Trp
                165                 170                 175

Ser Cys Ser Gly His Gly Glu Cys Val Glu Ile Ile Asn Asn Tyr Thr
            180                 185                 190

```
Cys Asn Cys Asp Val Gly Tyr Tyr Gly Pro Gln Cys Gln Phe Val Ile
            195                 200                 205

Gln Cys Glu Pro Leu Glu Ala Pro Glu Leu Gly Thr Met Asp Cys Thr
    210                 215                 220

His Pro Leu Gly Asn Phe Ser Phe Ser Gln Cys Ala Phe Ser Cys
225                 230                 235                 240

Ser Glu Gly Thr Asn Leu Thr Gly Ile Glu Thr Thr Cys Gly Pro
                245                 250                 255

Phe Gly Asn Trp Ser Ser Pro Glu Pro Thr Cys Gln Val Ile Gln Cys
            260                 265                 270

Glu Pro Leu Ser Ala Pro Asp Leu Gly Ile Met Asn Cys Ser His Pro
    275                 280                 285

Leu Ala Ser Phe Ser Phe Thr Ser Ala Cys Thr Phe Ile Cys Ser Glu
    290                 295                 300

Gly Thr Glu Leu Ile Gly Lys Lys Lys Thr Ile Cys Glu Ser Ser Gly
305                 310                 315                 320

Ile Trp Ser Asn Pro Ser Pro Ile Cys Gln Lys Leu Asp Lys Ser Phe
                325                 330                 335

Ser Met Ile Lys Glu Gly Asp Tyr Asn Pro Leu Phe Ile Pro Val Ala
            340                 345                 350

Val Met Val Thr Ala Phe Ser Gly Leu Ala Phe Ile Ile Trp Leu Ala
    355                 360                 365

Arg Arg Leu Lys Lys Gly Lys Lys Ser Lys Arg Ser Met Asn Asp Pro
370                 375                 380

Tyr
385

<210> SEQ ID NO 22
<211> LENGTH: 411
<212> TYPE: PRT
<213> ORGANISM: Homo sapiens

<400> SEQUENCE: 22

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175
```

```
Val Gln Asn Gly Thr Val Ser Thr Asn Glu Phe Leu Cys Asp Lys Asp
                180                 185                 190

Lys Thr Ser Thr Val Ala Pro Thr Ile His Thr Thr Val Pro Ser Pro
            195                 200                 205

Thr Thr Thr Pro Thr Pro Lys Glu Lys Pro Glu Ala Gly Thr Tyr Ser
        210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
290                 295                 300

Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
            325                 330                 335

Val Ser Val Ser Gly Ala Phe Gln Ile Asn Thr Phe Asp Leu Arg Val
        340                 345                 350

Gln Pro Phe Asn Val Thr Gln Gly Lys Tyr Ser Thr Ala Glu Glu Cys
        355                 360                 365

Ser Ala Asp Ser Asp Leu Asn Phe Leu Ile Pro Val Ala Val Gly Val
370                 375                 380

Ala Leu Gly Phe Leu Ile Ile Val Val Phe Ile Ser Tyr Met Ile Gly
385                 390                 395                 400

Arg Arg Lys Ser Arg Thr Gly Tyr Gln Ser Val
                405                 410

<210> SEQ ID NO 23
<211> LENGTH: 310
<212> TYPE: PRT
<213> ORGANISM: Homo sapiens

<400> SEQUENCE: 23

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Thr Ala Thr Thr
```

```
            130                 135                 140
Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 24
<211> LENGTH: 172
<212> TYPE: PRT
<213> ORGANISM: Homo sapiens

<400> SEQUENCE: 24

Met Tyr Leu Asp Asn Ser Ser Ile Glu Glu Ala Ser Gly Val Tyr Pro
1               5                   10                  15

Ile Asp Asp Asp Asp Tyr Ala Ser Ala Ser Gly Ser Gly Ala Asp Glu
                20                  25                  30

Asp Val Glu Ser Pro Glu Leu Thr Thr Ser Arg Pro Leu Pro Lys Ile
            35                  40                  45

Leu Leu Thr Ser Ala Ala Pro Lys Val Glu Thr Thr Thr Leu Asn Ile
        50                  55                  60

Gln Asn Lys Ile Pro Ala Gln Thr Lys Ser Pro Glu Glu Thr Asp Lys
65                  70                  75                  80

Glu Lys Val His Leu Ser Asp Ser Glu Arg Lys Met Asp Pro Ala Glu
                85                  90                  95

Glu Asp Thr Asn Val Tyr Thr Glu Lys His Ser Asp Ser Leu Phe Lys
            100                 105                 110

Arg Thr Glu Val Leu Ala Ala Val Ile Ala Gly Gly Val Ile Gly Phe
        115                 120                 125

Leu Phe Ala Ile Phe Leu Ile Leu Leu Leu Val Tyr Arg Met Arg Lys
    130                 135                 140

Lys Asp Glu Gly Ser Tyr Asp Leu Gly Glu Arg Lys Pro Ser Ser Ala
145                 150                 155                 160

Ala Tyr Gln Lys Ala Pro Thr Lys Glu Phe Tyr Ala
                165                 170

<210> SEQ ID NO 25
<211> LENGTH: 442
```

<212> TYPE: PRT
<213> ORGANISM: Homo sapiens

<400> SEQUENCE: 25

```
Met Lys Pro Gly Pro Pro His Arg Ala Gly Ala His Gly Ala Gly
1               5                   10                  15

Ala Gly Ala Gly Ala Ala Gly Pro Gly Ala Arg Gly Leu Leu Leu
            20                  25                  30

Pro Pro Leu Leu Leu Leu Leu Leu Ala Gly Arg Ala Ala Gly Ala Gln
            35                  40                  45

Arg Trp Arg Ser Glu Asn Phe Glu Arg Pro Val Asp Leu Glu Gly Ser
50                  55                  60

Gly Asp Asp Asp Ser Phe Pro Asp Asp Glu Leu Asp Asp Leu Tyr Ser
65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
            100                 105                 110

Val Leu Pro Thr Thr Asn Ile Gln Pro Val Gly Thr Pro Phe Glu Glu
            115                 120                 125

Leu Pro Ser Glu Arg Pro Thr Leu Glu Pro Ala Thr Ser Pro Leu Val
130                 135                 140

Val Thr Glu Val Pro Glu Pro Ser Gln Arg Ala Thr Thr Val Ser
145                 150                 155                 160

Thr Thr Met Ala Thr Ala Ala Thr Ser Thr Gly Asp Pro Thr Val
                165                 170                 175

Ala Thr Val Pro Ala Thr Val Ala Thr Ala Thr Pro Ser Thr Pro Ala
            180                 185                 190

Ala Pro Pro Phe Thr Ala Thr Thr Ala Val Ile Arg Thr Thr Gly Val
            195                 200                 205

Arg Arg Leu Leu Pro Leu Pro Leu Thr Val Ala Thr Ala Arg Ala
210                 215                 220

Thr Thr Pro Glu Ala Pro Ser Pro Pro Thr Thr Ala Ala Val Leu Asp
225                 230                 235                 240

Thr Glu Ala Pro Thr Pro Arg Leu Val Ser Thr Ala Thr Ser Arg Pro
                245                 250                 255

Arg Ala Leu Pro Arg Pro Ala Thr Thr Gln Glu Pro Asp Ile Pro Glu
            260                 265                 270

Arg Ser Thr Leu Pro Leu Gly Thr Thr Ala Pro Gly Pro Thr Glu Val
            275                 280                 285

Ala Gln Thr Pro Thr Pro Glu Thr Phe Leu Thr Thr Ile Arg Asp Glu
290                 295                 300

Pro Glu Val Pro Val Ser Gly Gly Pro Ser Gly Asp Phe Glu Leu Pro
305                 310                 315                 320

Glu Glu Glu Thr Thr Gln Pro Asp Thr Ala Asn Glu Val Val Ala Val
                325                 330                 335

Gly Gly Ala Ala Ala Lys Ala Ser Ser Pro Pro Gly Thr Leu Pro Lys
            340                 345                 350

Gly Ala Arg Pro Gly Pro Gly Leu Leu Asp Asn Ala Ile Asp Ser Gly
            355                 360                 365

Ser Ser Ala Ala Gln Leu Pro Gln Lys Ser Ile Leu Glu Arg Lys Glu
370                 375                 380

Val Leu Val Ala Val Ile Val Gly Gly Val Val Gly Ala Leu Phe Ala
385                 390                 395                 400
```

```
Ala Phe Leu Val Thr Leu Leu Ile Tyr Arg Met Lys Lys Asp Glu
            405                 410                 415

Gly Ser Tyr Thr Leu Glu Glu Pro Lys Gln Ala Ser Val Thr Tyr Gln
            420                 425                 430

Lys Pro Asp Lys Gln Glu Glu Phe Tyr Ala
            435                 440

<210> SEQ ID NO 26
<211> LENGTH: 198
<212> TYPE: PRT
<213> ORGANISM: Homo sapiens

<400> SEQUENCE: 26

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
130                 135                 140

Glu Val Leu Ala Ala Leu Ile Val Gly Gly Ile Val Gly Ile Leu Phe
145                 150                 155                 160

Ala Val Phe Leu Ile Leu Leu Leu Met Tyr Arg Met Lys Lys Lys Asp
                165                 170                 175

Glu Gly Ser Tyr Asp Leu Gly Lys Lys Pro Ile Tyr Lys Lys Ala Pro
            180                 185                 190

Thr Asn Glu Phe Tyr Ala
            195

<210> SEQ ID NO 27
<211> LENGTH: 419
<212> TYPE: PRT
<213> ORGANISM: Homo sapiens

<400> SEQUENCE: 27

Met Arg Asn Ile Phe Lys Arg Asn Gln Glu Pro Ile Val Ala Pro Ala
1               5                   10                  15

Thr Thr Thr Ala Thr Met Pro Ile Gly Pro Val Asp Asn Ser Thr Glu
            20                  25                  30

Ser Gly Gly Ala Gly Glu Ser Gln Glu Asp Met Phe Ala Lys Leu Lys
        35                  40                  45

Glu Lys Leu Phe Asn Glu Ile Asn Lys Ile Pro Leu Pro Pro Trp Ala
    50                  55                  60

Leu Ile Ala Ile Ala Val Val Ala Gly Leu Leu Leu Leu Thr Cys Cys
65                  70                  75                  80
```

Phe Cys Ile Cys Lys Lys Cys Cys Lys Lys Lys Asn Lys Lys
                85                  90                  95

Glu Lys Gly Lys Gly Met Lys Asn Ala Met Asn Met Lys Asp Met Lys
            100                 105                 110

Gly Gly Gln Asp Asp Asp Ala Glu Thr Gly Leu Thr Glu Gly Glu
        115                 120                 125

Gly Glu Gly Glu Glu Lys Glu Pro Glu Asn Leu Gly Lys Leu Gln
130                 135                 140

Phe Ser Leu Asp Tyr Asp Phe Gln Ala Asn Gln Leu Thr Val Gly Val
145                 150                 155                 160

Leu Gln Ala Ala Glu Leu Pro Ala Leu Asp Met Gly Gly Thr Ser Asp
                165                 170                 175

Pro Tyr Val Lys Val Phe Leu Leu Pro Asp Lys Lys Lys Lys Tyr Glu
                180                 185                 190

Thr Lys Val His Arg Lys Thr Leu Asn Pro Ala Phe Asn Glu Thr Phe
                195                 200                 205

Thr Phe Lys Val Pro Tyr Gln Glu Leu Gly Gly Lys Thr Leu Val Met
        210                 215                 220

Ala Ile Tyr Asp Phe Asp Arg Phe Ser Lys His Asp Ile Ile Gly Glu
225                 230                 235                 240

Val Lys Val Pro Met Asn Thr Val Asp Leu Gly Gln Pro Ile Glu Glu
                245                 250                 255

Trp Arg Asp Leu Gln Gly Gly Glu Lys Glu Glu Pro Glu Lys Leu Gly
                260                 265                 270

Asp Ile Cys Thr Ser Leu Arg Tyr Val Pro Thr Ala Gly Lys Leu Thr
                275                 280                 285

Val Cys Ile Leu Glu Ala Lys Asn Leu Lys Lys Met Asp Val Gly Gly
        290                 295                 300

Leu Ser Asp Pro Tyr Val Lys Ile His Leu Met Gln Asn Gly Lys Arg
305                 310                 315                 320

Leu Lys Lys Lys Lys Thr Thr Val Lys Lys Lys Thr Leu Asn Pro Tyr
                325                 330                 335

Phe Asn Glu Ser Phe Ser Phe Glu Ile Pro Phe Glu Gln Ile Gln Lys
                340                 345                 350

Val Gln Val Val Val Thr Val Leu Asp Tyr Asp Lys Leu Gly Lys Asn
        355                 360                 365

Glu Ala Ile Gly Lys Ile Phe Val Gly Ser Asn Ala Thr Gly Thr Glu
        370                 375                 380

Leu Arg His Trp Ser Asp Met Leu Ala Asn Pro Arg Arg Pro Ile Ala
385                 390                 395                 400

Gln Trp His Ser Leu Lys Pro Glu Glu Glu Val Asp Ala Leu Leu Gly
                405                 410                 415

Lys Asn Lys

<210> SEQ ID NO 28
<211> LENGTH: 873
<212> TYPE: PRT
<213> ORGANISM: Homo sapiens

<400> SEQUENCE: 28

Met Ala Thr Phe Ile Ser Val Gln Leu Lys Lys Thr Ser Glu Val Asp
1               5                   10                  15

Leu Ala Lys Pro Leu Val Lys Phe Ile Gln Gln Thr Tyr Pro Ser Gly
            20                  25                  30

```
Gly Glu Glu Gln Ala Gln Tyr Cys Arg Ala Ala Glu Leu Ser Lys
        35                  40                  45

Leu Arg Arg Ala Ala Val Gly Arg Pro Leu Asp Lys His Glu Gly Ala
    50                  55                  60

Leu Glu Thr Leu Leu Arg Tyr Tyr Asp Gln Ile Cys Ser Ile Glu Pro
65                  70                  75                  80

Lys Phe Pro Phe Ser Glu Asn Gln Ile Cys Leu Thr Phe Thr Trp Lys
                85                  90                  95

Asp Ala Phe Asp Lys Gly Ser Leu Phe Gly Gly Ser Val Lys Leu Ala
                100                 105                 110

Leu Ala Ser Leu Gly Tyr Glu Lys Ser Cys Val Leu Phe Asn Cys Ala
            115                 120                 125

Ala Leu Ala Ser Gln Ile Ala Ala Glu Gln Asn Leu Asp Asn Asp Glu
        130                 135                 140

Gly Leu Lys Ile Ala Ala Lys His Tyr Gln Phe Ala Ser Gly Ala Phe
145                 150                 155                 160

Leu His Ile Lys Glu Thr Val Leu Ser Ala Leu Ser Arg Glu Pro Thr
                165                 170                 175

Val Asp Ile Ser Pro Asp Thr Val Gly Thr Leu Ser Leu Ile Met Leu
                180                 185                 190

Ala Gln Ala Gln Glu Val Phe Phe Leu Lys Ala Thr Arg Asp Lys Met
            195                 200                 205

Lys Asp Ala Ile Ile Ala Lys Leu Ala Asn Gln Ala Ala Asp Tyr Phe
        210                 215                 220

Gly Asp Ala Phe Lys Gln Cys Gln Tyr Lys Asp Thr Leu Pro Lys Tyr
225                 230                 235                 240

Phe Tyr Phe Gln Glu Val Phe Pro Val Leu Ala Ala Lys His Cys Ile
                245                 250                 255

Met Gln Ala Asn Ala Glu Tyr His Gln Ser Ile Leu Ala Lys Gln Gln
                260                 265                 270

Lys Lys Phe Gly Glu Glu Ile Ala Arg Leu Gln His Ala Ala Glu Leu
        275                 280                 285

Ile Lys Thr Val Ala Ser Arg Tyr Asp Glu Tyr Val Asn Val Lys Asp
        290                 295                 300

Phe Ser Asp Lys Ile Asn Arg Ala Leu Ala Ala Ala Lys Lys Asp Asn
305                 310                 315                 320

Asp Phe Ile Tyr His Asp Arg Val Pro Asp Leu Lys Asp Leu Asp Pro
                325                 330                 335

Ile Gly Lys Ala Thr Leu Val Lys Ser Thr Pro Val Asn Val Pro Ile
                340                 345                 350

Ser Gln Lys Phe Thr Asp Leu Phe Glu Lys Met Val Pro Val Ser Val
            355                 360                 365

Gln Gln Ser Leu Ala Ala Tyr Asn Gln Arg Lys Ala Asp Leu Val Asn
        370                 375                 380

Arg Ser Ile Ala Gln Met Arg Glu Ala Thr Thr Leu Ala Asn Gly Val
385                 390                 395                 400

Leu Ala Ser Leu Asn Leu Pro Ala Ala Ile Glu Asp Val Ser Gly Asp
                405                 410                 415

Thr Val Pro Gln Ser Ile Leu Thr Lys Ser Arg Ser Val Ile Glu Gln
                420                 425                 430

Gly Gly Ile Gln Thr Val Asp Gln Leu Ile Lys Glu Leu Pro Glu Leu
            435                 440                 445
```

```
Leu Gln Arg Asn Arg Glu Ile Leu Asp Glu Ser Leu Arg Leu Leu Asp
    450                 455                 460
Glu Glu Glu Ala Thr Asp Asn Asp Leu Arg Ala Lys Phe Lys Glu Arg
465                 470                 475                 480
Trp Gln Arg Thr Pro Ser Asn Glu Leu Tyr Lys Pro Leu Arg Ala Glu
                    485                 490                 495
Gly Thr Asn Phe Arg Thr Val Leu Asp Lys Ala Val Gln Ala Asp Gly
                500                 505                 510
Gln Val Lys Glu Cys Tyr Gln Ser His Arg Asp Thr Ile Val Leu Leu
            515                 520                 525
Cys Lys Pro Glu Pro Glu Leu Asn Ala Ala Ile Pro Ser Ala Asn Pro
530                 535                 540
Ala Lys Thr Met Gln Gly Ser Glu Val Val Asn Val Leu Lys Ser Leu
545                 550                 555                 560
Leu Ser Asn Leu Asp Glu Val Lys Lys Glu Arg Glu Gly Leu Glu Asn
                565                 570                 575
Asp Leu Lys Ser Val Asn Phe Asp Met Thr Ser Lys Phe Leu Thr Ala
                580                 585                 590
Leu Ala Gln Asp Gly Val Ile Asn Glu Glu Ala Leu Ser Val Thr Glu
            595                 600                 605
Leu Asp Arg Val Tyr Gly Gly Leu Thr Thr Lys Val Gln Glu Ser Leu
610                 615                 620
Lys Lys Gln Glu Gly Leu Leu Lys Asn Ile Gln Val Ser His Gln Glu
625                 630                 635                 640
Phe Ser Lys Met Lys Gln Ser Asn Asn Glu Ala Asn Leu Arg Glu Glu
                645                 650                 655
Val Leu Lys Asn Leu Ala Thr Ala Tyr Asp Asn Phe Val Glu Leu Val
                660                 665                 670
Ala Asn Leu Lys Glu Gly Thr Lys Phe Tyr Asn Glu Leu Thr Glu Ile
            675                 680                 685
Leu Val Arg Phe Gln Asn Lys Cys Ser Asp Ile Val Phe Ala Arg Lys
690                 695                 700
Thr Glu Arg Asp Glu Leu Leu Lys Asp Leu Gln Gln Ser Ile Ala Arg
705                 710                 715                 720
Glu Pro Ser Ala Pro Ser Ile Pro Thr Pro Ala Tyr Gln Ser Ser Pro
                725                 730                 735
Ala Gly Gly His Ala Pro Thr Pro Thr Pro Ala Pro Arg Thr Met
                740                 745                 750
Pro Pro Thr Lys Pro Gln Pro Pro Ala Arg Pro Pro Pro Val Leu
            755                 760                 765
Pro Ala Asn Arg Ala Pro Ser Ala Thr Ala Pro Ser Pro Val Gly Ala
770                 775                 780
Gly Thr Ala Ala Pro Ala Pro Ser Gln Thr Pro Gly Ser Ala Pro Pro
785                 790                 795                 800
Pro Gln Ala Gln Gly Pro Pro Tyr Pro Thr Tyr Pro Gly Tyr Pro Gly
                805                 810                 815
Tyr Cys Gln Met Pro Met Pro Met Gly Tyr Asn Pro Tyr Ala Tyr Gly
                820                 825                 830
Gln Tyr Asn Met Pro Tyr Pro Val Tyr His Gln Ser Pro Gly Gln
                835                 840                 845
Ala Pro Tyr Pro Gly Pro Gln Gln Pro Ser Tyr Pro Phe Pro Gln Pro
850                 855                 860

Pro Gln Gln Ser Tyr Tyr Pro Gln Gln
```

<210> SEQ ID NO 29
<211> LENGTH: 298
<212> TYPE: PRT
<213> ORGANISM: Homo sapiens

<400> SEQUENCE: 29

Met Ser Leu Tyr Pro Ser Leu Glu Asp Leu Lys Val Asp Lys Val Ile
1               5                   10                  15

Gln Ala Gln Thr Ala Phe Ser Ala Asn Pro Ala Asn Pro Ala Ile Leu
            20                  25                  30

Ser Glu Ala Ser Ala Pro Ile Pro His Asp Gly Asn Leu Tyr Pro Arg
        35                  40                  45

Leu Tyr Pro Glu Leu Ser Gln Tyr Met Gly Leu Ser Leu Asn Glu Glu
    50                  55                  60

Glu Ile Arg Ala Ser Val Ala Val Ser Gly Ala Pro Leu Gln Gly
65                  70                  75                  80

Gln Leu Val Ala Arg Pro Ser Ser Ile Asn Tyr Met Val Ala Pro Val
                85                  90                  95

Thr Gly Asn Asp Val Gly Ile Arg Arg Ala Glu Ile Lys Gln Gly Ile
            100                 105                 110

Arg Glu Val Ile Leu Cys Lys Asp Gln Asp Gly Lys Ile Gly Leu Arg
        115                 120                 125

Leu Lys Ser Ile Asp Asn Gly Ile Phe Val Gln Leu Val Gln Ala Asn
    130                 135                 140

Ser Pro Ala Ser Leu Val Gly Leu Arg Phe Gly Asp Gln Val Leu Gln
145                 150                 155                 160

Ile Asn Gly Glu Asn Cys Ala Gly Trp Ser Ser Asp Lys Ala His Lys
                165                 170                 175

Val Leu Lys Gln Ala Phe Gly Glu Lys Ile Thr Met Thr Ile Arg Asp
            180                 185                 190

Arg Pro Phe Glu Arg Thr Ile Thr Met His Lys Asp Ser Thr Gly His
        195                 200                 205

Val Gly Phe Ile Phe Lys Asn Gly Lys Ile Thr Ser Ile Val Lys Asp
    210                 215                 220

Ser Ser Ala Ala Arg Asn Gly Leu Leu Thr Glu His Asn Ile Cys Glu
225                 230                 235                 240

Ile Asn Gly Gln Asn Val Ile Gly Leu Lys Asp Ser Gln Ile Ala Asp
                245                 250                 255

Ile Leu Ser Thr Ser Gly Thr Val Val Thr Ile Thr Ile Met Pro Ala
            260                 265                 270

Phe Ile Phe Glu His Ile Ile Lys Arg Met Ala Pro Ser Ile Met Lys
        275                 280                 285

Ser Leu Met Asp His Thr Ile Pro Glu Val
    290                 295

<210> SEQ ID NO 30
<211> LENGTH: 455
<212> TYPE: PRT
<213> ORGANISM: Homo sapiens

<400> SEQUENCE: 30

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro

-continued

```
             20                  25                  30
His Leu Gly Asp Arg Glu Lys Arg Asp Ser Val Cys Pro Gln Gly Lys
             35                  40                  45

Tyr Ile His Pro Gln Asn Asn Ser Ile Cys Cys Thr Lys Cys His Lys
 50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
             85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
            130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
            210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
            290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445
```

```
Pro Ala Pro Ser Leu Leu Arg
    450                 455

<210> SEQ ID NO 31
<211> LENGTH: 461
<212> TYPE: PRT
<213> ORGANISM: Homo sapiens

<400> SEQUENCE: 31

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
        275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
```

```
                  355                 360                 365
Asp Ser Ser Pro Gly His Gly Thr Gln Val Asn Val Thr Cys Ile
    370                 375                 380

Val Asn Val Cys Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
                420                 425                 430

Gln Leu Glu Thr Pro Glu Thr Leu Leu Gly Ser Thr Glu Lys Pro
                435                 440                 445

Leu Pro Leu Gly Val Pro Asp Ala Gly Met Lys Pro Ser
    450                 455                 460

<210> SEQ ID NO 32
<211> LENGTH: 427
<212> TYPE: PRT
<213> ORGANISM: Homo sapiens

<400> SEQUENCE: 32

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
        50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Glu Gln Asp Leu Ile
    210                 215                 220

Ala Ser Thr Val Ala Gly Val Val Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270
```

```
Lys Arg Trp Asn Ser Cys Lys Gln Asn Lys Gln Gly Ala Asn Ser Arg
            275                 280                 285

Pro Val Asn Gln Thr Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Leu Tyr
                325                 330                 335

Ser Ser Leu Pro Pro Ala Lys Arg Glu Val Glu Lys Leu Leu Asn
            340                 345                 350

Gly Ser Ala Gly Asp Thr Trp Arg His Leu Ala Gly Glu Leu Gly Tyr
            355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Asp Ala
385                 390                 395                 400

Leu Leu Ala Ala Leu Arg Arg Ile Gln Arg Ala Asp Leu Val Glu Ser
                405                 410                 415

Leu Cys Ser Glu Ser Thr Ala Thr Ser Pro Val
            420                 425

<210> SEQ ID NO 33
<211> LENGTH: 426
<212> TYPE: PRT
<213> ORGANISM: Homo sapiens

<400> SEQUENCE: 33

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
    115                 120                 125

Val Leu Gln Glu Ser Ile Gly Lys Gly Arg Phe Gly Glu Val Trp Arg
130                 135                 140

Gly Lys Trp Arg Gly Glu Glu Val Ala Val Lys Ile Phe Ser Ser Arg
145                 150                 155                 160

Glu Glu Arg Ser Trp Phe Arg Glu Ala Glu Ile Tyr Gln Thr Val Met
                165                 170                 175

Leu Arg His Glu Asn Ile Leu Gly Phe Ile Ala Ala Asp Asn Lys Asp
            180                 185                 190

Asn Gly Thr Trp Thr Gln Leu Trp Leu Val Ser Asp Tyr His Glu His
    195                 200                 205

Gly Ser Leu Phe Asp Tyr Leu Asn Arg Tyr Thr Val Thr Val Glu Gly
210                 215                 220
```

-continued

```
Met Ile Lys Leu Ala Leu Ser Thr Ala Ser Gly Leu Ala His Leu His
225                 230                 235                 240

Met Glu Ile Val Gly Thr Gln Gly Lys Pro Ala Ile Ala His Arg Asp
            245                 250                 255

Leu Lys Ser Lys Asn Ile Leu Val Lys Lys Asn Gly Thr Cys Cys Ile
        260                 265                 270

Ala Asp Leu Gly Leu Ala Val Arg His Asp Ser Ala Thr Asp Thr Ile
    275                 280                 285

Asp Ile Ala Pro Asn His Arg Val Gly Thr Lys Arg Tyr Met Ala Pro
290                 295                 300

Glu Val Leu Asp Asp Ser Ile Asn Met Lys His Phe Glu Ser Phe Lys
305                 310                 315                 320

Arg Ala Asp Ile Tyr Ala Met Gly Leu Val Phe Trp Glu Ile Ala Arg
            325                 330                 335

Arg Cys Ser Ile Gly Gly Ile His Glu Asp Tyr Gln Leu Pro Tyr Tyr
        340                 345                 350

Asp Leu Val Pro Ser Asp Pro Ser Val Glu Glu Met Arg Lys Val Val
    355                 360                 365

Cys Glu Gln Lys Leu Arg Pro Asn Ile Pro Asn Arg Trp Gln Ser Cys
370                 375                 380

Glu Ala Leu Arg Val Met Ala Lys Ile Met Arg Glu Cys Trp Tyr Ala
385                 390                 395                 400

Asn Gly Ala Ala Arg Leu Thr Ala Leu Arg Ile Lys Lys Thr Leu Ser
            405                 410                 415

Gln Leu Ser Gln Gln Gly Ile Lys Met
        420                 425

<210> SEQ ID NO 34
<211> LENGTH: 592
<212> TYPE: PRT
<213> ORGANISM: Homo sapiens

<400> SEQUENCE: 34

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
            20                  25                  30

Val Glu Met Glu Ala Gln Lys Asp Glu Ile Ile Cys Pro Ser Cys Asn
        35                  40                  45

Arg Thr Ala His Pro Leu Arg His Ile Asn Asn Asp Met Ile Val Thr
    50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
```

```
            165                 170                 175
Glu Tyr Asn Thr Ser Asn Pro Asp Leu Leu Val Ile Phe Gln Val
            180                 185                 190
Thr Gly Ile Ser Leu Leu Pro Pro Leu Gly Val Ala Ile Ser Val Ile
            195                 200                 205
Ile Ile Phe Tyr Cys Tyr Arg Val Asn Arg Gln Gln Lys Leu Ser Ser
            210                 215                 220
Thr Trp Glu Thr Gly Lys Thr Arg Lys Leu Met Glu Phe Ser Glu His
225                 230                 235                 240
Cys Ala Ile Ile Leu Glu Asp Asp Arg Ser Asp Ile Ser Ser Thr Cys
            245                 250                 255
Ala Asn Asn Ile Asn His Asn Thr Glu Leu Leu Pro Ile Glu Leu Asp
            260                 265                 270
Thr Leu Val Gly Lys Gly Arg Phe Ala Glu Val Tyr Lys Ala Lys Leu
            275                 280                 285
Lys Gln Asn Thr Ser Glu Gln Phe Glu Thr Val Ala Val Lys Ile Phe
            290                 295                 300
Pro Tyr Glu Glu Tyr Ala Ser Trp Lys Thr Glu Lys Asp Ile Phe Ser
305                 310                 315                 320
Asp Ile Asn Leu Lys His Glu Asn Ile Leu Gln Phe Leu Thr Ala Glu
            325                 330                 335
Glu Arg Lys Thr Glu Leu Gly Lys Gln Tyr Trp Leu Ile Thr Ala Phe
            340                 345                 350
His Ala Lys Gly Asn Leu Gln Glu Tyr Leu Thr Arg His Val Ile Ser
            355                 360                 365
Trp Glu Asp Leu Arg Lys Leu Gly Ser Ser Leu Ala Arg Gly Ile Ala
            370                 375                 380
His Leu His Ser Asp His Thr Pro Cys Gly Arg Pro Lys Met Pro Ile
385                 390                 395                 400
Val His Arg Asp Leu Lys Ser Ser Asn Ile Leu Val Lys Asn Asp Leu
            405                 410                 415
Thr Cys Cys Leu Cys Asp Phe Gly Leu Ser Leu Arg Leu Asp Pro Thr
            420                 425                 430
Leu Ser Val Asp Asp Leu Ala Asn Ser Gly Gln Val Gly Thr Ala Arg
            435                 440                 445
Tyr Met Ala Pro Glu Val Leu Glu Ser Arg Met Asn Leu Glu Asn Val
            450                 455                 460
Glu Ser Phe Lys Gln Thr Asp Val Tyr Ser Met Ala Leu Val Leu Trp
465                 470                 475                 480
Glu Met Thr Ser Arg Cys Asn Ala Val Gly Glu Val Lys Asp Tyr Glu
            485                 490                 495
Pro Pro Phe Gly Ser Lys Val Arg Glu His Pro Cys Val Glu Ser Met
            500                 505                 510
Lys Asp Asn Val Leu Arg Asp Arg Gly Arg Pro Glu Ile Pro Ser Phe
            515                 520                 525
Trp Leu Asn His Gln Gly Ile Gln Met Val Cys Glu Thr Leu Thr Glu
            530                 535                 540
Cys Trp Asp His Asp Pro Glu Ala Arg Leu Thr Ala Gln Cys Val Ala
545                 550                 555                 560
Glu Arg Phe Ser Glu Leu Glu His Leu Asp Arg Leu Ser Gly Arg Ser
            565                 570                 575
Cys Ser Glu Glu Lys Ile Pro Glu Asp Gly Ser Leu Asn Thr Thr Lys
            580                 585                 590
```

<210> SEQ ID NO 35
<211> LENGTH: 850
<212> TYPE: PRT
<213> ORGANISM: Homo sapiens

<400> SEQUENCE: 35

```
Met Thr Ser His Tyr Val Ile Ala Ile Phe Ala Leu Met Ser Ser Cys
1               5                   10                  15
Leu Ala Thr Ala Gly Pro Glu Pro Gly Ala Leu Cys Glu Leu Ser Pro
                20                  25                  30
Val Ser Ala Ser His Pro Val Gln Ala Leu Met Glu Ser Phe Thr Val
            35                  40                  45
Leu Ser Gly Cys Ala Ser Arg Gly Thr Thr Gly Leu Pro Gln Glu Val
        50                  55                  60
His Val Leu Asn Leu Arg Thr Ala Gly Gln Gly Pro Gly Gln Leu Gln
65                  70                  75                  80
Arg Glu Val Thr Leu His Leu Asn Pro Ile Ser Ser Val His Ile His
                85                  90                  95
His Lys Ser Val Val Phe Leu Leu Asn Ser Pro His Pro Leu Val Trp
            100                 105                 110
His Leu Lys Thr Glu Arg Leu Ala Thr Gly Val Ser Arg Leu Phe Leu
        115                 120                 125
Val Ser Glu Gly Ser Val Val Gln Phe Ser Ser Ala Asn Phe Ser Leu
    130                 135                 140
Thr Ala Glu Thr Glu Glu Arg Asn Phe Pro His Gly Asn Glu His Leu
145                 150                 155                 160
Leu Asn Trp Ala Arg Lys Glu Tyr Gly Ala Val Thr Ser Phe Thr Glu
                165                 170                 175
Leu Lys Ile Ala Arg Asn Ile Tyr Ile Lys Val Gly Glu Asp Gln Val
            180                 185                 190
Phe Pro Pro Lys Cys Asn Ile Gly Lys Asn Phe Leu Ser Leu Asn Tyr
        195                 200                 205
Leu Ala Glu Tyr Leu Gln Pro Lys Ala Ala Glu Gly Cys Val Met Ser
    210                 215                 220
Ser Gln Pro Gln Asn Glu Glu Val His Ile Ile Glu Leu Ile Thr Pro
225                 230                 235                 240
Asn Ser Asn Pro Tyr Ser Ala Phe Gln Val Asp Ile Thr Ile Asp Ile
                245                 250                 255
Arg Pro Ser Gln Glu Asp Leu Glu Val Val Lys Asn Leu Ile Leu Ile
            260                 265                 270
Leu Lys Cys Lys Lys Ser Val Asn Trp Val Ile Lys Ser Phe Asp Val
        275                 280                 285
Lys Gly Ser Leu Lys Ile Ile Ala Pro Asn Ser Ile Gly Phe Gly Lys
    290                 295                 300
Glu Ser Glu Arg Ser Met Thr Met Thr Lys Ser Ile Arg Asp Asp Ile
305                 310                 315                 320
Pro Ser Thr Gln Gly Asn Leu Val Lys Trp Ala Leu Asp Asn Gly Tyr
                325                 330                 335
Ser Pro Ile Thr Ser Tyr Thr Met Ala Pro Val Ala Asn Arg Phe His
            340                 345                 350
Leu Arg Leu Glu Asn Asn Glu Glu Met Gly Asp Glu Glu Val His Thr
        355                 360                 365
Ile Pro Pro Glu Leu Arg Ile Leu Leu Asp Pro Gly Ala Leu Pro Ala
```

```
             370                 375                 380
Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Val Gln Gly Ser Val Asp
            435                 440                 445

Ile Ala Leu Ser Val Lys Cys Asp Asn Glu Lys Met Ile Val Ala Val
        450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
        515                 520                 525

Leu Gly Asp Ser Ser Gly Trp Pro Asp Gly Tyr Glu Asp Leu Glu Ser
    530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
    610                 615                 620

Thr Lys Ala Glu Gln Glu Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
            660                 665                 670

Val His Phe Pro Ile Pro Gln Ala Asp Met Asp Lys Lys Arg Phe Ser
        675                 680                 685

Phe Val Phe Lys Pro Val Phe Asn Thr Ser Leu Leu Phe Leu Gln Cys
    690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765

Glu Pro Asn Pro Ile Ser Pro Pro Ile Phe His Gly Leu Asp Thr Leu
    770                 775                 780

Thr Val Met Gly Ile Ala Phe Ala Ala Phe Val Ile Gly Ala Leu Leu
785                 790                 795                 800
```

Thr Gly Ala Leu Trp Tyr Ile Tyr Ser His Thr Gly Glu Thr Ala Gly
                805                 810                 815

Arg Gln Gln Val Pro Thr Ser Pro Pro Ala Ser Glu Asn Ser Ser Ala
            820                 825                 830

Ala His Ser Ile Gly Ser Thr Gln Ser Thr Pro Cys Ser Ser Ser Ser
        835                 840                 845

Thr Ala
    850

<210> SEQ ID NO 36
<211> LENGTH: 820
<212> TYPE: PRT
<213> ORGANISM: Homo sapiens

<400> SEQUENCE: 36

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp

```
            305                 310                 315                 320
Lys Glu Met Glu Val Leu His Leu Arg Asn Val Ser Phe Glu Asp Ala
                    325                 330                 335
Gly Glu Tyr Thr Cys Leu Ala Gly Asn Ser Ile Gly Leu Ser His His
                    340                 345                 350
Ser Ala Trp Leu Thr Val Leu Glu Ala Leu Glu Arg Pro Ala Val
                    355                 360             365
Met Thr Ser Pro Leu Tyr Leu Glu Ile Ile Ile Tyr Cys Thr Gly Ala
                    370                 375             380
Phe Leu Ile Ser Cys Met Val Gly Ser Val Ile Val Tyr Lys Met Lys
385                 390                 395                 400
Ser Gly Thr Lys Lys Ser Asp Phe His Ser Gln Met Ala Val His Lys
                    405                 410                 415
Leu Ala Lys Ser Ile Pro Leu Arg Arg Gln Val Ser Ala Asp Ser Ser
                    420                 425                 430
Ala Ser Met Asn Ser Gly Val Leu Leu Val Arg Pro Ser Arg Leu Ser
                    435                 440                 445
Ser Ser Gly Thr Pro Met Leu Ala Gly Val Ser Glu Tyr Glu Leu Pro
                    450                 455                 460
Glu Asp Pro Arg Trp Glu Leu Pro Arg Asp Arg Leu Val Leu Gly Lys
465                 470                 475                 480
Pro Leu Gly Glu Gly Cys Phe Gly Gln Val Val Leu Ala Glu Ala Ile
                    485                 490                 495
Gly Leu Asp Lys Asp Lys Pro Asn Arg Val Thr Lys Val Ala Val Lys
                    500                 505                 510
Met Leu Lys Ser Asp Ala Thr Glu Lys Asp Leu Ser Asp Leu Ile Ser
                    515                 520                 525
Glu Met Glu Met Met Lys Met Ile Gly Lys His Lys Asn Ile Ile Asn
                    530                 535                 540
Leu Leu Gly Ala Cys Thr Gln Asp Gly Pro Leu Tyr Val Ile Val Glu
545                 550                 555                 560
Tyr Ala Ser Lys Gly Asn Leu Arg Glu Tyr Leu Gln Ala Arg Arg Pro
                    565                 570                 575
Pro Gly Leu Glu Tyr Cys Tyr Asn Pro Ser His Asn Pro Glu Glu Gln
                    580                 585                 590
Leu Ser Ser Lys Asp Leu Val Ser Cys Ala Tyr Gln Val Ala Arg Gly
                    595                 600                 605
Met Glu Tyr Leu Ala Ser Lys Lys Cys Ile His Arg Asp Leu Ala Ala
                    610                 615                 620
Arg Asn Val Leu Val Thr Glu Asp Asn Val Met Lys Ile Ala Asp Phe
625                 630                 635                 640
Gly Leu Ala Arg Asp Ile His His Ile Asp Tyr Tyr Lys Lys Thr Thr
                    645                 650                 655
Asn Gly Arg Leu Pro Val Lys Trp Met Ala Pro Glu Ala Leu Phe Asp
                    660                 665                 670
Arg Ile Tyr Thr His Gln Ser Asp Val Trp Ser Phe Gly Val Leu Leu
                    675                 680                 685
Trp Glu Ile Phe Thr Leu Gly Gly Ser Pro Tyr Pro Gly Val Pro Val
                    690                 695                 700
Glu Glu Leu Phe Lys Leu Leu Lys Glu Gly His Arg Met Asp Lys Pro
705                 710                 715                 720
Ser Asn Cys Thr Asn Glu Leu Tyr Met Met Met Arg Asp Cys Trp His
                    725                 730                 735
```

```
Ala Val Pro Ser Gln Arg Pro Thr Phe Lys Gln Leu Val Glu Asp Leu
                740                 745                 750

Asp Arg Ile Val Ala Leu Thr Ser Asn Gln Glu Tyr Leu Asp Leu Ser
            755                 760                 765

Met Pro Leu Asp Gln Tyr Ser Pro Ser Phe Pro Asp Thr Arg Ser Ser
770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820

<210> SEQ ID NO 37
<211> LENGTH: 821
<212> TYPE: PRT
<213> ORGANISM: Homo sapiens

<400> SEQUENCE: 37

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
```

-continued

```
            275                 280                 285
Gln Trp Ile Lys His Val Glu Lys Asn Gly Ser Lys Tyr Gly Pro Asp
    290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
            340                 345                 350
His Ser Ala Trp Leu Thr Val Leu Pro Ala Pro Gly Arg Glu Lys Glu
        355                 360                 365
Ile Thr Ala Ser Pro Asp Tyr Leu Glu Ile Ala Ile Tyr Cys Ile Gly
370                 375                 380
Val Phe Leu Ile Ala Cys Met Val Val Thr Val Ile Leu Cys Arg Met
385                 390                 395                 400
Lys Asn Thr Thr Lys Lys Pro Asp Phe Ser Ser Gln Pro Ala Val His
                405                 410                 415
Lys Leu Thr Lys Arg Ile Pro Leu Arg Arg Gln Val Thr Val Ser Ala
                420                 425                 430
Glu Ser Ser Ser Ser Met Asn Ser Asn Thr Pro Leu Val Arg Ile Thr
            435                 440                 445
Thr Arg Leu Ser Ser Thr Ala Asp Thr Pro Met Leu Ala Gly Val Ser
450                 455                 460
Glu Tyr Glu Leu Pro Glu Asp Pro Lys Trp Glu Phe Pro Arg Asp Lys
465                 470                 475                 480
Leu Thr Leu Gly Lys Pro Leu Gly Glu Gly Cys Phe Gly Gln Val Val
                485                 490                 495
Met Ala Glu Ala Val Gly Ile Asp Lys Asp Lys Pro Lys Glu Ala Val
                500                 505                 510
Thr Val Ala Val Lys Met Leu Lys Asp Asp Ala Thr Glu Lys Asp Leu
            515                 520                 525
Ser Asp Leu Val Ser Glu Met Glu Met Met Lys Met Ile Gly Lys His
530                 535                 540
Lys Asn Ile Ile Asn Leu Leu Gly Ala Cys Thr Gln Asp Gly Pro Leu
545                 550                 555                 560
Tyr Val Ile Val Glu Tyr Ala Ser Lys Gly Asn Leu Arg Glu Tyr Leu
                565                 570                 575
Arg Ala Arg Arg Pro Pro Gly Met Glu Tyr Ser Tyr Asp Ile Asn Arg
                580                 585                 590
Val Pro Glu Glu Gln Met Thr Phe Lys Asp Leu Val Ser Cys Thr Tyr
            595                 600                 605
Gln Leu Ala Arg Gly Met Glu Tyr Leu Ala Ser Gln Lys Cys Ile His
        610                 615                 620
Arg Asp Leu Ala Ala Arg Asn Val Leu Val Thr Glu Asn Asn Val Met
625                 630                 635                 640
Lys Ile Ala Asp Phe Gly Leu Ala Arg Asp Ile Asn Asn Ile Asp Tyr
                645                 650                 655
Tyr Lys Lys Thr Thr Asn Gly Arg Leu Pro Val Lys Trp Met Ala Pro
                660                 665                 670
Glu Ala Leu Phe Asp Arg Val Tyr Thr His Gln Ser Asp Val Trp Ser
            675                 680                 685
Phe Gly Val Leu Met Trp Glu Ile Phe Thr Leu Gly Gly Ser Pro Tyr
        690                 695                 700
```

```
Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
            725                 730                 735

Arg Asp Cys Trp His Ala Val Pro Ser Gln Arg Pro Thr Phe Lys Gln
        740                 745                 750

Leu Val Glu Asp Leu Asp Arg Ile Leu Thr Leu Thr Thr Asn Glu Glu
    755                 760                 765

Tyr Leu Asp Leu Ser Gln Pro Leu Glu Gln Tyr Ser Pro Ser Tyr Pro
770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 38
<211> LENGTH: 806
<212> TYPE: PRT
<213> ORGANISM: Homo sapiens

<400> SEQUENCE: 38

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
```

```
            245                 250                 255
Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Glu Leu Val Glu Ala Asp Glu
                355                 360                 365

Ala Gly Ser Val Tyr Ala Gly Ile Leu Ser Tyr Gly Val Gly Phe Phe
                370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
                435                 440                 445

Pro Thr Leu Ala Asn Val Ser Glu Leu Glu Leu Pro Ala Asp Pro Lys
                450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
                515                 520                 525

Met Lys Met Ile Gly Lys His Lys Asn Ile Ile Asn Leu Leu Gly Ala
                530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670
```

```
His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
                755                 760                 765

Gln Tyr Ser Pro Gly Gly Gln Asp Thr Pro Ser Ser Ser Ser Ser Gly
        770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 39
<211> LENGTH: 802
<212> TYPE: PRT
<213> ORGANISM: Homo sapiens

<400> SEQUENCE: 39

Met Arg Leu Leu Leu Ala Leu Gly Val Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205

Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
```

-continued

```
            225                 230                 235                 240
Val Leu Glu Arg Ser Pro His Arg Pro Ile Leu Gln Ala Gly Leu Pro
                245                 250                 255
Ala Asn Thr Thr Ala Val Val Gly Ser Asp Val Glu Leu Leu Cys Lys
                260                 265                 270
Val Tyr Ser Asp Ala Gln Pro His Ile Gln Trp Leu Lys His Ile Val
                275                 280                 285
Ile Asn Gly Ser Ser Phe Gly Ala Asp Gly Phe Pro Tyr Val Gln Val
                290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
                340                 345                 350
Glu Glu Asp Pro Thr Trp Thr Ala Ala Pro Glu Ala Arg Tyr Thr
                355                 360                 365
Asp Ile Ile Leu Tyr Ala Ser Gly Ser Leu Ala Leu Ala Val Leu Leu
                370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Ser Gly Lys Ser Ser Ser Ser Leu
                420                 425                 430
Val Arg Gly Val Arg Leu Ser Ser Ser Gly Pro Ala Leu Leu Ala Gly
                435                 440                 445
Leu Val Ser Leu Asp Leu Pro Leu Asp Pro Leu Trp Glu Phe Pro Arg
                450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
Ala Ser Thr Val Ala Val Lys Met Leu Lys Asp Asn Ala Ser Asp Lys
                500                 505                 510
Asp Leu Ala Asp Leu Val Ser Glu Met Glu Val Met Lys Leu Ile Gly
                515                 520                 525
Arg His Lys Asn Ile Ile Asn Leu Leu Gly Val Cys Thr Gln Glu Gly
                530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Arg Ser Ser Glu Gly Pro Leu Ser Phe Pro Val Leu Val Ser Cys
                580                 585                 590
Ala Tyr Gln Val Ala Arg Gly Met Gln Tyr Leu Glu Ser Arg Lys Cys
                595                 600                 605
Ile His Arg Asp Leu Ala Ala Arg Asn Val Leu Val Thr Glu Asp Asn
                610                 615                 620
Val Met Lys Ile Ala Asp Phe Gly Leu Ala Arg Gly Val His His Ile
625                 630                 635                 640
Asp Tyr Tyr Lys Lys Thr Ser Asn Gly Arg Leu Pro Val Lys Trp Met
                645                 650                 655
```

```
Ala Pro Glu Ala Leu Phe Asp Arg Val Tyr Thr His Gln Ser Asp Val
        660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
        690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
        770                 775                 780

Asp Pro Leu Pro Leu Gly Ser Ser Ser Phe Pro Phe Gly Ser Gly Val
785                 790                 795                 800

Gln Thr

<210> SEQ ID NO 40
<211> LENGTH: 509
<212> TYPE: PRT
<213> ORGANISM: Homo sapiens

<400> SEQUENCE: 40

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220
```

```
Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
        290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 41
<211> LENGTH: 505
<212> TYPE: PRT
<213> ORGANISM: Homo sapiens

<400> SEQUENCE: 41

Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
```

```
                   85                  90                  95
Tyr Thr Asp Tyr Cys Asn Arg Ile Asp Leu Arg Val Pro Ser Gly His
                100                 105                 110

Leu Lys Glu Pro Glu His Pro Ser Met Trp Gly Pro Val Glu Leu Val
                115                 120                 125

Gly Ile Ile Ala Gly Pro Val Phe Leu Leu Phe Leu Ile Ile Ile Ile
            130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
                180                 185                 190

Ser Gly Leu Pro Leu Phe Val Gln Arg Thr Val Ala Arg Thr Ile Val
            195                 200                 205

Leu Gln Glu Ile Ile Gly Lys Gly Arg Phe Gly Glu Val Trp Arg Gly
            210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
                260                 265                 270

Gly Thr Trp Thr Gln Leu Trp Leu Val Ser Asp Tyr His Glu His Gly
                275                 280                 285

Ser Leu Phe Asp Tyr Leu Asn Arg Tyr Thr Val Thr Ile Glu Gly Met
290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
                340                 345                 350

Asp Leu Gly Leu Ala Val Arg His Asp Ala Val Thr Asp Thr Ile Asp
            355                 360                 365

Ile Ala Pro Asn Gln Arg Val Gly Thr Lys Arg Tyr Met Ala Pro Glu
            370                 375                 380

Val Leu Asp Glu Thr Ile Asn Met Lys His Phe Asp Ser Phe Lys Cys
385                 390                 395                 400

Ala Asp Ile Tyr Ala Leu Gly Leu Val Tyr Trp Glu Ile Ala Arg Arg
                405                 410                 415

Cys Asn Ser Gly Gly Val His Glu Glu Tyr Gln Leu Pro Tyr Tyr Asp
                420                 425                 430

Leu Val Pro Ser Asp Pro Ser Ile Glu Glu Met Arg Lys Val Val Cys
            435                 440                 445

Asp Gln Lys Leu Arg Pro Asn Ile Pro Asn Trp Trp Gln Ser Tyr Glu
            450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
            500                 505
```

<210> SEQ ID NO 42
<211> LENGTH: 513
<212> TYPE: PRT
<213> ORGANISM: Homo sapiens

<400> SEQUENCE: 42

```
Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
```

```
                370                 375                 380
Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
                435                 440                 445

Ala Gly Met Ala Met Leu Cys Glu Thr Ile Glu Glu Cys Trp Asp His
                450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 43
<211> LENGTH: 512
<212> TYPE: PRT
<213> ORGANISM: Homo sapiens

<400> SEQUENCE: 43

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Arg
                50                  55                  60

Asn Ser Ser Gly Thr Ile Glu Leu Val Lys Lys Gly Cys Trp Leu Asp
65              70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
                115                 120                 125

Pro Pro Thr Ala Pro Thr Leu Leu Thr Val Leu Ala Tyr Ser Leu Leu
                130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
                180                 185                 190

Leu Glu Ile Lys Ala Arg Gly Arg Phe Gly Cys Val Trp Lys Ala Gln
                195                 200                 205

Leu Met Asn Asp Phe Val Ala Val Lys Ile Phe Pro Leu Gln Asp Lys
                210                 215                 220

Gln Ser Trp Gln Ser Glu Arg Glu Ile Phe Ser Thr Pro Gly Met Lys
```

His Glu Asn Leu Leu Gln Phe Ile Ala Ala Glu Lys Arg Gly Ser Asn
225                 230                 235                 240

Leu Glu Val Glu Leu Trp Leu Ile Thr Ala Phe His Asp Lys Gly Ser
            245                 250                 255

Leu Thr Asp Tyr Leu Lys Gly Asn Ile Ile Thr Trp Asn Glu Leu Cys
        260                 265                 270

His Val Ala Glu Thr Met Ser Arg Gly Leu Ser Tyr Leu His Glu Asp
    275                 280                 285

Val Pro Trp Cys Arg Gly Glu Gly His Lys Pro Ser Ile Ala His Arg
290                 295                 300

Asp Phe Lys Ser Lys Asn Val Leu Leu Lys Ser Asp Leu Thr Ala Val
305                 310                 315                 320

Leu Ala Asp Phe Gly Leu Ala Val Arg Phe Glu Pro Gly Lys Pro Pro
            325                 330                 335

Gly Asp Thr His Gly Gln Val Gly Thr Arg Arg Tyr Met Ala Pro Glu
        340                 345                 350

Val Leu Glu Gly Ala Ile Asn Phe Gln Arg Asp Ala Phe Leu Arg Ile
    355                 360                 365

Asp Met Tyr Ala Met Gly Leu Val Leu Trp Glu Leu Val Ser Arg Cys
370                 375                 380

Lys Ala Ala Asp Gly Pro Val Asp Glu Tyr Met Leu Pro Phe Glu Glu
385                 390                 395                 400

Glu Ile Gly Gln His Pro Ser Leu Glu Glu Leu Gln Glu Val Val Val
            405                 410                 415

His Lys Lys Met Arg Pro Thr Ile Lys Asp His Trp Leu Lys His Pro
        420                 425                 430

Gly Leu Ala Gln Leu Cys Val Thr Ile Glu Glu Cys Trp Asp His Asp
    435                 440                 445

Ala Glu Ala Arg Leu Ser Ala Gly Cys Val Glu Glu Arg Val Ser Leu
450                 455                 460

Ile Arg Arg Ser Val Asn Gly Thr Thr Ser Asp Cys Leu Val Ser Leu
465                 470                 475                 480

Val Thr Ser Val Thr Asn Val Asp Leu Pro Pro Lys Glu Ser Ser Ile
            485                 490                 495
                500                 505                 510

<210> SEQ ID NO 44
<211> LENGTH: 1447
<212> TYPE: PRT
<213> ORGANISM: Homo sapiens

<400> SEQUENCE: 44

Met Ala Ser Ala Gly Asn Ala Ala Glu Pro Gln Asp Arg Gly Gly Gly
1               5                   10                  15

Gly Ser Gly Cys Ile Gly Ala Pro Gly Arg Pro Ala Gly Gly Gly Arg
            20                  25                  30

Arg Arg Arg Thr Gly Gly Leu Arg Ala Ala Ala Pro Asp Arg Asp
        35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95

```
Asn Cys Gly Lys Phe Leu Val Val Gly Leu Ile Phe Gly Ala Phe
            100                 105                 110

Ala Val Gly Leu Lys Ala Ala Asn Leu Glu Thr Asn Val Glu Glu Leu
        115                 120                 125

Trp Val Glu Val Gly Arg Val Ser Arg Glu Leu Asn Tyr Thr Arg
    130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
        180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
        210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
        260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
        290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
        340                 345                 350

Lys Leu Val Ser Ala His Ala Leu Gln Thr Met Phe Gln Leu Met Thr
        355                 360                 365

Pro Lys Gln Met Tyr Glu His Phe Lys Gly Tyr Glu Tyr Val Ser His
    370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Thr Leu Asp Asp Ile Leu Lys
        420                 425                 430

Ser Phe Ser Asp Val Ser Val Ile Arg Val Ala Ser Gly Tyr Leu Leu
        435                 440                 445

Met Leu Ala Tyr Ala Cys Leu Thr Met Leu Arg Trp Asp Cys Ser Lys
    450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
        500                 505                 510

Asp Asp Val Phe Leu Leu Ala His Ala Phe Ser Glu Thr Gly Gln Asn
```

```
            515                 520                 525
Lys Arg Ile Pro Phe Glu Asp Arg Thr Gly Glu Cys Leu Lys Arg Thr
530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Phe Ala Met Val Leu Leu Ile Phe
                580                 585                 590

Pro Ala Ile Leu Ser Met Asp Leu Tyr Arg Arg Glu Asp Arg Leu
                595                 600                 605

Asp Ile Phe Cys Cys Phe Thr Ser Pro Cys Val Ser Arg Val Ile Gln
            610                 615                 620

Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                645                 650                 655

Thr Met Gln Ser Thr Val Gln Leu Arg Thr Glu Tyr Asp Pro His Thr
                660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                725                 730                 735

Glu Lys His Tyr Ala Pro Phe Leu Leu Lys Pro Lys Ala Lys Val Val
                740                 745                 750

Val Ile Phe Leu Phe Leu Gly Leu Leu Gly Val Ser Leu Tyr Gly Thr
            755                 760                 765

Thr Arg Val Arg Asp Gly Leu Asp Leu Thr Asp Ile Val Pro Arg Glu
770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                805                 810                 815

His Leu Leu Tyr Asp Leu His Arg Ser Phe Ser Asn Val Lys Tyr Val
                820                 825                 830

Met Leu Glu Glu Asn Lys Gln Leu Pro Lys Met Trp Leu His Tyr Phe
            835                 840                 845

Arg Asp Trp Leu Gln Gly Leu Gln Asp Ala Phe Asp Ser Asp Trp Glu
850                 855                 860

Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                885                 890                 895

Ile Asp Ile Ser Gln Leu Thr Lys Gln Arg Leu Val Asp Ala Asp Gly
                900                 905                 910

Ile Ile Asn Pro Ser Ala Phe Tyr Ile Tyr Leu Thr Ala Trp Val Ser
            915                 920                 925

Asn Asp Pro Val Ala Tyr Ala Ala Ser Gln Ala Asn Ile Arg Pro His
930                 935                 940
```

-continued

```
Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
            965                 970                 975

Tyr Leu Asn Gly Leu Arg Asp Thr Ser Asp Phe Val Glu Ala Ile Glu
            980                 985                 990

Lys Val Arg Thr Ile Cys Ser Asn Tyr Thr Ser Leu Gly Leu Ser Ser
            995                 1000                1005

Tyr Pro Asn Gly Tyr Pro Phe Leu Phe Trp Glu Gln Tyr Ile Gly
    1010                1015                1020

Leu Arg His Trp Leu Leu Leu Phe Ile Ser Val Val Leu Ala Cys
    1025                1030                1035

Thr Phe Leu Val Cys Ala Val Phe Leu Leu Asn Pro Trp Thr Ala
    1040                1045                1050

Gly Ile Ile Val Met Val Leu Ala Leu Met Thr Val Glu Leu Phe
    1055                1060                1065

Gly Met Met Gly Leu Ile Gly Ile Lys Leu Ser Ala Val Pro Val
    1070                1075                1080

Val Ile Leu Ile Ala Ser Val Gly Ile Gly Val Glu Phe Thr Val
    1085                1090                1095

His Val Ala Leu Ala Phe Leu Thr Ala Ile Gly Asp Lys Asn Arg
    1100                1105                1110

Arg Ala Val Leu Ala Leu Glu His Met Phe Ala Pro Val Leu Asp
    1115                1120                1125

Gly Ala Val Ser Thr Leu Leu Gly Val Leu Met Leu Ala Gly Ser
    1130                1135                1140

Glu Phe Asp Phe Ile Val Arg Tyr Phe Phe Ala Val Leu Ala Ile
    1145                1150                1155

Leu Thr Ile Leu Gly Val Leu Asn Gly Leu Val Leu Leu Pro Val
    1160                1165                1170

Leu Leu Ser Phe Phe Gly Pro Tyr Pro Glu Val Ser Pro Ala Asn
    1175                1180                1185

Gly Leu Asn Arg Leu Pro Thr Pro Ser Pro Glu Pro Pro Pro Ser
    1190                1195                1200

Val Val Arg Phe Ala Met Pro Pro Gly His Thr His Ser Gly Ser
    1205                1210                1215

Asp Ser Ser Asp Ser Glu Tyr Ser Ser Gln Thr Thr Val Ser Gly
    1220                1225                1230

Leu Ser Glu Glu Leu Arg His Tyr Glu Ala Gln Gln Gly Ala Gly
    1235                1240                1245

Gly Pro Ala His Gln Val Ile Val Glu Ala Thr Glu Asn Pro Val
    1250                1255                1260

Phe Ala His Ser Thr Val Val His Pro Glu Ser Arg His His Pro
    1265                1270                1275

Pro Ser Asn Pro Arg Gln Gln Pro His Leu Asp Ser Gly Ser Leu
    1280                1285                1290

Pro Pro Gly Arg Gln Gly Gln Pro Arg Arg Asp Pro Pro Arg
    1295                1300                1305

Glu Gly Leu Trp Pro Pro Pro Tyr Arg Pro Arg Arg Asp Ala Phe
    1310                1315                1320

Glu Ile Ser Thr Glu Gly His Ser Gly Pro Ser Asn Arg Ala Arg
    1325                1330                1335
```

```
Trp Gly Pro Arg Gly Ala Arg Ser His Asn Pro Arg Asn Pro Ala
    1340                1345                1350

Ser Thr Ala Met Gly Ser Ser Val Pro Gly Tyr Cys Gln Pro Ile
    1355                1360                1365

Thr Thr Val Thr Ala Ser Ala Ser Val Thr Val Ala Val His Pro
    1370                1375                1380

Pro Pro Val Pro Gly Pro Gly Arg Asn Pro Arg Gly Gly Leu Cys
    1385                1390                1395

Pro Gly Tyr Pro Glu Thr Asp His Gly Leu Phe Glu Asp Pro His
    1400                1405                1410

Val Pro Phe His Val Arg Cys Glu Arg Arg Asp Ser Lys Val Glu
    1415                1420                1425

Val Ile Glu Leu Gln Asp Val Glu Cys Glu Glu Arg Pro Arg Gly
    1430                1435                1440

Ser Ser Ser Asn
    1445

<210> SEQ ID NO 45
<211> LENGTH: 238
<212> TYPE: PRT
<213> ORGANISM: Mus musculus

<400> SEQUENCE: 45

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Ile Gly
                20                  25                  30

Val Ala Val Gln Val Val Leu Lys Gln Ala Ile Thr His Glu Thr Thr
            35                  40                  45

Ala Gly Ser Leu Leu Pro Val Val Ile Ala Val Gly Ala Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Val Ala Ile Ala Gly Tyr Val Phe Arg Asp Gln Val Lys
                100                 105                 110

Ser Glu Phe Asn Lys Ser Phe Gln Gln Gln Met Gln Asn Tyr Leu Lys
            115                 120                 125

Asp Asn Lys Thr Ala Thr Ile Leu Asp Lys Leu Gln Lys Glu Asn Asn
130                 135                 140

Cys Cys Gly Ala Ser Asn Tyr Thr Asp Trp Glu Asn Ile Pro Gly Met
145                 150                 155                 160

Ala Lys Asp Arg Val Pro Asp Ser Cys Cys Ile Asn Ile Thr Val Gly
                165                 170                 175

Cys Gly Asn Asp Phe Lys Glu Ser Thr Ile His Thr Gln Gly Cys Val
            180                 185                 190

Glu Thr Ile Ala Ile Trp Leu Arg Lys Asn Ile Leu Leu Val Ala Ala
        195                 200                 205

Ala Ala Leu Gly Ile Ala Phe Val Glu Val Leu Gly Ile Ile Phe Ser
    210                 215                 220

Cys Cys Leu Val Lys Ser Ile Arg Ser Gly Tyr Glu Val Met
225                 230                 235

<210> SEQ ID NO 46
```

```
<211> LENGTH: 270
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 46

Met Ala Arg Gly Ile His Pro Ser Gly Val Thr Gly Leu Val Pro Ser
1               5                   10                  15

Leu Gly Asp Arg Glu Lys Arg Asp Ser Leu Cys Pro Gln Gly Lys Tyr
                20                  25                  30

Val His Ser Lys Asn Asn Ser Ile Cys Cys Thr Lys Cys His Lys Gly
            35                  40                  45

Thr Tyr Leu Val Ser Asp Cys Pro Ser Pro Gly Arg Asp Thr Val Cys
        50                  55                  60

Arg Glu Cys Glu Lys Gly Thr Phe Thr Ala Ser Gln Asn Tyr Leu Arg
65                  70                  75                  80

Gln Cys Leu Ser Cys Lys Thr Cys Arg Lys Glu Met Ser Gln Val Glu
                85                  90                  95

Ile Ser Pro Cys Gln Ala Asp Lys Asp Thr Val Cys Gly Cys Lys Glu
            100                 105                 110

Asn Gln Phe Gln Arg Tyr Leu Ser Glu Thr His Phe Gln Cys Val Asp
        115                 120                 125

Cys Ser Pro Cys Phe Asn Gly Thr Val Thr Ile Pro Cys Lys Glu Thr
    130                 135                 140

Gln Asn Thr Val Cys Asn Cys His Ala Gly Phe Phe Leu Arg Glu Ser
145                 150                 155                 160

Glu Cys Val Pro Cys Ser His Cys Lys Lys Asn Glu Glu Cys Met Lys
                165                 170                 175

Leu Cys Leu Pro Pro Pro Leu Ala Asn Val Thr Asn Pro Gln Asp Ser
            180                 185                 190

Gly Thr Ser Gly Gly Leu Tyr Arg Asp Pro Glu Ala Ala Ser Pro Gly
        195                 200                 205

Ala Pro Thr Arg Asp Val Leu Leu Val Ser Ala Ile Ile Thr Val Ser
    210                 215                 220

Leu Ser Val Thr Ile Val Leu Cys Gly Leu Cys His Trp Cys Gln Arg
225                 230                 235                 240

Lys Leu Gly Lys Arg Tyr Lys Asn Ser Leu Glu Thr Val Gly Thr Pro
                245                 250                 255

Asp Ser His His His His His His Gly Lys Leu Val Trp Ile
            260                 265                 270

<210> SEQ ID NO 47
<211> LENGTH: 611
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 47

Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
                20                  25                  30

Ser Lys Gly Thr Cys Leu Tyr Ala Arg Gly Ile His Pro Ser Gly Val
            35                  40                  45
```

-continued

```
Thr Gly Leu Val Pro Ser Leu Gly Asp Arg Glu Lys Arg Asp Ser Leu
     50                  55                  60
Cys Pro Gln Gly Lys Tyr Val His Ser Lys Asn Asn Ser Ile Cys Cys
 65                  70                  75                  80
Thr Lys Cys His Lys Gly Thr Tyr Leu Val Ser Asp Cys Pro Ser Pro
                 85                  90                  95
Gly Arg Asp Thr Val Cys Arg Glu Cys Glu Lys Gly Thr Phe Thr Ala
             100                 105                 110
Ser Gln Asn Tyr Leu Arg Gln Cys Leu Ser Cys Lys Thr Cys Arg Lys
         115                 120                 125
Glu Met Ser Gln Val Glu Ile Ser Pro Cys Gln Ala Asp Lys Asp Thr
     130                 135                 140
Val Cys Gly Cys Lys Glu Asn Gln Phe Gln Arg Tyr Leu Ser Glu Thr
145                 150                 155                 160
His Phe Gln Cys Val Asp Cys Ser Pro Cys Phe Asn Gly Thr Val Thr
                 165                 170                 175
Ile Pro Cys Lys Glu Thr Gln Asn Thr Val Cys Asn Cys His Ala Gly
             180                 185                 190
Phe Phe Leu Arg Glu Ser Glu Cys Val Pro Cys Ser His Cys Lys Lys
         195                 200                 205
Asn Glu Glu Cys Met Lys Leu Cys Leu Pro Pro Leu Ala Asn Val
     210                 215                 220
Thr Asn Pro Gln Asp Ser Gly Thr Ser Gly Gly Ala Glu Trp Glu Met
225                 230                 235                 240
Asn Phe Thr Ile Thr Tyr Glu Thr Thr Asn Gln Thr Asn Lys Thr Ile
                 245                 250                 255
Thr Ile Ala Val Pro Asp Lys Ala Thr His Asp Gly Ser Ser Cys Gly
             260                 265                 270
Asp Asp Arg Asn Ser Ala Lys Ile Met Ile Gln Phe Gly Phe Ala Val
         275                 280                 285
Ser Trp Ala Val Asn Phe Thr Lys Glu Ala Ser His Tyr Ser Ile His
     290                 295                 300
Asp Ile Val Leu Ser Tyr Asn Thr Ser Asp Ser Thr Val Phe Pro Gly
305                 310                 315                 320
Ala Val Ala Lys Gly Val His Thr Val Lys Asn Pro Glu Asn Phe Lys
                 325                 330                 335
Val Pro Leu Asp Val Ile Phe Lys Cys Asn Ser Val Leu Thr Tyr Asn
             340                 345                 350
Leu Thr Pro Val Val Gln Lys Tyr Trp Gly Ile His Leu Gln Ala Phe
         355                 360                 365
Val Gln Asn Gly Thr Val Ser Lys Asn Glu Gln Val Cys Glu Glu Asp
     370                 375                 380
Gln Thr Pro Thr Thr Val Ala Pro Ile Ile His Thr Thr Ala Pro Ser
385                 390                 395                 400
Thr Thr Thr Thr Leu Thr Pro Thr Ser Thr Pro Thr Pro Thr Pro Thr
                 405                 410                 415
Pro Thr Pro Thr Val Gly Asn Tyr Ser Ile Arg Asn Gly Asn Thr Thr
             420                 425                 430
Cys Leu Leu Ala Thr Met Gly Leu Gln Leu Asn Ile Thr Glu Glu Lys
         435                 440                 445
Val Pro Phe Ile Phe Asn Ile Asn Pro Ala Thr Thr Asn Phe Thr Gly
     450                 455                 460
```

```
Ser Cys Gln Pro Gln Ser Ala Gln Leu Arg Leu Asn Asn Ser Gln Ile
465                 470                 475                 480

Lys Tyr Leu Asp Phe Ile Phe Ala Val Lys Asn Glu Lys Arg Phe Tyr
                485                 490                 495

Leu Lys Glu Val Asn Val Tyr Met Tyr Leu Ala Asn Gly Ser Ala Phe
            500                 505                 510

Asn Ile Ser Asn Lys Asn Leu Ser Phe Trp Asp Ala Pro Leu Gly Ser
        515                 520                 525

Ser Tyr Met Cys Asn Lys Gln Val Leu Ser Val Ser Arg Ala Phe
    530                 535                 540

Gln Ile Asn Thr Phe Asn Leu Lys Val Gln Pro Phe Asn Val Thr Lys
545                 550                 555                 560

Gly Gln Tyr Ser Thr Ala Gln Glu Cys Ser Leu Asp Asp Thr Ile
                565                 570                 575

Leu Ile Pro Ile Ile Val Gly Ala Gly Leu Ser Gly Leu Ile Ile Val
                580                 585                 590

Ile Val Ile Ala Tyr Leu Ile Gly Arg Arg Lys Thr Tyr Ala Gly Tyr
            595                 600                 605

Gln Thr Leu
    610

<210> SEQ ID NO 48
<211> LENGTH: 358
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 48

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Ile Gly
                20                  25                  30

Val Ala Val Gln Val Val Leu Lys Gln Ala Ile Thr His Glu Th

```
Asp Lys Asp Thr Val Cys Gly Cys Lys Glu Asn Gln Phe Gln Arg Tyr
    210                 215                 220

Leu Ser Glu Thr His Phe Gln Cys Val Asp Cys Ser Pro Cys Phe Asn
225                 230                 235                 240

Gly Thr Val Thr Ile Pro Cys Lys Glu Thr Gln Asn Thr Val Cys Asn
                245                 250                 255

Cys His Ala Gly Phe Phe Leu Arg Glu Ser Glu Cys Val Pro Cys Ser
                260                 265                 270

His Cys Lys Lys Asn Glu Glu Cys Met Lys Leu Cys Leu Pro Pro Pro
            275                 280                 285

Leu Ala Asn Val Thr Asn Pro Gln Asp Ser Gly Thr Glu Phe Gly Gly
290                 295                 300

Ile His Thr Gln Gly Cys Val Glu Thr Ile Ala Ile Trp Leu Arg Lys
305                 310                 315                 320

Asn Ile Leu Leu Val Ala Ala Ala Leu Gly Ile Ala Phe Val Glu
                325                 330                 335

Val Leu Gly Ile Ile Phe Ser Cys Cys Leu Val Lys Ser Ile Arg Ser
                340                 345                 350

Gly Tyr Glu Val Met Asp
            355

<210> SEQ ID NO 49
<211> LENGTH: 503
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 49

Met Ala Arg Gly Ile His Pro Ser Gly Val Thr Gly Leu Val Pro Ser
1               5                   10                  15

Leu Gly Asp Arg Glu Lys Arg Asp Ser Leu Cys Pro Gln Gly Lys Tyr
                20                  25                  30

Val His Ser Lys Asn Asn Ser Ile Cys Cys Thr Lys Cys His Lys Gly
            35                  40                  45

Thr Tyr Leu Val Ser Asp Cys Pro Ser Pro Gly Arg Asp Thr Val Cys
        50                  55                  60

Arg Glu Cys Glu Lys Gly Thr Phe Thr Ala Ser Gln Asn Tyr Leu Arg
65                  70                  75                  80

Gln Cys Leu Ser Cys Lys Thr Cys Arg Lys Glu Met Ser Gln Val Glu
                85                  90                  95

Ile Ser Pro Cys Gln Ala Asp Lys Asp Thr Val Cys Gly Cys Lys Glu
            100                 105                 110

Asn Gln Phe Gln Arg Tyr Leu Ser Glu Thr His Phe Gln Cys Val Asp
        115                 120                 125

Cys Ser Pro Cys Phe Asn Gly Thr Val Thr Ile Pro Cys Lys Glu Thr
    130                 135                 140

Gln Asn Thr Val Cys Asn Cys His Ala Gly Phe Phe Leu Arg Glu Ser
145                 150                 155                 160

Glu Cys Val Pro Cys Ser His Cys Lys Lys Asn Glu Glu Cys Met Lys
                165                 170                 175

Leu Cys Leu Pro Pro Pro Leu Ala Asn Val Thr Asn Pro Gln Asp Ser
            180                 185                 190

Gly Thr Ser Gly Gly Gly Ser Met

```
                195                 200                 205

Pro Gly Ala Pro Thr Arg Asp Val Leu Leu Val Ser Ala Ile Ile Thr
    210                 215                 220

Val Ser Leu Ser Val Thr Ile Val Leu Cys Gly Leu Cys His Trp Cys
225                 230                 235                 240

Gln Arg Lys Leu Gly Lys Arg Tyr Lys Asn Ser Leu Glu Thr Val Gly
                245                 250                 255

Thr Pro Asp Leu Pro Val Ala Thr Met Val Ser Lys Gly Glu Glu Leu
            260                 265                 270

Phe Thr Gly Val Val Pro Ile Leu Val Glu Leu Asp Gly Asp Val Asn
        275                 280                 285

Gly His Lys Phe Ser Val Ser Gly Glu Gly Glu Gly Asp Ala Thr Tyr
    290                 295                 300

Gly Lys Leu Thr Leu Lys Phe Ile Cys Thr Thr Gly Lys Leu Pro Val
305                 310                 315                 320

Pro Trp Pro Thr Leu Val Thr Thr Leu Thr Tyr Gly Val Gln Cys Phe
                325                 330                 335

Ser Arg Tyr Pro Asp His Met Lys Gln His Asp Phe Phe Lys Ser Ala
            340                 345                 350

Met Pro Glu Gly Tyr Val Gln Glu Arg Thr Ile Phe Phe Lys Asp Asp
        355                 360                 365

Gly Asn Tyr Lys Thr Arg Ala Glu Val Lys Phe Glu Gly Asp Thr Leu
    370                 375                 380

Val Asn Arg Ile Glu Leu Lys Gly Ile Asp Phe Lys Glu Asp Gly Asn
385                 390                 395                 400

Ile Leu Gly His Lys Leu Glu Tyr Asn Tyr Asn Ser His Asn Val Tyr
                405                 410                 415

Ile Met Ala Asp Lys Gln Lys Asn Gly Ile Lys Val Asn Phe Lys Ile
            420                 425                 430

Arg His Asn Ile Glu Asp Gly Ser Val Gln Leu Ala Asp His Tyr Gln
        435                 440                 445

Gln Asn Thr Pro Ile Gly Asp Gly Pro Val Leu Leu Pro Asp Asn His
    450                 455                 460

Tyr Leu Ser Thr Gln Ser Ala Leu Ser Lys Asp Pro Asn Glu Lys Arg
465                 470                 475                 480

Asp His Met Val Leu Leu Glu Phe Val Thr Ala Ala Gly Ile Thr Leu
                485                 490                 495

Gly Met Asp Glu Leu Tyr Lys
            500

<210> SEQ ID NO 50
<211> LENGTH: 448
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 50

Met Ala Arg Ala Pro Trp Val Ala Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45
```

-continued

Arg Cys Glu Gly Glu Gln Asp Lys Arg Leu His Cys Tyr Ala Ser Trp
50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Ala Pro Thr Leu Leu Thr Val Leu Ala Tyr Ser Leu
130                 135                 140

Leu Pro Ile Gly Gly Leu Ser Leu Ile Val Leu Leu Ala Phe Trp Met
145                 150                 155                 160

Tyr Arg His Arg Lys Ser Gly Lys Asp Glu Gly Ser Tyr Ser Leu
            165                 170                 175

Glu Glu Pro Lys Gln Ala Asn Gly Gly Ala Tyr His Lys Pro Thr Lys
            180                 185                 190

Gln Asp Glu Phe Tyr Ala Gly Gly His His His His His Glu
        195                 200                 205

Phe Ser Lys Gly Glu Glu Leu Phe Thr Gly Val Val Pro Ile Leu Val
210                 215                 220

Glu Leu Asp Gly Asp Val Asn Gly His Lys Phe Ser Val Ser Gly Glu
225                 230                 235                 240

Gly Glu Gly Asp Ala Thr Tyr Gly Lys Leu Thr Leu Lys Phe Ile Cys
                245                 250                 255

Thr Thr Gly Lys Leu Pro Val Pro Trp Pro Thr Leu Val Thr Thr Leu
            260                 265                 270

Thr Tyr Gly Val Gln Cys Phe Ser Arg Tyr Pro Asp His Met Lys Gln
        275                 280                 285

His Asp Phe Phe Lys Ser Ala Met Pro Glu Gly Tyr Val Gln Glu Arg
        290                 295                 300

Thr Ile Phe Phe Lys Asp Asp Gly Asn Tyr Lys Thr Arg Ala Glu Val
305                 310                 315                 320

Lys Phe Glu Gly Asp Thr Leu Val Asn Arg Ile Glu Leu Lys Gly Ile
            325                 330                 335

Asp Phe Lys Glu Asp Gly Asn Ile Leu Gly His Lys Leu Glu Tyr Asn
        340                 345                 350

Tyr Asn Ser His Asn Val Tyr Ile Met Ala Asp Lys Gln Lys Asn Gly
        355                 360                 365

Ile Lys Val Asn Phe Lys Ile Arg His Asn Ile Glu Asp Gly Ser Val
370                 375                 380

Gln Leu Ala Asp His Tyr Gln Gln Asn Thr Pro Ile Gly Asp Gly Pro
385                 390                 395                 400

Val Leu Leu Pro Asp Asn His Tyr Leu Ser Thr Gln Ser Ala Leu Ser
                405                 410                 415

Lys Asp Pro Asn Glu Lys Arg Asp His Met Val Leu Leu Glu Phe Val
            420                 425                 430

Thr Ala Arg Arg Asp His Ser Arg His Gly Arg Ala Val Gln Gly Ile
        435                 440                 445

<210> SEQ ID NO 51
<211> LENGTH: 540
<212> TYPE: PRT

<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 51

```
Met Cys Leu Ser Pro Val Lys Gly Ala Lys Leu Ile Leu Ile Phe Leu
1               5                   10                  15

Phe Leu Gly Ala Val Gln Ser Asn Ala Leu Ile Val Asn Leu Thr Asp
            20                  25                  30

Ser Lys Gly Thr Cys Leu Tyr Ala Arg Gly Ser Gly Arg Gly Glu Ala
        35                  40                  45

Glu Thr Arg Glu Cys Ile Tyr Tyr Asn Ala Asn Trp Glu Leu Glu Arg
    50                  55                  60

Thr Asn Gln Ser Gly Leu Glu Arg Cys Glu Gly Glu Gln Asp Lys Arg
65                  70                  75                  80

Leu His Cys Tyr Ala Ser Trp Arg Asn Ser Ser Gly Thr Ile Glu Leu
                85                  90                  95

Val Lys Lys Gly Cys Trp Leu Asp Asp Phe Asn Cys Tyr Asp Arg Gln
            100                 105                 110

Glu Cys Val Ala Thr Glu Glu Asn Pro Gln Val Tyr Phe Cys Cys Cys
        115                 120                 125

Glu Gly Asn Phe Cys Asn Glu Arg Phe Thr His Leu Pro Glu Ala Gly
130                 135                 140

Gly Pro Glu Val Thr Tyr Glu Pro Pro Thr Ala Pro Thr Leu Leu
145                 150                 155                 160

Thr Ser Gly Gly Ala Glu Trp Glu Met Asn Phe Thr Ile Thr Tyr Glu
                165                 170                 175

Thr Thr Asn Gln Thr Asn Lys Thr Ile Thr Ile Ala Val Pro Asp Lys
            180                 185                 190

Ala Thr His Asp Gly Ser Ser Cys Gly Asp Asp Arg Asn Ser Ala Lys
        195                 200                 205

Ile Met Ile Gln Phe Gly Phe Ala Val Ser Trp Ala Val Asn Phe Thr
210                 215                 220

Lys Glu Ala Ser His Tyr Ser Ile His Asp Ile Val Leu Ser Tyr Asn
225                 230                 235                 240

Thr Ser Asp Ser Thr Val Phe Pro Gly Ala Val Ala Lys Gly Val His
                245                 250                 255

Thr Val Lys Asn Pro Glu Asn Phe Lys Val Pro Leu Asp Val Ile Phe
            260                 265                 270

Lys Cys Asn Ser Val Leu Thr Tyr Asn Leu Thr Pro Val Val Gln Lys
        275                 280                 285

Tyr Trp Gly Ile His Leu Gln Ala Phe Val Gln Asn Gly Thr Val Ser
290                 295                 300

Lys Asn Glu Gln Val Cys Glu Glu Asp Gln Thr Pro Thr Thr Val Ala
305                 310                 315                 320

Pro Ile Ile His Thr Thr Ala Pro Ser Thr Thr Thr Thr Leu Thr Pro
                325                 330                 335

Thr Ser Thr Pro Thr Pro Thr Pro Thr Pro Thr Pro Thr Val Gly Asn
            340                 345                 350

Tyr Ser Ile Arg Asn Gly Asn Thr Thr Cys Leu Leu Ala Thr Met Gly
        355                 360                 365

Leu Gln Leu Asn Ile Thr Glu Glu Lys Val Pro Phe Ile Phe Asn Ile
370                 375                 380
```

```
Asn Pro Ala Thr Thr Asn Phe Thr Gly Ser Cys Gln Pro Gln Ser Ala
385                 390                 395                 400

Gln Leu Arg Leu Asn Asn Ser Gln Ile Lys Tyr Leu Asp Phe Ile Phe
            405                 410                 415

Ala Val Lys Asn Glu Lys Arg Phe Tyr Leu Lys Glu Val Asn Val Tyr
            420                 425                 430

Met Tyr Leu Ala Asn Gly Ser Ala Phe Asn Ile Ser Asn Lys Asn Leu
            435                 440                 445

Ser Phe Trp Asp Ala Pro Leu Gly Ser Ser Tyr Met Cys Asn Lys Glu
            450                 455                 460

Gln Val Leu Ser Val Ser Arg Ala Phe Gln Ile Asn Thr Phe Asn Leu
465                 470                 475                 480

Lys Val Gln Pro Phe Asn Val Thr Lys Gly Gln Tyr Ser Thr Ala Gln
            485                 490                 495

Glu Cys Ser Leu Asp Asp Thr Ile Leu Ile Pro Ile Ile Val Gly
            500                 505                 510

Ala Gly Leu Ser Gly Leu Ile Ile Val Ile Val Ile Ala Tyr Leu Ile
            515                 520                 525

Gly Arg Arg Lys Thr Tyr Ala Gly Tyr Gln Thr Leu
530                 535                 540

<210> SEQ ID NO 52
<211> LENGTH: 199
<212> TYPE: PRT
<213> ORGANISM: Artificial Sequence
<220> FEATURE:
<223> OTHER INFORMATION: Designed construct comprising a carrier
      polypeptide fused to a therapeutic polypeptide decoy receptor

<400> SEQUENCE: 52

Met Ala Arg Gly Ser Gly Arg Gly Glu Ala Glu Thr Arg Glu Cys Ile
1               5                   10                  15

Tyr Tyr Asn Ala Asn Trp Glu Leu Glu Arg Thr Asn Gln Ser Gly Leu
            20                  25                  30

Glu Arg Cys Glu Gly Glu Gln Asp Lys Arg Leu His Cys Tyr Ala Ser
            35                  40                  45

Trp Arg Asn Ser Ser Gly Thr Ile Glu Leu Val Lys Lys Gly Cys Trp
50                  55                  60

Leu Asp Asp Phe Asn Cys Tyr Asp Arg Gln Glu Cys Val Ala Thr Glu
65                  70                  75                  80

Glu Asn Pro Gln Val Tyr Phe Cys Cys Cys Glu Gly Asn Phe Cys Asn
            85                  90                  95

Glu Arg Phe Thr His Leu Pro Glu Ala Gly Gly Pro Glu Val Thr Tyr
            100                 105                 110

Glu Pro Pro Pro Thr Ala Pro Thr Leu Leu Thr Ser Gly Gly Leu Tyr
            115                 120                 125

Arg Asp Pro Glu Ala Ala Ser Pro Gly Ala Pro Thr Arg Asp Val Leu
            130                 135                 140

Leu Val Ser Ala Ile Ile Thr Val Ser Leu Ser Val Thr Ile Val Leu
145                 150                 155                 160

Cys Gly Leu Cys His Trp Cys Gln Arg Lys Leu Gly Lys Arg Tyr Lys
            165                 170                 175
```

```
Asn Ser Leu Glu Thr Val Gly Thr Pro Asp Ser His His His His
            180                 185                 190
His Gly Lys Leu Val Trp Ile
        195
```

THERAPEUTIC DELIVERY VESICLES

CROSS-REFERENCE TO RELATED APPLICATIONS

This application is a divisional of U.S. application Ser. No. 14/784,015, filed on Oct. 12, 2015, which is a national stage application filed under 35 U.S.C. § 371, of International Application No. PCT/SE2014/000047, filed Apr. 10, 2014, which claims priority to Sweden Patent Application No. 1300271-2, filed Apr. 12, 2013. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Feb. 19, 2020, is named "EVOX-001_D01US_SeqList.txt" and is 261 KB in size.

TECHNICAL FIELD

The present invention pertains, inter alia, to therapeutic delivery vesicles, for instance exosomes or microvesicles, comprising polypeptide constructs, methods for producing said therapeutic delivery vesicles, pharmaceutical compositions and medical uses thereof.

BACKGROUND ART

Exosomes and microvesicles are membrane-bound vesicles that differ based on their process of biogenesis and biophysical properties, including size and surface protein markers. Exosomes are homogenous small particles ranging from 40 to 150 nm in size and they are normally derived from the endocytic recycling pathway. In endocytosis, endocytic vesicles form at the plasma membrane and fuse to form early endosomes. These mature and become late endosomes where intraluminal vesicles bud off into an intra-vesicular lumen. Instead of fusing with the lysosome, these multivesicular bodies directly fuse with the plasma membrane and release exosomes into the extracellular space. Exosome biogenesis, protein cargo sorting, and release involve the endosomal sorting complex required for transport (ESCRT complex) and other associated proteins such as Alix and Tsg101.

In contrast, another type of extracellular vesicles, namely microvesicles, are produced directly through the outward budding and fission of membrane vesicles from the plasma membrane, and hence, their surface markers are largely dependent on the composition of the membrane of origin. Further, they tend to constitute a larger and more heterogeneous population of extracellular vesicles, ranging from 150 to 1000 nm in diameter. However, both types of vesicles have been shown to deliver functional mRNA, miRNA and proteins to recipient cells.

To maintain a physiological balance in receptor signalling and response several receptors exists both in a membrane bound form and in a soluble form. The membrane form is normally capable of signalling, whereas the soluble form is signalling-incompetent. The soluble form often occurs as the extracellular part of the membrane-bound form. The soluble part is generated in two different ways: (1) alternative splicing of the pre-mRNA, and (2) by cleavage of extracellular proteases (often metalloproteases). The soluble form binds its ligand and thereby sequesters the ligand, inhibiting its binding with the membrane-bound form, meaning that the overall signalling from that pathway will decrease. The soluble form often increases when the signalling pathway is very active. For instance, the soluble forms of the two tumour necrosis factor receptor alpha (TNFRαs) increase in pathological conditions such as sepsis and inflammation in order to reduce the inflammatory process.

Decoy receptors have received substantial interest from a therapeutic point of view, since they provide a highly specific and tailored approach to decrease the physiological concentration of a protein of interest. The therapeutic modality is reliant on administration of decoy receptors in order to decrease the activity of a particular signaling pathway. Decoy receptors are often fused with the Fc-part of an antibody to increase their half-life and to increase the avidity of the receptors when two come in close range from each other. One example of this strategy is Etanercept, which is the sTNFR2 fused with an Fc-fragment. Etanercept is clinically approved for treating rheumatoid arthritis, psoriatic arthritis, ankylosing spondylitis and moderately to severely active polyarticular juvenile idiopathic arthritis, and it has been shown to be safe and effective over the last 19 years since its initial approval. Several other decoy receptor fusion proteins are in clinical trials, targeting for example VEGF, EGF, FGF and angiopoietin.

Although successfully applied in various therapeutic contexts and for a large number of ailments, decoy receptors and other biologics (biopharmaceuticals) suffer from a number of drawbacks relating to for instance pharmacokinetics, toxicity, pharmacodynamics, and therapeutic efficacy.

SUMMARY OF THE INVENTION

It is hence an object of the present invention to overcome the above-identified problems associated with the use of biologics, and specifically decoy receptors, and to satisfy the existing needs within the art, namely to provide for optimized therapeutic efficacy, significantly improved pharmacokinetics, as well as reduced side-effects of biopharmaceutical polypeptides, such as decoy receptors and biologics (biopharmaceuticals) in general.

Thus, the present invention pertains to, in a first aspect, a therapeutic delivery vesicle having attached to its membrane a polypeptide construct, wherein the polypeptide construct comprises at least one carrier polypeptide fused to at least one therapeutic polypeptide decoy receptor present at least partially on the outside of the delivery vesicle, and wherein the at least one therapeutic polypeptide decoy receptor is signalling-incompetent, i.e not capable of transmitting signals it transmits under normal circumstances. Normally the decoy receptor binds to and sequesters a circulating ligand or a ligand that may in fact also be present inside a target cell and/or on the surface of a target cell. Without wishing to be bound by any theory, it is surmised that therapeutic polypeptide decoy receptor present on the surface of therapeutic delivery vesicle sequesters its interaction partner(s), i.e. the target and/or ligand, in virtually the same manner as the free therapeutic polypeptide decoy receptor, albeit with a significantly improved half-life, reduced clearance, decreased side-effects, and generally significantly enhanced pharmacokinetics, and therapeutic efficacy, by virtue of its attachment on a suitable delivery vesicle, for instance an exosome, a microvesicle, an apoptotic body, a liposome, or any other type of naturally derived or artificially produced vesicle. The at least one therapeutic polypeptide decoy receptor present on the therapeutic delivery vesicle may be partially or completely devoid of its signalling domain, so as to make it a signalling-incompetent therapeutic polypeptide receptor, and the signalling domain may be partially or completely replaced by the carrier polypeptide, but the incapacity to contribute to signalling may also derive from alterations in the polypeptide sequence. For instance, in various embodiments of the present invention it may be sufficient to replace certain amino acids to render the therapeutic polypeptide receptor signalling-incompetent, and/or the therapeutic polypeptide receptor may be rendered signalling-incompetent merely by attaching the decoy receptor to the carrier polypeptide (using recombinant technology) which is transporting the entire polypeptide construct to the surface of the extracellular vesicle.

Importantly, exosomes and other types of cell-derived vesicles (which constitute a conceivable source of delivery vesicles in accordance with the present invention) may have therapeutic activities per se. For example, vesicles derived from e.g. mesenchymal stem cells but also from other cells are known to be innately immunosuppressive as they carry several miRNAs, proteins and bioactive lipids that for instance suppress cytotoxic T-cells and trigger expansion of regulatory T-cells. The repressive effect on the immune system is a prerequisite also for subsequent tissue regeneration following tissue injury. Hence, choosing for instance an appropriate source of cells for derivation of exosomes and/or other types of extracellular vesicles will provide an additional therapeutic advantage as compared to using receptor decoys/monoclonal antibodies (such as etanercept and infliximab) only.

In further aspects, the instant invention relates to therapeutic delivery vesicles and pharmaceutical compositions comprising the vesicles in accordance with the present invention for use in medicine, and more specifically for use in the treatment, alleviation, and/or prophylaxis of various diseases and disorders that may be treated using biopharmaceutical therapeutics (biologics).

Thus, the present invention essentially pertains to the use of exosomes and other vesicles (notably derivable from cellular and/or biological sources, but alternatively also artificially produced vesicles such as liposomes) as delivery or administration vehicles for biopharmaceuticals, specifically polypeptide-based biologics, and more specifically decoy receptors (also known as sink receptors). The present invention hence relates to the use of exosomes (and other types of vesicles) comprising various polypeptides, as defined herein, in the treatment of a large number of diseases and disorders, as herein disclosed.

In additional aspects, the instant invention pertains to methods of producing the therapeutic delivery vesicles of the present invention, generally comprising the steps of (i) providing at least one polynucleotide construct encoding at least one therapeutic polypeptide decoy receptor (which is preferably signalling-incompetent, for instance via being partially or completely devoid of its signalling domain) that binds to a suitable target and/or ligand, (ii) introducing said at least one polynucleotide construct into a cell capable of producing exosomes, and, (iii) collecting (harvesting) at least one delivery vesicle produced by the cell of step (ii). The present invention also relates to delivery vesicles produced by said methods, as well as various aspects and embodiments related to kits, compositions, and cell culture media in accordance with the present invention.

In further aspects, the present invention relates to methods for increasing the yield of extracellular vesicles (which may be in their native form, i.e. completely free from therapeutic polypeptide constructs) comprising exposing the cells (which are the source of the extracellular vesicles) to inhibitors of autophagy. In yet a further aspect, the present invention pertains to methods for increasing the regenerative capacity of extracellular vesicles, by exposing the cell source to stress-inducing conditions (for instance oxygen deprivation and/or serum starvation). Exposure of vesicle-producing cells to stress-inducing conditions results in enrichment of metabolically active proteins and/or anti-apoptotic proteins, which leads to enhanced regenerative effects.

The present invention thus provides delivery vesicles, methods, compositions, and uses, as well as various other aspects and embodiments, for improving the delivery, administration, and characteristics of e.g. biopharmaceutical polypeptide agents. The present invention results in optimized therapeutic efficacy (for instance due to therapeutic polypeptide decoy receptor multivalency and the inherent regenerative therapeutic effects of exosomes per se), significantly improved pharmacokinetics (via e.g. reduced renal clearance), improved biodistribution to certain organs, such as the brain, as well as reduced side-effects of biopharmaceutical polypeptides (via e.g. fusion with recipient cells to confer direct cellular protection), such as decoy receptors and other types of biologics.

BRIEF DESCRIPTION OF THE DRAWINGS

FIG. 6 shows the amino acid sequences of various polypeptide constructs as per the present invention. Some of the constructs comprise His tags (for facilitated purification) whereas others comprise EGFP (to facilitate detection) but the constructs may naturally be applied both with and without said additional moieties/sequences.

DETAILED DESCRIPTION OF THE INVENTION

Figure 1:
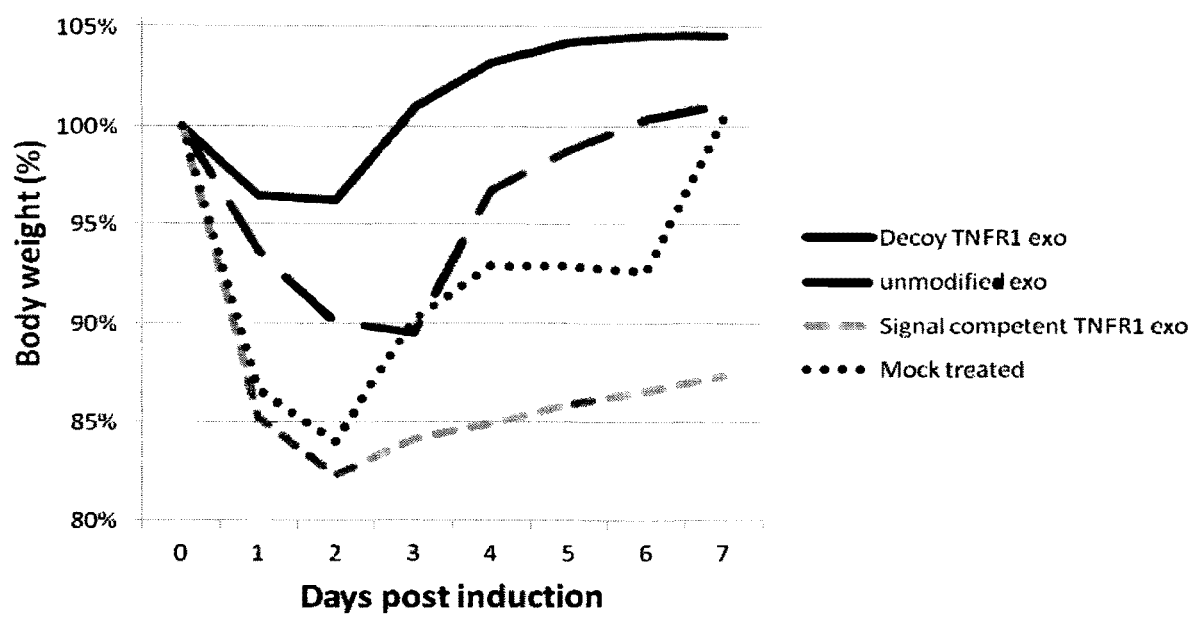
FIG. 1 shows treatment efficacy, in a mouse colitis model, of exosomes comprising a signalling-incompetent therapeutic polypeptide decoy receptor, which is comprised of a signalling-incompetent soluble tumour necrosis factor receptor 1 (sTNFR1) (which may be either one of sTNFR 1A (SEQ ID No 30) or sTNFR 1B (SEQ ID No 31)), fused to the carrier polypeptide CD63 (SEQ ID No 14). The exosomes displaying signalling-incompetent sTNFR1-CD63 successfully treat the induced colitis (solid black line) with only a minor initial loss in body weight. Signalling-competent exosomes (short-dashed grey line) show clear anti-therapeutic efficacy since they deliver more signalling receptors to the cells, whereas mock-treated mice (dotted line) did not display any clinically relevant efficacy. Unmodified exosomes (i.e. exosomes devoid of any artificially introduced polypeptide constructs) (long-dashed grey line) also induced moderate colitis remission, probably due to their inherent anti-inflammatory effects.

The present invention pertains inter alia to, in a first aspect, a therapeutic delivery vesicle having attached to its membrane a polypeptide construct, wherein the polypeptide construct comprises at least one carrier polypeptide fused to at least one therapeutic polypeptide decoy receptor present at least partially on the outside of the delivery vesicle, and wherein the at least one therapeutic polypeptide decoy receptor binds to a circulating ligand. In further aspects, the instant invention relates to delivery vesicles and pharmaceutical compositions in accordance with the present invention for use in medicine, as well as to methods of producing delivery vesicles, kits, compositions, and cell culture media.

Where features, embodiments, or aspects of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the at least one therapeutic polypeptide decoy receptor described in connection with therapeutic delivery vesicles is to be understood to be potentially relevant/applicable/present also in the context of the methods of producing delivery vesicles or in the context of the pharmaceutical compositions, or in connection with the polypeptide and/or polynucleotide constructs as per the present invention. Furthermore, certain embodiments described in connection with certain aspects, for instance the administration routes of the therapeutic delivery vesicles, as described in relation to aspects pertaining to treating certain medical indications, may naturally also be relevant in connection with other aspects and/or embodiment such as aspects/embodiments pertaining to the pharmaceutical compositions of the present invention. As a general remark, the therapeutic polypeptide decoy receptors and the carrier polypeptides in accordance with the present invention may be freely combined in any and all possible combinations without deviating from the scope and the gist of the invention, and the sequences may deviate strongly from the original sequences as long as any given carrier polypeptide retains its ability to carry the therapeutic polypeptide decoy receptor to the surface of an extracellular vesicle, and as long as any given therapeutic polypeptide decoy receptor retains its ability to bind to its target in a therapeutically efficacious manner. As long as their biological properties are retained the polypeptide sequences may deviate with as much as 50% (calculated using for instance BLAST or ClustalW) as compared to the native polypeptide, although a sequence identity that is as high as possible is preferable. The combination (fusion) of the carrier and the decoy receptor polypeptides implies that certain segments of the respective polypeptides may be replaced and/or modified, meaning that the deviation from the native sequence may be large as long as the key properties are conserved.

For convenience and clarity, certain terms employed herein are collected and described below. Unless otherwise defined, all technical and scientific terms used herein have the same meaning as commonly understood by one of ordinary skill in the art to which this invention belongs.

The term "therapeutic delivery vesicle", interchangeably termed "delivery vesicle", shall be understood to relate to any type of vesicle that is, for instance, obtainable from a cell, for instance a microvesicle (any vesicle shedded from the plasma membrane of a cell), an exosome (any vesicle derived from the endo-lysosomal pathway), an apoptotic body (from apoptotic cells), a microparticle (which may be derived from e.g. platelets), an ectosome (derivable from e.g. neutrophiles and monocytes in serum), prostatosome (obtainable from prostate cancer cells), cardiosomes (derivable from cardiac cells) etc. Furthermore, the terms "therapeutic delivery vesicle" and "delivery vesicle" shall also be understood to potentially also relate to lipoprotein particles, such as LDL, VLDL, HDL and chylomicrons, as well as liposomes, lipid-like particles, lipidoids, etc. Essentially, the present invention may relate to any type of lipid-based structure (vesicular or with any other type of suitable morphology) that can act as a delivery or transport vehicle for the therapeutics polypeptide construct(s).

The term "attached to its membrane" shall be understood as attached in the sense of how a biological polypeptide is normally attached to a vesicular membrane, i.e. predominantly via non-covalent interactions but possibly also via covalent bonds. The attachment to the membrane may comprise attachment inside the vesicle, in the vesicle membrane, on the outside of the vesicle, or any combination thereof. A typical example of a polypeptide being "attached" to the membrane of a vesicle is a transmembrane polypeptide that spans the bi-layer vesicular membrane of an exosome from the intra-exosomal space out through the exosomal membrane to the extra-exosomal milieu.

The term "polypeptide construct" (or interchangeably "therapeutic polypeptide construct") shall be understood to relate to any polypeptide that comprises a "carrier polypeptide", as defined herein, and a "therapeutic polypeptide decoy receptor", as defined herein. The polypeptide construct may be attached to the membrane of the delivery vesicle in accordance with the present invention, preferably in a transmembrane manner (i.e. with the polypeptide construct extending from the inside of the delivery vesicle, through the delivery vesicle membrane, to the outside of the delivery vesicle). When the therapeutic polypeptide decoy receptor is having a transmembrane configuration it may be preferable if the carrier polypeptide is present substantially on the inside of the delivery vesicle whereas the therapeutic polypeptide decoy receptor is present at least partially on the outside of the delivery vesicle, to be able to exert its therapeutic effect.

The term "signalling-incompetent" shall be understood as not capable of transmitting biochemical signals, i.e. a polypeptide that is signalling-incompetent is merely binding its extracellular interaction partner but upon binding no signals (i.e. no intracellular, no intravesicular, or no extracellular) are being generated or transmitted. For example, in the case of the soluble TNFR (sTNFR), even if transferred to immune cells a signalling-incompetent TNFR cannot exert a biological response as it lacks crucial signalling components. Similarly, mimics of the EGFR (SEQ ID No 18) may lack the transmembrane domain which prohibits insertion into the membrane of recipient cells, thereby not being able to transmit biological signals, e.g. in the event of a transfer to a recipient cell. Importantly in a clinical context, in the case of TNFr, transfer a of signalling incompetent receptor to recipient cells offer another layer of protection as they then directly protect the cells from excessive TNF signalling by competing for ligand binding. For clarity, both the therapeutic polypeptide decoy receptor and/or the entire polypeptide construct may be signalling-incompetent. For instance, the therapeutic polypeptide decoy receptor may be rendered signalling-incompetent through e.g. a site-specific mutation, but a signalling-competent therapeutic polypeptide receptor may be made signalling-incompetent through replacement of and/or attachment to its signalling-domain by a carrier polypeptide.

The term "carrier polypeptide" shall be understood to relate to any polypeptide that can be utilized to transport a polypeptide construct to a suitable vesicular location. More specifically, the term "carrier polypeptide" shall be understood as comprising any polypeptide that enables transporting or shuttling of a polypeptide construct (which said "carrier polypeptide" forms part of) to, at least partially, the vesicular membrane and, at least partially, the extra-vesicular side (for instance the surface) of a delivery vesicle in accordance with the present invention. Examples of carrier polypeptides are for instance Lamp2b (SEQ ID No 22), CD9 (SEQ ID No 12), CD81 (SEQ ID No 13), CD63, syndecan, ALIX (SEQ ID No 28), syntenin (SEQ ID No 29), and synaptotagmin, but numerous other polypeptides capable of transporting a polypeptide construct at least partially to the extra-vesicular side of delivery vesicle are comprised within the scope of the present invention.

The terms "therapeutic polypeptide decoy receptor", "polypeptide decoy receptor", and "decoy receptor" are used interchangeably herein and shall be understood to relate to any polypeptide (often called a decoy or a sink receptor) that can be utilized for therapeutic purposes through sequestering (binding) a suitable target and/or ligand (normally a circulating ligand or a ligand present on a cell that is itself in circulation but potentially any ligand on the surface of and/or inside a target cell), thereby exerting its therapeutic effect. The decoy receptor binds to and/or sequesters its target, which in essence inhibits the target from carrying out its function which may contribute to a disease and/or disorder to be treated. The signal transduction processes of the major receptor classes are described in some detail below, to exemplify certain therapeutic polypeptide decoy receptors in accordance with the present invention. However, as above-mentioned, the decoy receptors of the present invention are preferably signalling-incompetent, to ensure therapeutic efficacy and safety.

The terms "ligand" and "target" in the context of the present invention shall be understood to comprise any molecule that is bound (normally with high affinity, e.g. a Kd of less than 100 μM but preferably below 1 μM or more preferably below 100 nM or even more preferably below 100 nM) by the therapeutic polypeptide decoy receptors according to the instant invention. The ligand (which may be any polypeptide or carbohydrate/polysaccharide or essentially any molecule, for instance present on the surface of a cell) is normally circulating freely in the blood or in any other bodily fluid (TNFα is an example of such a freely circulating polypeptide ligand for the TNFα receptor) but it may also be a polypeptide or any other type of molecule present on a cell and/or inside a cell which circulates in a bodily fluid, for instance blood. An example of a cell-bound target may be CD19, which is present on a circulating B cells, and which can be bound by a therapeutic polypeptide receptor such as the commercially available rituximab. The term "ligand" shall thus be understood to comprise both polypeptide and non-polypeptide molecules (for instance carbohydrates or any other type of molecule).

The phrase "binds to a ligand/target" shall be understood as the therapeutic polypeptide decoy receptor having the capacity to bind to a ligand and/or a target in the human and/or animal body, meaning that the decoy receptor may bind to and sequester its ligand, to exert a therapeutic effect by inhibiting the ligand/target from carrying out its normal physiological function. The ligand/target is normally circulating in the blood stream or is exposed to the extracellular environment through being present on the surface of a target cell.

Signal transduction normally occurs in vivo when an extracellular ligand binds to a cell surface receptor and activates it. In turn the receptor changes intracellular proteins/molecules, which starts a signalling pathway. There are two main receptor groups; extracellular receptors and intracellular receptors. The extracellular receptors can be further divided into different classes:

1. G-protein coupled (7-TM) receptors
2. Tyrosine and histidine kinases
3. Integrins
4. Toll gate receptors
5. Ligand-gated ion channel 7-TM receptors have 7 transmembrane regions and are linked to a heterotrimeric G-protein. Upon ligand binding the receptor undergoes a conformational change and the G-protein becomes active. The activated G protein subunits detaches from the receptor and initiate signaling via many downstream effector proteins such as phospholipases and ion channels. Adrenergic- and chemokine receptors belong to this family. 7-TM receptors can be made signaling-incompetent by removing the binding site for the G-proteins. For instance, replacing the intracellular binding site of G-proteins with the syntenin binding site of Syndecans would direct a signaling-incompetent receptor to an exosome.

Tyrosine kinase receptors (RTKs) are transmembrane proteins with an intracellular kinase domain and an extracellular ligand-binding domain. Examples of ligands are growth factors, insulin, etc. To induce a signal the RTKs need to form dimers at the plasma membrane. When a dimer is formed the interaction between the intracellular domains initiates auto-phosphorylation of the tyrosine residues which causes a conformational change in the receptor. The kinase domains of the receptors are subsequently activated and phosphorylate downstream signaling molecules that create a signaling cascade.

The tyrosine receptors can be made signaling-incompetent by removing or mutating the kinase domain or the tyrosine domain. This can be done in a similar manner as with the 7-TM receptors. Further, the extracellular domain of tyrosine receptors could be fused with an exosomal protein, such as CD63, Lamp2b, etc.

Integrins are transmembrane proteins that are important for cell attachment to other cells as well as to the extracellular matrix. The integrins also take part in the transduction of signals from the extracellular matrix proteins such as fibronectin and collagen. Integrins change their conformation upon ligand binding; integrins lack a kinase domain which means the integrins need adaptor molecules to relay the signal into the cell. There are several adaptor molecules and integrin-linked kinases. The integrins can exist in two different conformations: an inactive form and an active form. The inactive form is common on non-activated leucocytes; when the leucocytes are activated the cell changes its integrins to an active state. Integrins are signaling incompetent without its adaptor molecules, so the binding sites for the adaptor molecules and kinases can be removed to render the receptors signaling-incompetent.

Toll-like receptors have four known adaptor molecules which are activated upon ligand binding. This four adaptor molecules, Myd88, TIRAP, TRIF, and TRAM, subsequently activate intracellular molecules, and the Toll-like receptors inhibit or activates thousands of genes when activated. The Toll-like receptors can be made signaling-incompetent through removal of either the binding site and/or the interaction sites for the adaptor molecules.

The various polypeptides mentioned in the present application (for instance carrier polypeptides such as Lamp2b or CD63, and therapeutic polypeptide decoy receptors such as sTNFR or VEGFR, etc.) shall be understood to relate also to homologous polypeptides having sequence identities to the polypeptide in question preferably above 50%, more preferably above 60%, more preferably above 70%, more preferably above 80%, and more preferably above 90%.

In a first aspect, the present invention relates to a therapeutic delivery vesicle having attached to its membrane a polypeptide construct, wherein the polypeptide construct comprises at least one carrier polypeptide fused to at least one therapeutic polypeptide decoy receptor present at least partially on the outside of the delivery vesicle and wherein the at least one therapeutic polypeptide decoy receptor is signalling-incompetent, to enable binding and sequestering of its target molecule without the generation and/or transmission of any signals. In a preferred embodiment, the at least one therapeutic polypeptide decoy receptor binds to a circulating ligand but it may naturally also bind to a target molecule present on a target cell. The therapeutic polypeptide construct may comprise at least one therapeutic polypeptide decoy receptor (interchangeably termed a "decoy receptor", but said therapeutic polypeptide decoy receptors may also relate to therapeutic polypeptides not necessarily classified as decoy receptors as such) that is signalling-incompetent (or alternatively in some embodiments signalling-competent), fused to a carrier polypeptide. Naturally, one single delivery vesicle may comprise more than one polypeptide construct (i.e. a plurality of constructs are present on a single exosome), and also more than one type of polypeptide construct (a single exosome could, for example, comprise a plurality of (1) constructs comprising the VEGF receptor, as the decoy receptor, and a carrier polypeptide, such as Lamp2b, and (2) constructs comprising the EGF receptor, as the decoy receptor, and the carrier polypeptide CD63). The inventors have unexpectedly realized that using extracellular vesicles (such as exosomes) as delivery vehicles for therapeutic polypeptide decoy receptors (e.g. biopharmaceuticals) results not only in enhanced pharmacokinetics but unexpectedly also increases the efficacy of the therapeutic polypeptide decoy receptors, possibly as a result of regenerative effects exerted by exosomes and other vesicles per se. Additionally, employing extracellular vesicles as delivery vectors for therapeutic polypeptides does not only facilitate production in comparison with classical biologics, but the fact that each delivery vesicle potentially comprises a considerable plurality of therapeutic constructs (which in turn may comprise a plurality of therapeutic polypeptide decoy receptors) potentially leads to a receptor multivalency that enhances the therapeutic efficacy and improves treatment outcomes.

In preferred embodiments, the at least one therapeutic polypeptide decoy receptor may be partially or completely devoid of its signalling domain, to make it signalling-incompetent. This may be achieved either via truncating or mutating the polynucleotide encoding the signalling domain, or via completely removing said polynucleotide, in order to block any signalling from the therapeutic polypeptide decoy receptor. In a further embodiment, the signalling domain of therapeutic polypeptide decoy receptor may be partially or completely replaced by the carrier polypeptide, to possibly minimize the size of the polypeptide construct.

The inventors have realized that it is, surprisingly, in some instances preferable to utilize therapeutic polypeptide decoy receptors that are signalling-incompetent, in order to avoid generating signals that otherwise may negatively impact the therapeutic efficacy.

In one embodiment as per the present invention, the carrier polypeptide may be located partially inside the therapeutic delivery vesicle and/or partially in the therapeutic delivery vesicle membrane and/or partially outside the therapeutic delivery vesicle. In a preferable embodiment, the carrier polypeptide is present substantially on the inside of the delivery vesicle or in its membrane, whereas the therapeutic polypeptide decoy receptor is present at least partially on the outside of the delivery vesicle, to be able to exert its therapeutic effect. Thus, the polypeptide construct may preferably be present in transmembrane form (i.e. a transmembrane polypeptide construct), with the carrier polypeptide present substantially on the inside or in the vesicular membrane and the therapeutic polypeptide decoy receptor present substantially on the outside of the delivery vesicle (and either the carrier polypeptide and/or the therapeutic polypeptide decoy receptor extending through the membrane of the delivery vesicle). In one embodiment, more than one carrier polypeptide may be used, in order to improve the expression of the therapeutic polypeptide decoy receptor on the surface (outside) of the therapeutic delivery vesicle.

The location of the carrier polypeptide in the membrane may vary depending on the application and the therapeutic polypeptide in question; with the primary consideration being that the therapeutic polypeptide decoy receptor is capable of interacting with its interaction partner, normally a circulating ligand, which is normally present extracellularly for instance in the blood or in any other bodily fluid or on a circulating target cell. In further embodiments, the at least one therapeutic polypeptide decoy receptor may be fused to the carrier polypeptide via a chemical bond selected from the group comprising a peptide (amide) bond, a thio-ether bond, a di-sulfide bridge, and a biotin-streptavidin interaction. The formation of a peptide (amide) bond may naturally be achieved via recombinant technology (i.e. via expression of a suitable polynucleotide in a cell capable of producing suitable delivery vesicles) but such a bond may also be generated using various conjugation strategies commonly employed within the art, for instance EDC/NHS-mediated conjugation, sulfo-NHS conjugation, or any other type of amide (peptide) conjugation approach. However, other methodologies for coupling the at least one therapeutic polypeptide decoy receptor and the at least one carrier polypeptide may comprise forming a disulfide bridge between e.g. two cysteine residues, or utilizing the natural interaction between biotin and streptavidin to connect the therapeutic polypeptide decoy receptor and the carrier polypeptide. An alternative to using fusion constructs and chemical bond formation is to place a lipid tag on the therapeutic polypeptide decoy receptor and non-covalently coat the surface of the delivery vesicle with the therapeutic polypeptide decoy receptor by means of simple lipid intercalation. Such lipid tags may include cholestoryl, stearyl, di-stearyl, myristoyl, palmitoyl, decanoyl, and other suitable lipids know to a person skilled in the art.

The carrier polypeptide may be selected from the group comprising Lamp2b, CD63, syndecan, synaptotagmin, ALIX (CHAMP 4) domain, ALIX-syntenin binding domain, ESCRT-proteins, PDGF, syntenin-PDZ, P6- and P9-domain, CD81, CD9, and any combination thereof. Again, the primary consideration behind selecting an appropriate carrier polypeptide pertains to its ability to efficiently carry the therapeutic polypeptide decoy receptor to an appropriate vesicular location (normally its surface, or at least to a part of the therapeutic delivery vesicle membrane that enables the therapeutic polypeptide decoy receptors to interact with and bind to the ligand, i.e. its interaction partner, to exert its therapeutic effect). Further in accordance with the present invention, the carrier polypeptide may comprise the cytoplasmic part of syndecan. The cytoplasmic part of syndecan has a PDZ-binding domain which binds the syntenin-ALIX complex, and the Syntenin-ALIX complex subsequently forms an extracellular vesicle and/or an exosome (the PDZ domain would therefore essentially guide the receptor to the extracellular vesicle).

The at least one therapeutic polypeptide decoy receptor as per the present invention may be selected from the group comprising receptors, for example, from the following receptor families: insulin, PDGF (SEQ ID No 15-16), FGF (SEQ ID No 36-39), EGF, NGF (SEQ ID No 32), VEGF, HGF, TRK, EPH, AXL, LTK, TIE, ROR, DDR, RET, KLG, RYK, MuSK, Type I and Type II TGF (SEQ ID No 33-35), activin, and TNF, PTCH1 (SEQ ID No 44), interleukins (IL) 1, 6, 12, 17, 23, and others (SEQ ID No 1-11), angiopoietin, HER phage display peptides binding ligands for the receptors above (and possibly also phage display towards receptors in order to occupy binding space via allosteric hindrance), 7-TM receptors, integrins, selectins (e.g. selectins E, P, and L (SEQ ID No 19-21), ligands of integrins/selectins membrane-bound antibodies, T-cell receptors, NK-cell receptors, Toll-like receptors, PAMP, etc.

Also, engineered receptors that bind several ligands such as both VEGF and angiopoietin (DAAP) are in accordance with the present invention, and further all of the above-mentioned receptor families and specific receptors are in line with the present invention. Further in accordance with the present invention, the polypeptide construct attached to therapeutic delivery vesicles may comprise more than one therapeutic polypeptide decoy receptor, and also more than one carrier polypeptide, in order to optimize e.g. the therapeutic effects or the transport of the therapeutic polypeptide decoy receptor to delivery vesicle membrane (or its surface).

The polypeptide construct as per the present invention may consequently be formed from any combination of the at least one therapeutic polypeptide decoy receptor and the at least one carrier polypeptide. Exemplary embodiments comprise, for instance, (i) at least one therapeutic polypeptide decoy receptor from the TNF family (e.g. TNFR1) combined with a carrier polypeptide selected from CD63 (SEQ ID No 14), Lamp2b, syndecan, synaptotagmin, or any other suitable carrier polypeptide capable of transporting the at least one therapeutic polypeptide decoy receptor to the surface (or essentially any suitable location on a therapeutic delivery vesicle), (ii) at least one therapeutic polypeptide decoy receptor from the VEGF family (for instance VEGFR) combined with a carrier polypeptide selected from CD63, Lamp2b, syndecan, synaptotagmin, or any other suitable carrier polypeptide capable of transporting the at least one therapeutic polypeptide decoy receptor to the surface (or essentially any suitable location on a therapeutic delivery vesicle), (iii) at least one therapeutic polypeptide decoy receptor from the FGF family combined with a carrier polypeptide selected from CD63, Lamp2b, syndecan, synaptotagmin, or any other suitable carrier polypeptide capable of transporting the at least one therapeutic polypeptide decoy receptor to the surface (or essentially any suitable location on a therapeutic delivery vesicle), (iv) at least one therapeutic polypeptide decoy receptor from the EGF family combined with a carrier polypeptide selected from CD63, Lamp2b, syndecan, synaptotagmin, or any other suitable carrier polypeptide capable of transporting the at least one therapeutic polypeptide decoy receptor to the surface (or essentially any suitable location on a therapeutic delivery vesicle), (v) at least one therapeutic polypeptide decoy receptor from the activin family combined with a carrier polypeptide selected from CD63, Lamp2b, syndecan, synaptotagmin, (vi) at least one therapeutic polypeptide decoy receptor from the interleukin receptor family (e.g. IL6R (SEQ ID No 1) or IL12R beta 1 (SEQ ID No 4) or IL1R Type 1 (SEQ ID No 3)) combined with a carrier polypeptide selected from e.g. CD63, Lamp2b, syndecan, synaptotagmin, or any other suitable carrier polypeptide capable of transporting the at least one therapeutic polypeptide decoy receptor to the surface (or essentially any suitable location on a therapeutic delivery vesicle), or any other suitable carrier polypeptide capable of transporting the at least one therapeutic polypeptide decoy receptor to the surface (or essentially any suitable location on a therapeutic delivery vesicle).

In yet another advantageous embodiment of the present invention, a suitable carrier polypeptide (such as CD63, Lamp2b, CD9, CD81, synaptotagmin, or syndecan, etc.) is fused to PTCH1, creating a polypeptide construct capable of sequestering sonic hedgehog (SHH), which is an important signalling molecule implicated in various cancers. The inventors have experimentally seen decreased tumour burden in mice treated with exosomes comprising various carrier polypeptides coupled to PTCH1 and to a specifically selected SHH-binding domain of PTCH1. For instance, in the experimental setup reported in FIG. 4, exosomes comprising polypeptide constructs comprising CD63 or Lamp2b as the carrier polypeptide and PTCH1 as the therapeutic polypeptide decoy receptor showed similar anti-tumour efficacy as the syndecan-VEGFR constructs shown in the graph in question.

In additional embodiments, the therapeutic delivery vesicle in accordance with the present invention may further comprise at least one targeting entity present. Said targeting entity is normally at least partially present on the outside of the delivery vesicle, in order to enable targeting of the vesicles to tissues, cell types, or organs of interest, e.g. to increase the concentration of delivery vesicles locally at the site where the therapeutic efficacy needs to be as high as possible. The targeting entity may be a peptide or a polypeptide (e.g. an antibody or an antibody fragment), but it may also be a small molecule (such as a vitamin), a carbohydrate, a nucleic acid (such as an aptamer), or any other type of molecule that may confer targeting properties to therapeutic delivery vesicles.

Further in accordance with the present invention, the therapeutic delivery vesicle may be selected from the group comprising exosomes, microvesicles, apoptotic bodies, microparticles, ectosomes, prostatosome cardiosomes, liposomes, lipid-like materials or structures, lipidoids, VLDL particles, LDL particles, HDL particles, chylomicrons, etc.

Generally, the present invention pertains to delivery vesicles as per the instant invention for use in medicine, and more specifically the present invention relates to the use in the prophylaxis and/or alleviation and/or treatment of diseases and disorders selected from the group comprising Crohn's disease, ulcerative colitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, kidney failure, graft-vs-host disease, Duschenne muscular dystrophy and other muscle diseases, neurodegenerative disease including Alzheimer's disease, Parkinson's disease, Huntingtons disease, ALS, cancer-induced cachexia, anorexia, diabetes mellitus type 2, and cancers (for instance cancers sensitive to EGF, VEGF, FGF). Some of the cancer types of relevance for the present invention comprises, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas ((AIDS-related lymphoma, Burkitt lymphoma, cutaneous T-Cell lymphoma, Hodgkin lymphoma, Non-Hodgkin (an old classification of all lymphomas except Hodgkin's) lymphoma, Primary Central Nervous System lymphoma)), Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sezary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, Waldenström macroglobulinemia, and/or Wilm's tumor (kidney cancer).

Furthermore, the present invention pertains to pharmaceutical compositions comprising therapeutic delivery vesicles as per the present invention, normally formulated with at least one pharmaceutically acceptable excipient. The at least one pharmaceutically acceptable excipient may be selected from the group comprising any pharmaceutically acceptable material, composition or vehicle, for instance a solid or liquid filler, a diluent, an excipient, a carrier, a solvent or an encapsulating material, which may be involved in e.g. suspending, maintaining the activity of or carrying or transporting the therapeutic delivery vesicles from one organ, or portion of the body, to another organ, or portion of the body (e.g. from the blood to any tissue and/or organ and/or body part of interest).

The present invention also relates to cosmetic applications of the delivery vesicles, either with or without the polypeptide construct(s). Thus, embodiments of the present invention may pertain to skin care products such as creams, lotions, gels, emulsions, ointments, pastes, powders, liniments, sunscreens, shampoos, etc., comprising the delivery vesicles, in order to improve and/or alleviate symptoms and problems such as dry skin, wrinkles, folds, ridges, and/or skin creases. The delivery vesicles may exhibit beneficial effects without the polypeptide construct being present but the presence of a suitable polypeptide construct may further enhance the cosmetic efficacy. In one embodiment, the delivery vesicles as per the present invention may comprise a botulinum toxin (e.g. botox, for instance botulinum toxin types A-G) as the therapeutic polypeptide decoy receptor (botulinum toxins may not necessarily be used only for cosmetic applications but could also be applied for e.g. treatment of migraine headaches and dystonia). In a preferred embodiment, exosomes from a suitable exosome-producing cell are comprised in a cosmetic cream, lotion, or gel for use in the treatment (which is normally for cosmetic purposes) of wrinkles, lines, folds, ridges and/or skin creases.

In a further embodiment, the exosomes in accordance with the present invention may comprise a therapeutic polypeptide construct but may also be devoid of any artificially introduced therapeutic polypeptide construct or may contain polypeptide constructs having merely e.g. cosmetic capacity. Both extracellular vesicles devoid of therapeutic polypeptide constructs and extracellular vesicles comprising therapeutic polypeptide construct may mediate anti-inflammatory, anti-apoptotic and cell proliferative effects that may enhance wound healing and skin regeneration. Experiments carried out using (i) exosomes without any therapeutic polypeptide construct and (ii) exosomes comprising a VEGFR1 therapeutic polypeptide construct (with either CD63 or Lamp2b as the carrier polypeptide) show that both strategies display strong cosmetic potency in alleviating e.g. telangiectasias (small dilated blood vessels located near the skin). Exosomes devoid of therapeutic polypeptides were also shown to alleviate cosmetic problems such as dry skin, wrinkles, rashes, etc., and additionally exosomes comprising e.g. TNFR-containing therapeutic polypeptides are highly potent in treating rashes, scaling, and potentially psoriasis and psoriasis-related problems.

In further embodiments, the delivery vesicles in accordance with the present invention may comprise therapeutic polypeptide decoy receptors such as collagen, laminins (for instance laminins 111, 211, 511, and/or 521), and/or cell-penetrating peptides (CPPs).

Optionally, glycosaminoglycans (GAGs) and/or other types of carbohydrates may be included in the delivery vesicles, to further augment effects related to maintaining the structural integrity of the skin.

In one aspect as per the present invention, the polypeptide construct may comprise a polypeptide construct which comprises virtually any therapeutic polypeptide decoy receptor that can bind to a circulating ligand fused to virtually any carrier polypeptide.

The pharmaceutical compositions as per the present invention are naturally suitable for use in medicine, and specifically in the prophylaxis and/or alleviation and/or treatment of diseases and disorders selected from the group comprising Crohn's disease, ulcerative colitis, rheumatoid arthritis, multiple sclerosis, systemic lupus erythematosus, sarcoidosis, idiopathic pulmonary fibrosis, psoriasis, tumour necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, kidney failure, graft-vs-host disease, Duschenne muscular dystrophy and other muscle diseases, cancer-induced cachexia, anorexia, diabetes mellitus type 2, and cancer (for instance cancers sensitive to EGF, VEGF, FGF).

The therapeutic delivery vesicles as per the present invention may be administered to a human or animal subject via various different routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intrailial, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes.

In a further aspect, the present invention relates to a method of producing a therapeutic delivery vesicle, comprising the steps of (i) providing at least one polynucleotide construct encoding at least one polypeptide construct, wherein the polypeptide construct comprises at least one carrier polypeptide fused to at least one therapeutic polypeptide decoy receptor that binds a circulating ligand, (ii) introducing said at least one polynucleotide construct into a cell capable of producing suitable delivery vesicles (through translating the polynucleotide construct into the corresponding polypeptide construct), and, (iii) collecting at least one delivery vesicle produced by the cell of step (ii). The method may further comprise a purification step, wherein the therapeutic delivery vesicle is purified through a procedure selected from the group comprising liquid chromatography (LC), high-performance liquid chromatography (HPLC), spin filtration, tangential flow filtration, centrifugation, immunoprecipitation, etc, or any combination thereof.

The inventors have surprisingly realized that applying a sequential combination of filtration (preferably ultrafiltration (UF)) and size exclusion liquid chromatography (LC) results in optimized purification, which in turn leads to superior therapeutic efficacy. Further, as compared to ultracentrifugation (UC), which is routinely employed for purifying exosomes, sequential ultrafiltration-liquid chromatography (UF-LC) is considerable faster and possible to scale to higher manufacturing volumes, which is a significant drawback of current UC methodology. However, as will be described in greater details below, the most advantageous implication of the use of UF-LC instead of UC is the fact that exosomes (and other extracellular vesicles to which UF-LC is applied) retain their biophysical and biological properties, which results in less accumulation in lung tissue upon in vivo administration and therefore improves the therapeutic efficacy.

According to electron microscopy (EM) analysis, vesicles from both UF and UC preparations displayed a rounded or cup-shaped morphology. In most cases the vesicle diameter was measured to be around 100 nm, and this was in accordance with results obtained via nanoparticle tracking analysis (NTA). Of note however, a fraction of vesicles in the UC sample was clearly distorted (either disrupted or fused to form slightly larger vesicles) and such vesicles were not observed in UF samples. Hence, these results indicate that the UC methodology had a negative impact on vesicular integrity.

To verify the presence of vesicle aggregates in UC samples, the inventors next examined HEK293T CD63-EGFP labeled exosomes directly by fluorescence microscopy. Similar to the FCS results, only UC samples displayed visible large aggregates in the fluorescence channel, which were not seen with UF samples. This was corroborated using the fluorescent dye DiOC6 labeled exosomes. Thus the UF isolation method results in preservation of the inherent biophysical properties of vesicles compared to UC, which results in fusion/aggregation and disruption of vesicles.

The UF experiments in accordance with the present invention were performed primarily using filters with a molecular weight cut-off of 100-kDa, 250-kDa, and/or 500-kDa, or any sequential combination thereof. In preferred embodiments, 100-kDa cut-off is preferable but given the number of biomolecules with higher molecular weight, it is possible that media/cell-secreted components other than exosomes are entrapped in the filters and the UF protocol was therefore refined further using highly unconventional size exclusion liquid chromatography. UF samples were loaded on inter alia a Sephacryl S-300 or a Sephacryl S-500 size exclusion LC column where two distinct fractions were collected based on the UV flow cell absorbance at 280 nm. NTA revealed that 98% of the particles were recovered in fraction 1 where the mode particle size was consistent in all three UF-LC replicates. Subsequent total protein staining on SDS-PAGE confirmed that many of the contaminating proteins originally seen in the UF sample were eluted in fraction 2 while fraction 1 did not have any detectable levels of protein. By using Western Blot (WB), exosomal markers such as Alix and CD9 were only detected in fraction 1 and not in fraction 2, indicating that fraction 1 contained pure exosomes. Moreover, the vesicle recovery rate following LC fractionation was 70+/−19%, hence LC did not hamper the gain in particle yield achieved by UF alone. WB corroborated this data, as the exosomal markers were more strongly expressed in LC fraction 1 compared to UC-purified samples. Furthermore, the protein per vesicle ratio was much lower for UF-LC compared to UC samples. EM was also performed on fraction 1 and 2, where intact cup-shaped vesicles were detected only in fraction 1, while protein aggregates were seen in fraction 2. Furthermore, when HEK293T CD63-EGFP labeled exosomes purified with UF-LC were visualized by fluorescent microscopy, EGFP positive vesicles appeared similar to the UF purified vesicles indicating that LC did not affect the biophysical properties of the vesicles. Thus, the inventors have discovered that using a two-step method combining UF with subsequent LC surprisingly allows for highly efficient isolation of high yields of biophysically intact exosomes free of protein contamination. The exosomes field currently relies completely on the perceived effectiveness of the UC method, which the present inventors have proved to be highly unreliable.

The UF-LC purification method of the present invention and the conventional UC method isolated vesicles with similar protein contents, as evidenced by the good proteomic overlap between the two methods. However, importantly, the UF-LC method results in high yield purification of vesicles devoid of non-exosomal contamination.

Despite similar proteomic profiles of exosomes isolated by the UF-LC method of the present invention and conventional UC methods, the inventors hypothesized that the distinct differences in exosome integrity between the purification methods (vesicle aggregation and fusion following UC purification) might influence their biological properties in vivo. Given that it is well-established that aggregated particles typically show lung accumulation following intravenous (IV) injection the inventors speculated that UC purified exosomes might preferentially distribute to lung tissues compared to UF-LC purified vesicles. To investigate this, the same number of near-infrared fluorescent dye (DiR) labeled exosomes (based on NTA calculations) were injected via the tail vein in adult Balb/c mice and the biodistribution was analysed using IVIS imaging 24 h post injection. As postulated, UC purified exosomes showed a 4.6 times ($p<0.0001$) stronger signal in the lungs compared to UF-LC purified vesicles. The signal from the liver was as expected higher in the UF-LC group ($p<0.0001$), since the total fluorescence injected only differed by 6%. Thus vesicles isolated using the highly advantageous UF-LC methods of the present invention are biophysically intact, do not preferentially accumulate in lung and therefore are better suited for in vivo therapeutic applications.

As can be realized from the above description, the UF-LC method is generally applicable to purification of any type of vesicles (such as exosomes, liposomes, etc.) and may be in a broad aspect comprise exposing any type of suitable vesicle preparation which needs to be purified to UF-LC as described herein. In one exemplary embodiment, the present invention thus pertains to obtaining extracellular vesicles from a suitable source (for instance vesicle produced by the methods of the present invention, which may optionally comprise polypeptide constructs which in turn comprise carrier polypeptides and therapeutic decoy receptors), exposing the vesicles (which are normally present in a medium also comprising various other components such as proteins and peptides) to an ultrafiltration step followed by a size exclusion liquid chromatography (LC) step.

Further, in a preferred embodiment the present invention relates to a method of producing a therapeutic delivery vesicle, comprising the steps of (i) providing at least one polynucleotide construct encoding at least one polypeptide construct, wherein the polypeptide construct comprises at least one carrier polypeptide fused to at least one therapeutic polypeptide decoy receptor that binds a circulating ligand, (ii) introducing said at least one polynucleotide construct into a cell capable of producing suitable delivery vesicles (through translating the polynucleotide construct into the corresponding polypeptide construct), and, (iii) purifying the delivery vesicles of step (ii) using ultrafiltration (UF) followed by size exclusion liquid chromatography (LC). The delivery vesicles obtained using said methodology may therefore display significantly enhanced biophysical stability and biological properties than vesicles obtained via conventional UC methodology. In a further embodiment, at least one filter may be used for the UF step, and the filter(s) may have the same or different cut-offs, e.g. one could initially perform a first step with a cut-off of 100 kDa and in a second step a filter with a cut-off of 200 kDa. Naturally, the filter may be selected to have any appropriate cut-off, for instance 100 kDa, 200 kDa, 500 kDa, etc. Furthermore, in additional embodiments, the column used for the LC step may have essentially any suitable pore size. S-300, S-500 and S-1000 of a Sephacryl column worked equally well, consistently producing two well-defined peaks with one of said peaks being the vesicle-containing fraction.

Figure 8:
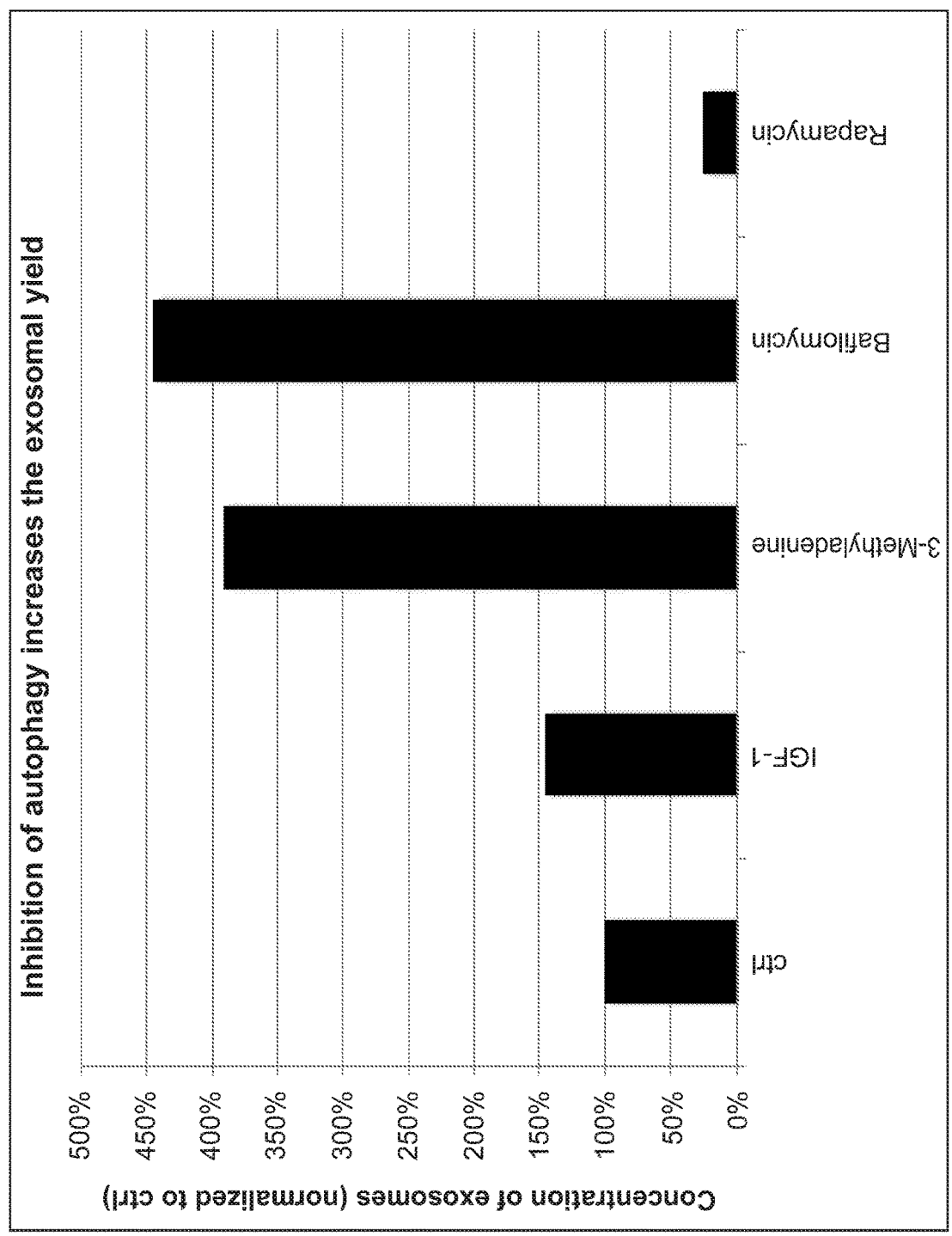
FIG. 8 shows inhibition of autophagy resulting in increased exosomal yields. The graph displays, from left to right, cells treated with culture media only (as a baseline control), growth factor-supplemented media (for instance supplemented with IGF-1), media comprising autophagy inhibitors (3-methyladenine and bafilomycin) or media comprising autophagy activators (rapamycin). Treatment with autophagy inhibitors results in a strong increase in the exosomal yield, which can be exploited in the production of exosomes as per the present invention.

In a further embodiment of the present invention, the production of extracellular vesicles (such as exosomes) may be increased by including autophagy inhibitors in the cell culture medium when growing the vesicle-producing cells. As portrayed in FIG. 8, treating cells with autophagy inhibitors resulted in a surprising increase of the exosomal yield. Various substances can be used to inhibit the different stages of the autophagy pathway, for instance including but not limited to Bafilomycin A and chloroquine (inhibiting the fusion of the autophagosome with the lysosome), and/or 3-methyladenine (which is a PI3K inhibitor that hinders the formation of pre-stages of the autophagosome). Thus, the present invention further relates to the use of autophagy inhibitors to increase the vesicle yield in cell culture. Autophagy-inhibiting substances as per the present invention may include beclin-1 inhibitors, PI3K inhibitors (e.g. 3-methyladenine), and inhibitors of the fusion between autophagosome and lysosome (e.g. Bafilomycin A and chloroquine). Thus, in one general aspect, the present invention relates to increasing the yield of extracellular vesicles by treating the vesicle-producing cell(s) with at least one inhibitor of autophagy.

In a preferred embodiment, the method of producing a therapeutic delivery vesicle as the present invention may hence comprise the steps of (i) providing at least one polynucleotide construct encoding at least one polypeptide construct, (ii) introducing said at least one polynucleotide construct into a cell capable of producing vesicles comprising the polypeptide construct translated from the polynucleotide construct, (iii) cultivating said cells in the presence of at least one autophagy inhibitor, (iv) purifying the delivery vesicles obtained from said cells using UF-LC purification.

The method of producing a therapeutic delivery vesicle may alternatively comprise the steps of (i) providing (a) at least one polynucleotide construct encoding at least one therapeutic polypeptide decoy receptor, and (b) at least one polynucleotide construct encoding at least one carrier polypeptide, (ii) introducing at least one of the polynucleotide construct (a) and at least one of the polynucleotide construct (b) into a cell capable of producing delivery vesicles, and (iii) collecting at least one delivery vesicle produced by the cell of step (ii). When employing this method, the at least one therapeutic polypeptide decoy receptor and the at least one carrier polypeptide may form a single polypeptide construct through formation of e.g. a disulfide bridge between the carrier polypeptide and the therapeutic polypeptide decoy receptor, or through the formation of a biotin-streptavidin interaction, or through the formation of any other type of chemical bond, including the formation of a syndecan-syntenin-ALIX complex In yet another aspect, the present invention pertains to a polypeptide construct comprising at least one therapeutic polypeptide decoy receptor that binds a target molecule, fused to at least one carrier polypeptide. Said polypeptide construct may in exemplary embodiments comprise, for instance, (i) at least one therapeutic polypeptide decoy receptor from the TNF family combined with a carrier polypeptide selected from CD63, Lamp2b, syndecan, synaptotagmin (or any derivatives or analogues thereof), or any other suitable carrier polypeptide capable of transporting the at least one therapeutic polypeptide decoy receptor to the surface (or essentially any suitable location on a therapeutic delivery vesicle), (ii) at least one therapeutic polypeptide decoy receptor from the VEGF family combined with a carrier polypeptide selected from CD63, Lamp2b, syndecan, synaptotagmin (or any derivatives or analogues thereof), or any other suitable carrier polypeptide capable of transporting the at least one therapeutic polypeptide decoy receptor to the surface (or essentially any suitable location on a therapeutic delivery vesicle), (iii) at least one therapeutic polypeptide decoy receptor from the FGF family combined with a carrier polypeptide selected from CD63, Lamp2b, syndecan, synaptotagmin (or any derivatives or analogues thereof), or any other suitable carrier polypeptide capable of transporting the at least one therapeutic polypeptide decoy receptor to the surface (or essentially any suitable location on a therapeutic delivery vesicle), (iv) at least one therapeutic polypeptide decoy receptor from the EGF family combined with a carrier polypeptide selected from CD63, Lamp2b, syndecan, synaptotagmin (or any derivatives or analogues thereof), or any other suitable carrier polypeptide capable of transporting the at least one therapeutic polypeptide decoy receptor to the surface (or essentially any suitable location on a therapeutic delivery vesicle), (v) at least one therapeutic polypeptide decoy receptor from the activin family combined with a carrier polypeptide selected from CD63, Lamp2b, syndecan, synaptotagmin (or any derivatives or analogues thereof), or any other suitable carrier polypeptide capable of transporting the at least one therapeutic polypeptide decoy receptor to the surface (or essentially any suitable location on a therapeutic delivery vesicle).

Moreover, the present invention may in further aspects relate to a polynucleotide construct encoding at least one therapeutic polypeptide in accordance with the present invention, and, in an additional aspect, a cell comprising at least one polynucleotide construct and/or at least one polypeptide construct. In a further aspect, the present invention pertains to a therapeutic delivery vesicle obtainable by the methods as per the present invention. The cells that may be utilized for the purposes of the present invention comprise for instance mesenchymal cells, adult stem cells (eg. myoblasts), induced pluripotent stem (iPS) cells, cord blood stem cells, embryonic stem cells, and/or amniotic stem cells, blood-derived cells (eg. B-cells, macrophages, DC-cells, T-cells, NK-cells, platelets etc), immortalized eukaryotic cells or cell-lines (eg. neuroblastoma cells NSC34, N2a and SHSY5Y, HEK cells, C17.2 neuronal stem cells, bEND3 neuroendothelial cells, HeLa cells, U2OS cells etc), or any combination of these sources of cells.

Figure 10:
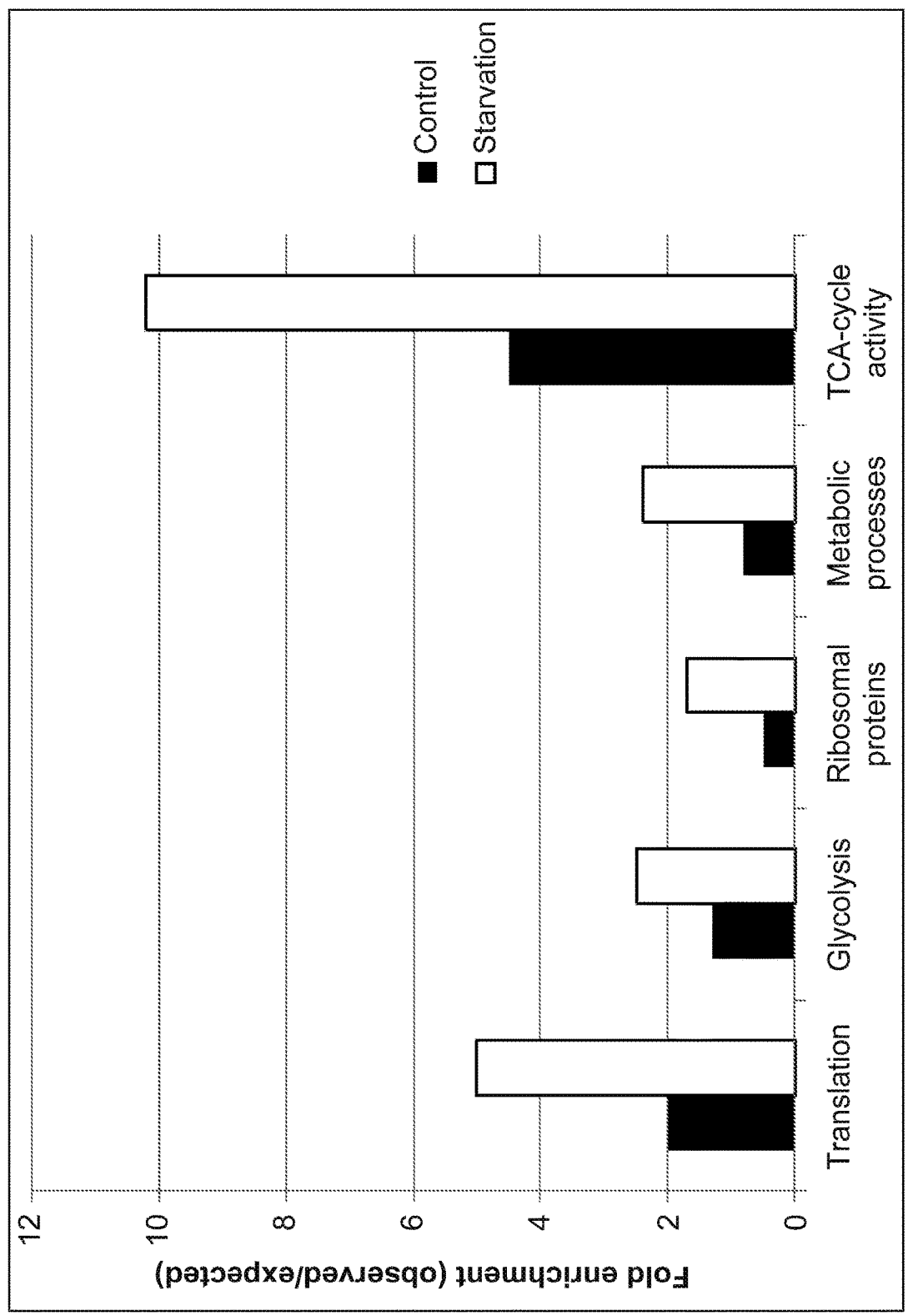
FIG. 10 illustrates the effects of stress-inducing conditions on enrichment of anti-apoptotic and metabolically active proteins, according to GO-terms (GO-terms: translation, metabolic processes, glycolysis and ribosomal proteins). As compared to cells cultured under normal conditions, exosomes obtainable from cells cultured under stress-inducing conditions (e.g. serum-starvation and/or oxygen deprivation) are enriched in proteins for survival and metabolic processes, which is beneficial for regenerative medicine applications.

The inventors have unexpectedly realized that the proteome of extracellular vesicles obtainable from cells exposed to stress-inducing culturing conditions (such as serum-starvation and oxygen deprivation) is enhanced in positive GO terms as compared to the proteome of extracellular vesicles from cells grown under normal control conditions. Extracellular vesicles (such as exosomes) from cells exposed to serum-starvation and/or oxygen deprivation (i.e. reduced oxygen supply) were analysed with state of the art LC/MS/MS (proteomics) to examine the changes in proteome the different culturing conditions bring about. Surprisingly, stress-inducing conditions enriched anti-apoptotic and metabolically active proteins to a greater extent than normal culturing conditions according to GO-terms (FIG. 10) (GO-terms: translation, metabolic processes, glycolysis and ribosomal proteins). Hence, serum-starvation and/or oxygen deprivation enrich proteins for survival and metabolic processes in the exosomes, which would be a benefit for regenerative purposes. The GO-terms were normalized to the proteome of exosomes from a reference control cell and the enrichment is expressed as fold increase over the expected value from the reference cell. Thus, in a further generally applicable aspect, the present invention relates to the use of stress-inducing conditions to enrich the proteome of an extracellular vesicle (e.g. an exosomes) for metabolically active proteins and/or anti-apoptotic proteins, i.e. positive GO terms such as translation, metabolic processes, glycolysis and/or ribosomal proteins. In a further embodiment, the method for obtaining extracellular delivery vesicles as according to the present invention may comprise a step where the cells from which the extracellular vesicles are obtained are exposed to stress-inducing conditions (for instance but not limited to oxygen deprivation and/or serum-starvation), in order to induce enrichment of metabolically active proteins and/or anti-apoptotic proteins to enhance the regenerative effects of the extracellular vesicles. When comparing control vesicles (without any therapeutic polypeptide) cultured under stress-inducing conditions with control vesicles (without any therapeutic polypeptide) cultured under normal conditions the stress-exposed extracellular vesicles generate a clearly enhanced therapeutic effect in various inflammatory models, indicating that the regenerative capabilities of the extracellular vesicles (notably exosomes) have increased due to the stress-inducing culturing conditions.

A particularly advantageous aspect of the present invention pertains to exposing cells from which extracellular vesicles are to be obtained to a combination of both autophagy inhibitors and stress-inducing conditions, in order to (1) increase the yield of vesicles and (2) increase the regenerative capacity of the exosomes thus produced. Vesicles (such as exosomes) obtained via this combinatorial approach may be purified using the advantageous UF-LC protocol of the present invention, to truly ensure that the therapeutic efficacy of the extracellular vesicles is optimized.

Further, the present invention relates to a method of treatment comprising administering a therapeutically effective amount of therapeutic delivery vesicles to a subject in need thereof, wherein the method is aimed at improving, alleviating, and/or preventing diseases such as Crohn's disease, ulcerative colitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, kidney failure, graft-vs-host disease, Duschenne muscular dystrophy and other muscle diseases, neurodegenerative disease including Alzheimer's disease, Parkinson's disease, Huntingtons disease, cancer-induced cachexia, anorexia, diabetes mellitus type 2, and cancers (for instance cancers sensitive to EGF, VEGF, FGF). Some of the cancer types of relevance for the present invention comprises, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas ((AIDS-related lymphoma, Burkitt lymphoma, cutaneous T-Cell lymphoma, Hodgkin lymphoma, Non-Hodgkin (an old classification of all lymphomas except Hodgkin's) lymphoma, Primary Central Nervous System lymphoma)), Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sezary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, Waldenström macroglobulinemia, and/or Wilm's tumor (kidney cancer).

Unlike many other therapies, exosomes and other extracellular vesicles have the potential to cross the blood-brain barrier (BBB). Therapeutic delivery exosomes comprising signalling-incompetent decoy receptors for e.g. IL6, IL-1β and TNFα may thus modulate the various disorders of the central nervous system (CNS), and specifically various forms of neuro-inflammation. Neuro-inflammation is inflammation of the nervous system, including the central nervous system (CNS). The neuroinflammation may be acute, e.g. infection or traumatic events, or chronic, e.g. neurodegenerative diseases (including Alzheimer's disease, Parkinsons disease and demyelinating diseases, such as multiple sclerosis (MS)). In the CNS, glial cells, including microglia and astrocytes, have an important role in innate immunity. These cells, among others cell types in the brain, can produce cytokines and chemokines that act as neuromodulators. The most common cytokines in CNS neuro-inflammation include IL6, IL-1β and TNFα. Production of theses pro-inflammatory cytokines can cause neurotoxicity and may compromise the integrity of the blood-brain-barrier (BBB).

Figure 9:
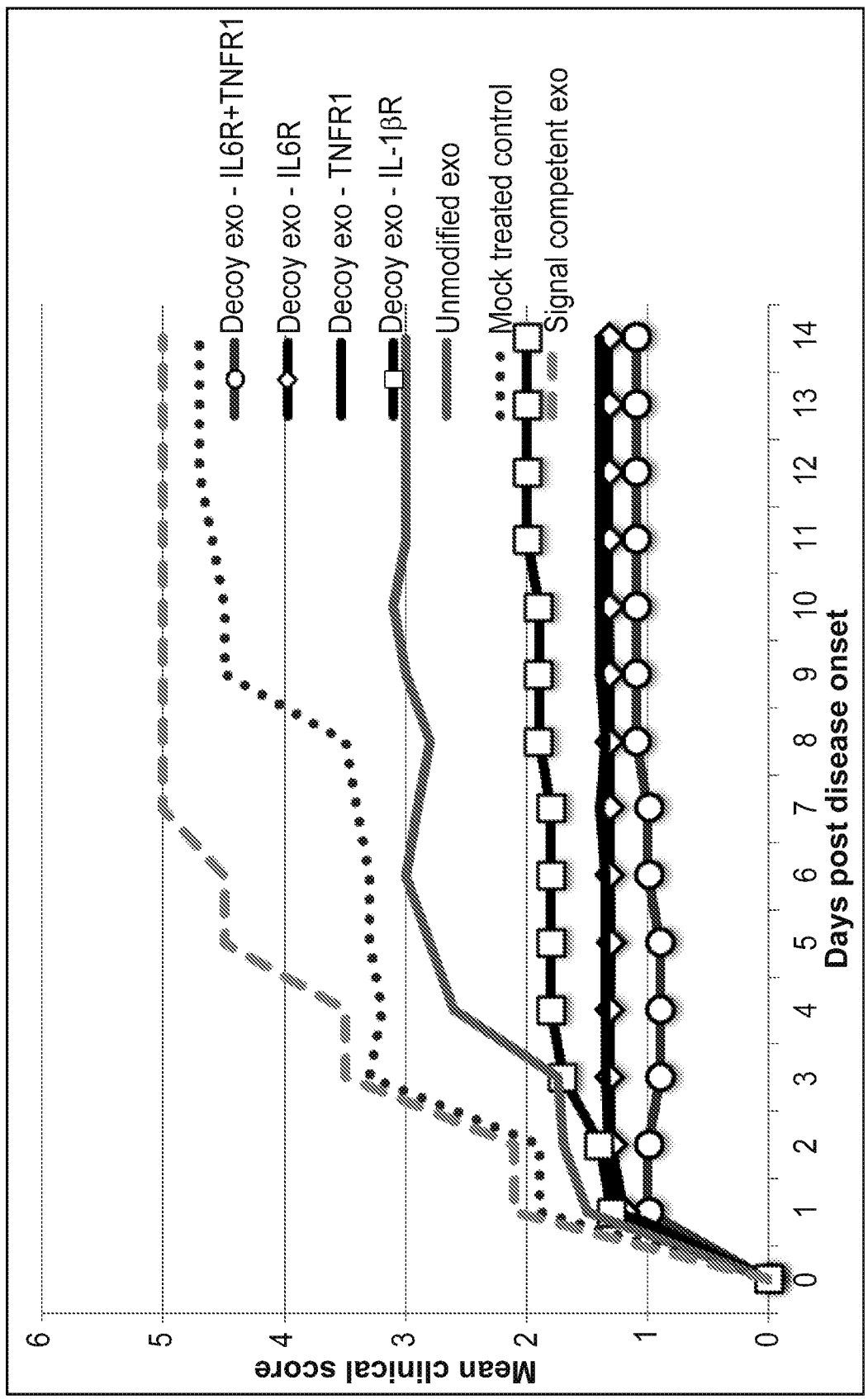
FIG. 9 shows how EAE-mice treated with exosomes comprising displaying signalling-incompetent therapeutic decoy receptors for IL6 (SEQ ID No 1-2), IL-1β (SEQ ID No 3-5) and TNFα (solid black line and solid black lines with circles, squares, and diamonds) display a very moderate disease manifestation compared to mock treated control (dotted line), whereas signalling-competent (TNFR1 signalling-competent) exosomes treated mice in fact display a worsened disease (dashed grey line).

In an in vivo model of experimental autoimmune encephalomyelitis (EAE), mice treated with therapeutic delivery exosomes comprising various therapeutic polypeptide decoy receptor(s) (as described above) displayed a markedly improved disease phenotype, as illustrated by FIG. 9. Thus, in a further aspect, the present invention pertains to delivery of any suitable receptor (for instance IL-6R, TNFR1, IL-1βR, and/or any combination thereof) to the CNS, to treat essentially any neuro-inflammation.

Furthermore, the instant invention additionally relates to reagents, kits, cell mediums, and cell culturing processes. For instance, cell culturing processes utilizing the methods for producing the therapeutic delivery vesicles of the present invention may be employed in a variety of suitable exosome-producing cell lines, such as mesenchymal cells, adult stem cells (e.g. myoblasts), induced pluripotent stem (iPS) cells, cord blood stem cells, embryonic stem cells, and/or amniotic stem cells, blood-derived cells (eg. B-cells, macrophages, DC cells, T-cells, NK-cells, platelets etc), immortalized eukaryotic cells or cell-lines (eg. neuroblastoma cells NSC34, N2a and SHSY5Y, HEK cells, C17.2 neuronal stem cells, bEND3 neuroendothelial cells, HeLa cells, U2OS cells etc), or any combination of these sources of cells. In further embodiments, the present invention pertains to cell culture medium, any suitable reagent for in vitro use, and/or a kit of parts comprising the therapeutic delivery vesicles. Particularly advantageous kits may comprise, optionally in separate contains, cell media for culturing vesicle-producing cells and autophagy inhibitors, to increase the vesicle (preferably exosome) production yield. The cell culture media as per the present invention may be tailored to contain very little or no serum in order to ensure that the vesicles produced by the cells are expressing higher amounts of metabolically active and anti-apoptotic proteins, to increase their inherent regenerative capacity. For instance, in one preferred embodiment the present invention pertains to a kit comprising (i) culturing media for cell culture under serum-starvation conditions to enhance the regenerative effects of the extracellular vesicles (exosomes) produced, (ii) autophagy inhibitors such as chloroquine, bafilomycin A, and/or 3-methyladenine, or any combination thereof to increase the production yield of the extracellular vesicles (exosomes), and suitable cells for production of extracellular vesicles, for instance exosomes.

It shall be understood that the above described exemplifying aspects, embodiments, and alternatives, and variants can be modified without departing from the scope of the invention, inter alia with respect to the described constituents and components (e.g. the therapeutic delivery vesicles, the therapeutic polypeptide decoy receptors, and the carrier polypeptides, etc.), materials (e.g. therapeutic delivery vesicles, cell types, etc.), and method parameters (e.g. purification techniques, conjugation approaches, etc.) applied. The invention will now be further exemplified with the enclosed examples, which naturally also can be modified without departing from the scope of the invention.

Examples

Cell-Based Delivery Vesicle Production

A cell type producing a suitable therapeutic delivery vesicle, such as an exosome, a microvesicle, or any other type of cell-derived structure, is plated/seeded with an appropriate density in cell media. In the case of exosome production, an exosome-producing cell type is plated/seeded with an appropriate density in cell media. The cell media is removed after 24 hours and the plate is washed with PBS 3 times. New fresh exosome-depleted media or serum free media is added. Exosomes are purified from the conditioned media. The time of incubation before the media is taken from the cells usually ranges from 48-72 hours depending on cell type, it may however be increased or decreased under certain circumstances.

The media that the cells are grown in is always depleted of foreign exosomes and microparticles by ultracentrifugation at 110 000 g overnight before incubation with the cells. Alternatively, a serum free media is applied in its place, such as OptiMEM or DMEM.

The conditioned media can be purified with different techniques; ultrafiltration with sequential LC or high performance liquid chromatography purification, ultracentrifugation, or commercially available kits. Before ultra-filtration or ultracentrifugation, the conditioned media is cleared of cells and cell debris by spinning the media at 300 g for 5 minutes. The supernatant is subsequently spun again at 1500 g for 15 minutes and ran through a 0.2-micrometer filter. The conditioned media is thus cleared of vesicles and aggregates over 200 nanometer in size. The 0.2-micrometer filtration can be exchanged to a 15 000 g spin for 30 minutes.

By ultra-filtration or tangential flow the conditioned media is concentrated. The MWCO limit is in both methods used are 100 kDa. The concentrated media is further purified by LC or HPLC, using a suitable column, such as Sephacryl S-300. The first fraction from the LC/HPLC contains the exosomes.

By ultracentrifugation the conditioned media is spun at 110 000 g for 70 minutes, the supernatant is discarded and the pellet is re-suspended in PBS and once again centrifuged at 110 000 g for 70 minutes. The supernatant is discarded and the pellet re-suspended in PBS. To further purify the exosomes the second step of the purification process can be done with a 30% sucrose cushion. The cushion traps the exosomes. The exosomes are eluted from the sucrose cushion by another centrifugation step in PBS at 110 000 g for 70 minutes and then the pellet is re-suspended in PBS.

The exosome sample can be analyzed with western blot, ELISA, NTA and electron microscopy. The amount of decoy receptors in each sample may be determined by ELISA towards a polypeptide of interest. The dose given is then calculated as amount of polypeptide given from the concentration obtained from the ELISA.

Artificial Vesicle Production

Liposomes, lipid-like structures, lipidoids, and other types of artificially produced lipid-based delivery vesicles may also be utilized for the purposes of the present invention. These vesicles may be produced by techniques known in the art and the polypeptide construct comprising the carrier polypeptide and the therapeutic polypeptide decoy receptor may be loaded onto the vesicles using standard technology, for instance lipid-tagging, etc.

Validation of UF-LC Purification Protocol

Cell Culture

NSC-34, a fusion of motor neuron enriched embryonic mouse spinal cord cells with mouse neuroblastoma, N2a, a mouse neuroblastoma cell line, B16F10, a mouse melanoma cell line and human embryonic kidney (HEK293T) cells were cultured at 37° C. with 5% $CO_2$ in complete media comprised of Dulbecco's Modified Eagle Medium (DMEM, Invitrogen), supplemented with 10% fetal bovine serum (FBS, Cellgro), and penicillin/streptomycin (pen/strep, 5000 µg/ml, Cellgro). For exosome isolation, media were changed 24 h after seeding to either pre-spun media or OptiMEM. Pre-spun media is DMEM supplemented with 10% FBS that had been pre-spun at 120,000 g for 70 min prior to making up the vesicle devoid media. Both OptiMEM and pre-spun media were supplemented with pen/strep. Conditioned media was then collected for exosome isolation 48 h after incubation. For large-scale experiments, conditioned media collected from multiple flasks were pooled prior to isolation of exosomes.

Transfection of HEK293T Cells 6 million cells were seeded one day prior to transfection in a 15 cm culture dish with DMEM complete media. Transfection of the CD63-EGFP plasmid was done using polyethyleneimine (PEI) at a 1:4 pDNA:PEI ratio. Briefly, 25 µg of plasmid and 100 µg of PEI were diluted in 500 µl of OptiMEM in separate tubes. After 5 min of incubation at room temperature (RT), the pDNA and PEI solutions were combined and incubated for a further 30 min at RT to form the DNA/PEI complexes. The complexes were then added dropwise to cells. After 4 h, the cell growth media containing the complexes was removed; the cells were washed with phosphate buffer saline (PBS) and fresh OptiMEM, supplemented with P/S antibiotics was added on the cells. After 48 h of incubation, the conditioned media was collected for exosome isolation.

Ultracentrifugation (UC) for Isolation of Exosomes

Isolation of exosomes by UC was performed as described in Supplementary Fig. S1a. Briefly, protocol 1 involves two low speed spins, 300 g for 5 min followed by 1200 g for 10 min to get rid of cell debris and larger particles. The supernatant was subsequently filtered through a 0.22 µm syringe filter before the final ultracentrifugation step at 120,000 g for 70 min. Protocol 2 follows that of protocol 1 but includes an additional PBS wash at 120,000 g for 70 min. Briefly, conditioned media was subjected to an initial low speed spin at 300 g for 5 min, followed by a 10,000 g spin for 30 min. The supernatant was then ultracentrifuged at 120,000 g for 70 min. Protocol 4 is similar to protocol 1 but lacks the 0.22 µm syringe filtration step.

Ultrafiltration (UF) for Isolation of Exosomes

The UF protocol involves the same initial low-speed spins as that of the UC protocol. Instead of a high-speed ultracentrifugation at the final step, the cell culture supernatants were spun in 100-kDa cut-off Amicon Ultra-15 spin filter (Millipore) while placental perfusates were spun in 300-kDa cut-off filter (Vivaspin, Sartorius Stedim) at 3500 g for 15 min. PBS was then added to the filters and spun down to wash the samples.

Liquid Chromatography Fractionation of UF Samples (UF-LC) from Cell Culture

UF samples, prepared as described above, were loaded onto a HiPrep 16/60 Sephacryl S-300 HR column for samples collected from OptiMEM conditioned media and a 26/60 S-500 HR column for samples collected from pre-spun conditioned media (GE Healthcare), connected to an ÄKTA prime (GE healthcare) equipped with a UV flow cell. Each individual fraction was collected according to the UV absorbance. The collected fractions were then concentrated using a 30-kDa cut-off Amicon Ultra-15 spin filter (Millipore) to 300-400 µl and stored in −80° C. until further analyses.

Liquid Chromatography Fraction of UF Samples (UF-LC) from Placental Perfusions 1 ml of the UF STBM sample was loaded onto an XK16/70 Sephacryl S-1000 column (GE Healthcare), connected to fraction collector (RediFrac, Pharmacia). A pump speed of 2 ml/min was used and 4 ml fractions were collected. The collected fractions were then concentrated on a 30-kDa spin filter (Vivaspin, Sartorius Stedim), diluted to 300-400 µl and stored in −80° C. until further analysis.

Western Blotting

Western blotting was performed using either the Bio-Rad® Mini-PROTEAN® Tetra cell or the iBlot® system (Invitrogen, Life Technologies) according to the manufacturer's instructions. To cross-compare the yield of exosomes, we proceeded to load equal volumes of the re-suspended exosome pellet or filtrate on the gel.

For the Bio-Rad system, 15 µl of exosome samples with 15 µl of 2× Laemlli sample buffer (Bio-Rad) containing 5% β-mercaptoethanol were mixed and heated at 100° C. for 10 min. Samples were then loaded in a 1.5 mm, 10% Tris/Glycine SDS-polyacrylamide gel and ran at 170 V for 60-70 min in running buffer, until the dye front reached the bottom of the tank. Proteins on the gel were then transferred to a polyvinylidine fluoride (PVDF) membrane (Millipore) at 100 V for 60-70 min in transfer buffer containing 20% methanol. Membranes were then incubated in blocking buffer (5% fat-free milk in Tris buffer saline with 0.1% Tween-20 (TBS-T) for 60 min at room temperature (RT) with gentle shaking.

For the iBlot® system, 30 µl of sample was mixed with a sample buffer, containing 0.5 M dithiothreitol (DTT), 0.4 M sodium carbonate ($Na_2CO_3$), 8% SDS and 10% glycerol, and heated at 65° C. for 5 min. Samples were then loaded in a NuPAGE® Novex® 4-12% Bis-Tris Gel and ran at 120 V in running buffer until the dye front reached the bottom of the gel. The proteins on the gel were transferred to an iBlot nitrocellulose membrane (Invitrogen) for 7 min with the iBlot system. Membranes were stained with Ponceau S dye that was later washed away with PBS before blocking with Odyssey blocking buffer for 60 min at RT with gentle shaking.

After the blocking step, the membrane was incubated with freshly prepared primary antibody solution (anti-CD9, anti-PDC6I (Alix), anti-Tsg101 and anti-calnexin; all at 1:1,000 dilution from Abcam, Cambridge UK) overnight at 4° C. or 2 h at RT. Membranes were washed three times, 10 min each using washing buffer (TBS-T) with vigorous shaking before adding the secondary antibody solution (anti-mouse IgG DyLight-800 at 1:10,000 dilution if detecting Alix; anti-rabbit IgG DyLight-800 at 1:10,000 dilution for detecting CD9, Tsg101 and Calnexin) and incubated for 1 h at RT. After the secondary antibody incubation, membranes were washed three times, 10 min each and visualised by scanning both 700- and 800-nm channels on the LI-COR Odyssey CLx infrared imaging system. For subsequent probing of other proteins on the same membrane, the membrane was washed three times, 10 min each before re-incubation with the next primary antibody.

Nanoparticle Tracking Analysis

For particle size determination, nanoparticle tracking analysis (NTA) was performed with a NanoSight NS500 instrument equipped with the NTA 2.3 analytical software. For all our recordings, we used a camera level of 13 or 15 and automatic function for all post-acquisition settings: blur and minimum expected particle size, except in the detection threshold where we fixed it at 5. Samples were thawed on ice and diluted in PBS between 1:500 to 1:20,000 to achieve a particle count of between $2\times10^8$ and $2\times10^9$ per mL. Once the dilution of the sample was determined, sample was loaded in the sample chamber and the camera focus was adjusted to make the particles appear as sharp dots of light. Using the script control function, we recorded five 30 or 60 s videos for each sample; incorporating a sample advance and 5 s delay between each recording. For GFP positive exosomes the same set up was used with one minor alteration, which was that the sample was under constant flow in the sample chamber not to bleach the GFP signal. These measurements were then analysed using the batch process function and results were exported to Microsoft Excel for further analysis.

Quantification of Proteins and RNA in Exosomes

Protein quantities in exosomes were quantified using the microBCA assay kit (Thermo Scientific) and levels of RNA were measured using the Quant-iT™ RiboGreen® RNA assay kit (Life Technologies), according to the manufacturer's instructions.

Electron Microscopy

5 µl of exosome suspension was diluted 1:1 with PBS and added on formvar-carbon coated electron microscopy grids for 20 min. The grid was blotted with filter paper and 15 µl of 2% uranyl acetate (UA) was added on the grid for 1 min. Next, UA was removed and 15 µl of distilled water was added for 1 min. The water droplet was then removed and the grid was left to air dry for 15 min. The grids were then visualized in the electron microscope.

Fluorescence Microscopy

CD63-EGFP positive exosomes were generated as described above. The particles were quantified by NTA and the UF-LC and UC samples were diluted to the same concentration of particles/ml. Before any measurements the exosomes were re-suspended with a 27 G needle. The samples were positioned on a microscope slide and covered with a coverslip and analysed Microscopy was performed using Olympus IX-81 inverted microscope (Olympus America, Center Valley Pa., USA) equipped with 20× objective. The following fluorescence filter-set (Chroma Technology Corp., Bellows Falls, Vt., USA) was used, with the central wavelength and bandwidth of the excitation and emission filters as indicated: GFP (Ex. 470/40 nm; Em. 525/50 nm)

Liquid Chromatography Tandem Mass Spectrometry (LC-MS/MS) of Exosomes

Exosomes from UC and UF-LC were concentrated by speedvac and lysed with 1% SDS, 25 mM HEPES, 1 mM DTT. Lysates were heated to 95° C. for 5 min followed by sonication for 1 min and centrifugation at 14,000 g for 15 min. The supernatant was mixed with 1 mM DTT, 8 M urea, 25 mM HEPES, pH 7.6 and transferred to a 10-kDa cut-off centrifugation filtering unit (Pall, Nanosep®), and centrifuged at 14,000 g for 15 min, followed by an addition of the 8 M urea buffer and centrifugation again. Proteins were alkylated by 50 mM iodoacetamide (IAA) in 8 M urea, 25 mM HEPES for 10 min, The proteins were then centrifuged at 14,000 g for 15 min followed by 2 more additions and centrifugations with 8 M urea, 25 mM HEPES. Trypsin (Promega) in 250 mM urea, 50 mM HEPES was added to the cell lysate at a ratio of 1:50 trypsin:protein and incubated overnight at 37° C. The filter units were centrifuged at 14,000 g for 15 min followed by another centrifugation with MQ and the flow-through was collected. Peptides were cleaned by a strata-X-C-cartridge (Phenomenex).

Before analysis on the Q Exactive (Thermo Fischer Scientific, San Jose, Calif., USA), peptides were separated using an Agilent 1200 nano-LC system. Samples were trapped on a Zorbax 300SB-C18, and separated on a NTCC-360/100-5-153 (Nikkyo Technos., Ltd) column using a gradient of A (3% ACN, 0.1% FA) and B (95% ACN, 0.1% FA), ranging from 7% to 40% B in 240 min with a flow of 0.4 µl/min. The Q Exactive was operated in a data dependent manner, selecting top 5 precursors for fragmentation by HCD. The survey scan was performed at 70,000 resolution from 300-1700 m/z, using lock mass at m/z 445.120025, with a max injection time of 100 ms and target of $1\times10^6$ ions. For generation of HCD fragmentation spectra, a max ion injection time of 500 ms and AGC of $1\times10^5$ were used before fragmentation at 30% normalized collision energy, 17,500 resolution. Precursors were isolated with a width of 2 m/z and put on the exclusion list for 70 s. Single and unassigned charge states were rejected from precursor selection.

Proteome discoverer 1.3 with sequest-percolator was used for protein identification. Precursor mass tolerance was set to 10 ppm and for fragments to 0.02 Da. Oxidized methionine and was set as dynamic modification, and carbamidomethylation as static modification. Spectra were matched to a combined *Mus musculus* and *Bos taurus* ensembl 72 database, and results were filtered to 1% FDR. Identifications in *Bos taurus* was considered to originate from FBS and removed. GO term enrichment analysis was done using Panther.

Exosome Biodistribution in Mice

Conditioned cell supernatants were filtered through a 0.22 μm syringe filter and incubated with 1 μM DiR (1,1'-Dioctadecyl-3,3,3',3'-Tetramethylindotricarbocyanine Iodide) (Invitrogen). The conditioned media with DiR was then ultracentrifuged at 110,000 g for 70 min or concentrated with a 100 kDa Amicon Ultra spin filter (Millipore). The UC pellet was re-suspended and spun again in PBS to purify away-unbound DiR or LC fractionated as described above. The purified exosomes were quantified with NTA and equal amounts of particles from both UC and LC preparations were injected in the tail vein of Balb/c mice (n=5). 24 h post injection, the organs were harvested and subjected to imaging in the In Vivo Imaging System (IVIS) Spectrum (Caliper). The IVIS was set to record the fluorescence for 2 seconds (excitation 710, emission 760) and the data obtained was then analysed with the IVIS software. All animal experiments were approved by The Swedish Local Board for Laboratory Animals. The experiments were performed in accordance with the ethical permission and designed to minimize the suffering and pain of the animals.

Colitis Treatment Using Exosomes Displaying Signalling-Incompetent CD63-sTNFR1

The well-studied TNBS-induced colitis model in mice was used, simulating the cytokine storm, the diarrhea, weight decrease, and gut inflammation seen in IBD patients. 24 mice were divided into four treatment groups, with 6 mice per group. The mice were pre-sensitized by applying 150 μl of a olive oil-acetate solution with 2% TNBS, on the skin, 1 week prior to colitis induction. Colitis was then induced by giving a rectal infusion of 100 μl solution containing 1.5% TNBS in 40% ethanol. Immediately post colitis induction, 30 μg exosomes in 200 μl were administrated intravenously in the tail vein. The mice were given either decoy signalling-incompetent TNFR1-CD63 exosomes, unmodified exosomes, signalling-competent TNFR1-CD63 exosomes, or PBS as mock treatment, depending on the assigned treatment group. The bodyweight was recorded daily.

Figure 2:
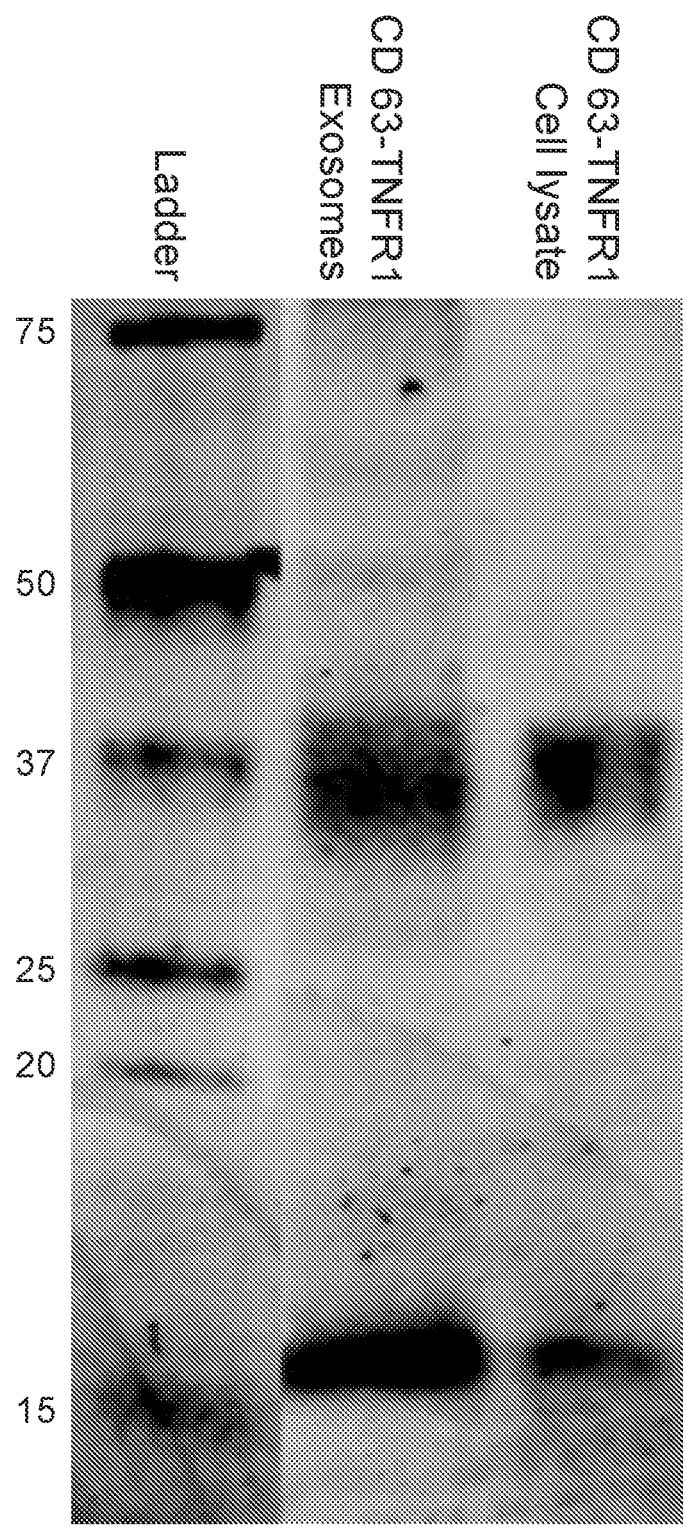
FIG. 2 shows Western blot confirmation of the presence, on the exosomal surface, of the CD63-sTNFR1 polypeptide used for the colitis treatment of FIG. 1.
Figure 3:
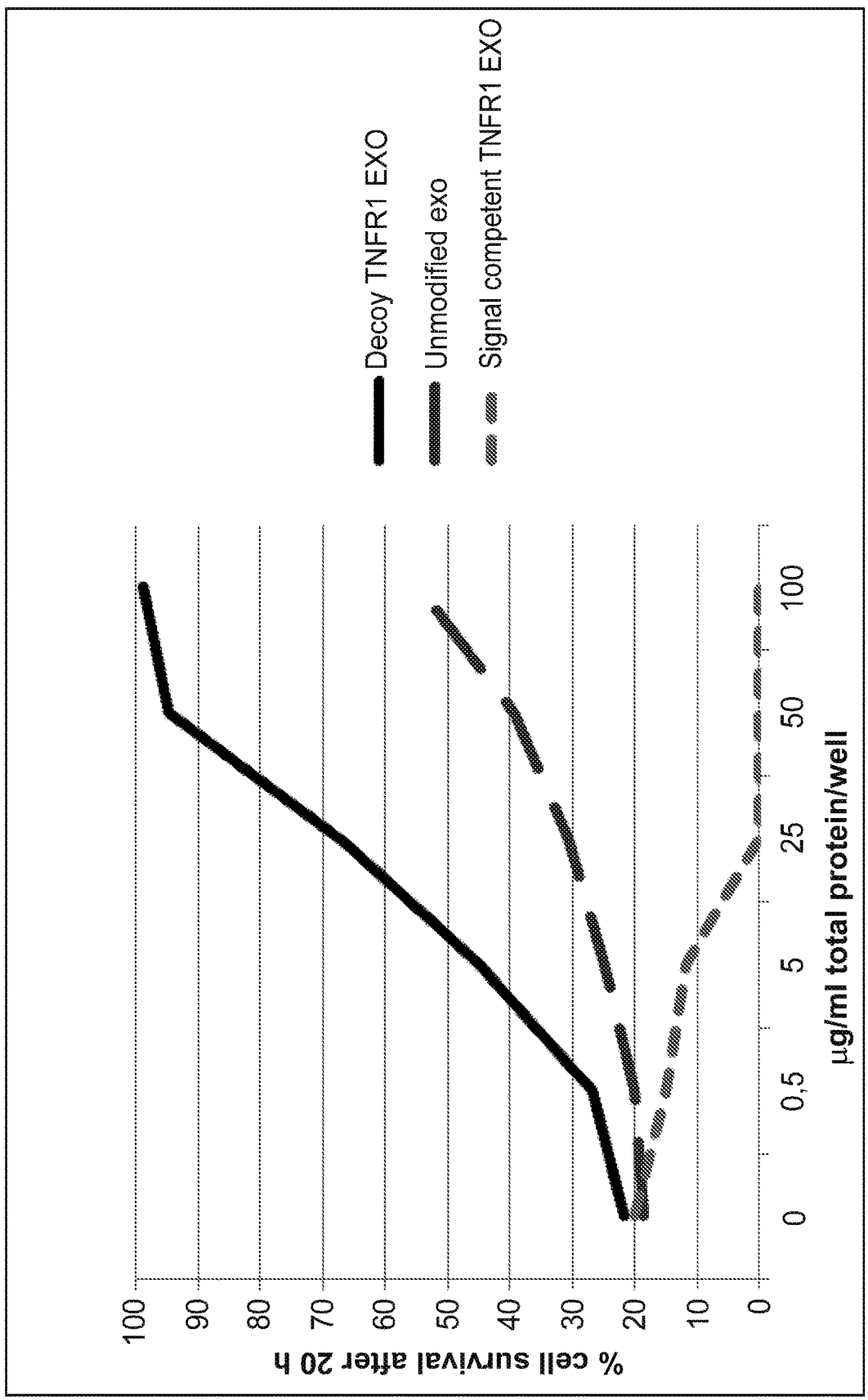
FIG. 3 shows the neutralizing activity of the sTNFR1 decoy exosomes of FIG. 1 on TNFα-mediated cytotoxicity. The exosomes displaying signalling-incompetent sTNFR1-CD63 exhibit good TNFα neutralization in a dose-dependent manner (solid black line), and the signalling-competent sTNFR1-CD63-containing exosomes are, as in FIG. 1, aggravating the response (short-dashed grey line). Unmodified exosomes (long-dashed grey line) also show a moderate effect due to their anti-inflammatory properties.

As can be seen from FIG. 2, administration of exosomes comprising decoy receptor as per the present invention leads to successful treatment of colitis in mice. The signalling-incompetent decoy exosomes successfully treat induced colitis within a few days with less loss in body weight, whereas unmodified exosomes show a moderate effect. Signalling-competent decoy receptors in fact aggravate the condition.

Western Blot of CD63-sTNFR1 on the Exosomal Surface

Western Blot was carried out towards the extracellular part of TNFR1, to verify the presence of the CD63-sTNFR1 polypeptide construct on the exosomal surface. Predicted molecular weight for the CD63-TNFR1 construct is 38.52 kDa, which can be seen in the vicinity of the 37 kDa reference band, both in the cell lysate sample and the exosome sample. The fusion protein is loaded onto the exosomes with great efficiency, since the band is so strong in the exosome fraction (the band around 15 kDa is an irrelevant unspecific band).

Neutralization of TNFα-Mediated Toxicity

The neutralizing activity of signalling-incompetent CD63-TNFR1 exosomes, signalling-competent CD63-TNFR1 exosomes and exosomes from N2a cells against human TNF-α was measured on the mouse WEHI 164 cell line treated with actinomycin D as previously described (Austgulen et al., 1986; Khabar et al., 1995), in order to verify the binding affinity for TNFα. Briefly, WHEI 164 cells were seeded in triplicate at $1\times10^4$ cells/well in a 96-well plate and cultured in RPMI 1640 medium supplemented with 10% (v/v) FBS for 20 h. Subsequently, serially diluted exosomes (final concentration: 0.5-100 ug/ml) in the medium containing 2 μg/ml actinomycin D were added to the cell culture together with 0.1 ng/ml of human TNF-α. The cells were incubated for an additional 20 h at a temperature of 37 degrees Centigrade and cell viability was analyzed using a colorimetric MTT-based Cell Growth Determination kit (Sigma, St. Louis, Mo.). The $ED_{50}$ value was calculated by complex sigmoid non-linear regression analysis using Sigma plot software (Systat software, Inc. Richmond, Calif.).

Anti-Tumour Efficacy of Exosomes and Liposomes Displaying Signalling-Incompetent Syndecan/CD63-sVEGFR1

30 mice were implanted with $1\times10^6$ B16/F10 melanoma cells into the flank at day zero. The mice were then divided into five treatment groups, with 6 mice per group. After one week (day 7), the mice received intravenous injections of 30 μg exosomes in 200 μl which were repeated every second days for two weeks. The mice were given exosomes comprising signalling-incompetent syndecan-sVEGFR1, signalling-incompetent CD63-sVEGFR1 exosomes, unmodified exosomes, and exosomes comprising signalling-competent CD63-sVEGFR1, or PBS as mock treatment depending on assigned treatment group. The tumour volume was measured every second day.

Figure 4:
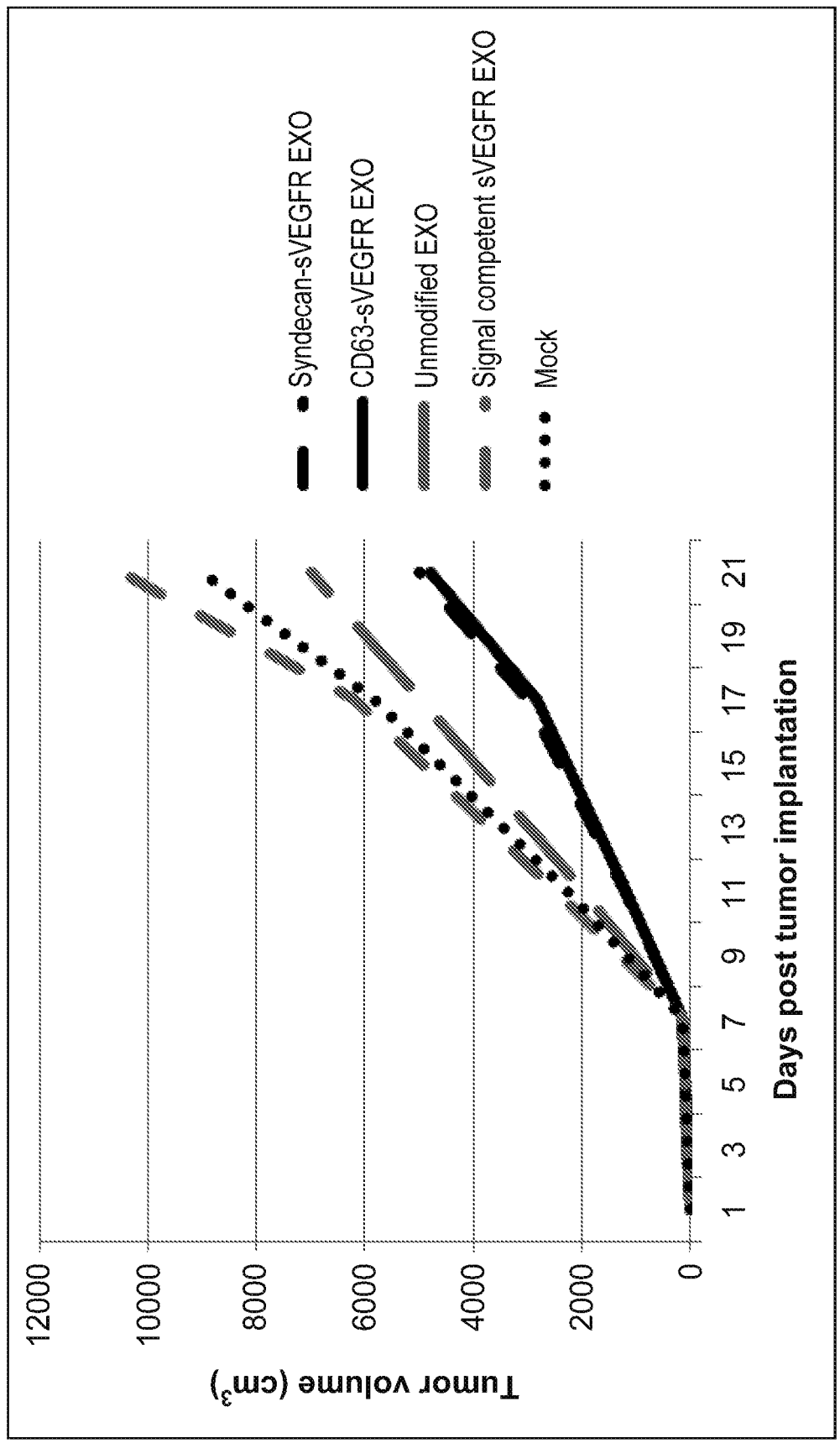
FIG. 4 shows a graph over the tumour inhibitory effects of exosomes displaying either signalling-incompetent soluble vascular endothelial growth factor receptor (sVEGFR) (SEQ ID No 17) fused to CD63 (solid black line) or signalling-incompetent sVEGFR fused to syndecan (SEQ ID NO 23-26) (dashed black line). Mice treated with exosomes comprising the above polypeptide constructs had a considerably reduced tumour burden post treatment, whereas treatment with exosomes comprising signalling-competent sVEGFR polypeptide did again display a worsened outcome compared to control (short-dashed grey line).

The arrow in FIG. 4 indicates start of treatment (day 7). The mice treated with signalling-incompetent decoy sVEGFR1 exosomes (syndecan-sVEGFR1 EXO and CD63-sVEGFR1 EXO) displayed the lowest tumour burden after treatment.

Treatment with unmodified exosomes had a moderate effect on tumour size, whereas treatment with exosomes comprising signalling-competent CD63-sVEGFR1 resulted in an aggravated condition, compared to the mock-treated control group.

The above experiments were also repeated with liposomes comprising the same set of polypeptide decoy receptors and similar results were obtained.

Treatment of MDX Mice

N2a cells were seeded at 3 million per 150 cm² flask and grown in DMEM with 10% FBS. After 24 hours the cells were PEI-transfected with plasmids encoding signalling-incompetent activin-syndecan or signalling-incompetent activin-synaptotagmin. 4 hours post transfection the media was changed to OptiMEM. 72 hours after the media change exosomes produced by the N2a cells were harvested by ultra-filtration and sequential LC purification. The exosomes were used immediately or stored at −20. MDX mice were obtained from Charles River at a weight of around 18-19 grams. The mice were allocated into 4 groups with 6 mice in each group. The mice received injections of exosomes or PBS twice weekly for 12 weeks. The weight was recorded before each injection.

Figure 5:
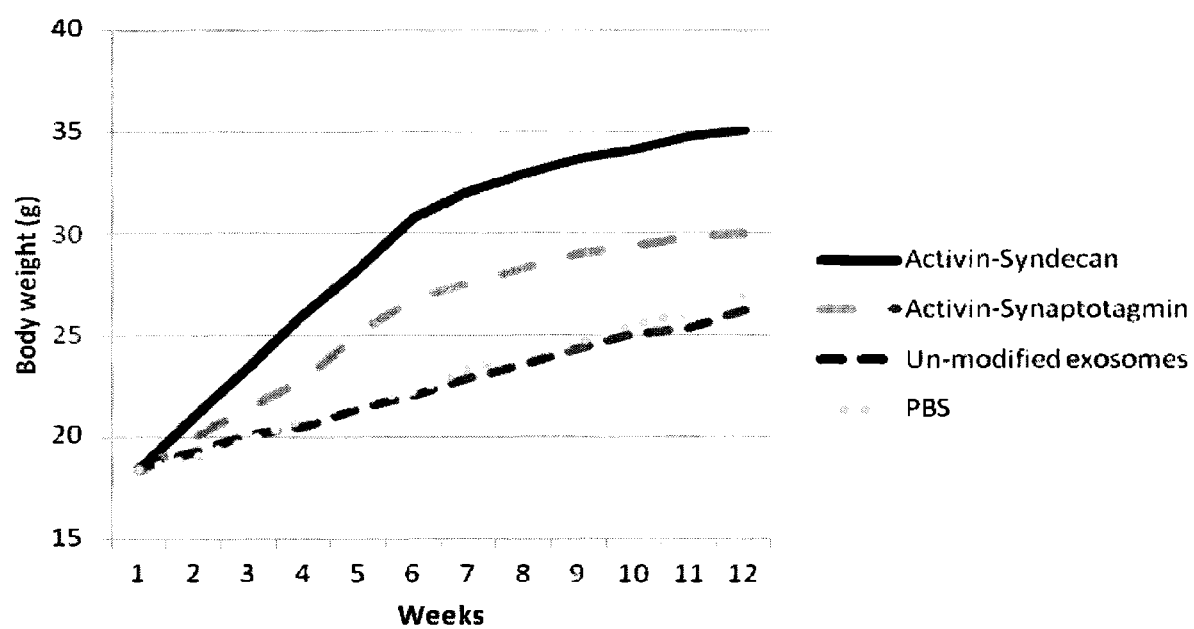
FIG. 5 shows treatment efficacy in MDX mice of exosomes comprising the therapeutic decoy polypeptide receptor activin (SEQ ID No 40-43) fused to either the carrier proteins syndecan (solid black line) or synaptotagmin (SEQ ID No 27) (long-dashed grey line). Bi-weekly treatment with the above therapeutic delivery exosomes resulted in a considerably greater body weight increase than treatment with unmodified exosomes and mock treatment.
Figure 7:
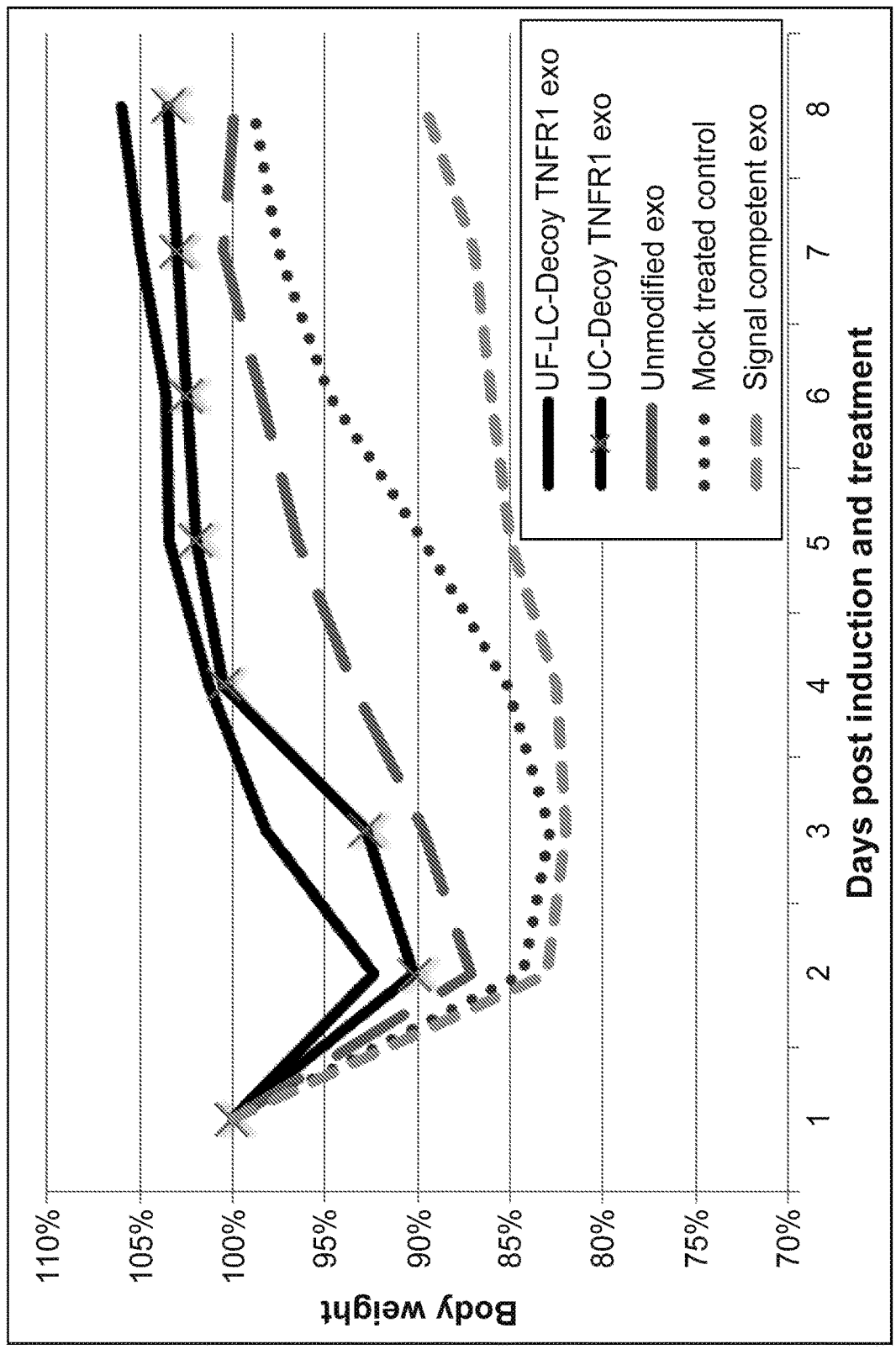
FIG. 7 illustrates the increased therapeutic efficacy seen when using exosomes (comprising a therapeutic polypeptide comprising soluble tumour necrosis factor receptor 1 (sTNFR1) fused to the carrier polypeptide CD63) obtained via ultrafiltration-liquid chromatography (UF-LC) purification (solid black line), compared to the same exosomes obtained via a conventional ultracentrifugation (UC) process (crossed solid black line). The increased therapeutic efficacy is most likely due to the improved biophysical stability of the exosomes obtained via UF-LC, which in turn results in less accumulation in lung tissue.

FIG. 5 shows treatment efficacy in MDX mice of exosomes comprising the therapeutic decoy polypeptide receptor activin fused to either the carrier proteins syndecan (solid black line) or synaptotagmin (long-dashed grey line). Bi-weekly treatment with the above therapeutic delivery exosomes resulted in a considerably greater body weight increase than treatment with unmodified exosomes and mock treatment.

The above experiments were also repeated with chylomicrons and similar results were obtained.

Treatment of Neuro-Inflammation

In an in vivo model of experimental autoimmune encephalomyelitis (EAE), mice treated with decoy exosomes (as described above) displayed a markedly improved disease phenotype, fig X3. EAE was induced by immunization of mice with neuroantigen (myelin basic protein, MBP) and complete Freund's adjuvant (containing *M. tuberculosis*), followed by injection of pertussis toxin to produce severe and reliable EAE. Disease progression with clinical symptoms was recorded daily from disease onset (day 12-28). The symptoms are scored based on severity (0=normal mouse; no overt signs of disease; 1=limptail or hind limb weakness, but not both; 2=limptail and hind limb weakness; 3=partial hind limb paralysis; 4=complete hind limb paralysis; 5=moribund state; death by EAE: sacrifice for humane reasons), resulting in a mean clinical score used to assess disease state. Notable is that mice, with and without induced EAE, treated with exosomes derived from neural origin resulted in spasms and subsequent death, compared to treatment of exosomes from other cell origins where this phenomenon was not present. FIG. 9 illustrates the efficacy of the following delivery exosomes:

Decoy exosomes comprising IL6R+TNFR1
Decoy exosomes comprising IL6R
Decoy exosomes comprising TNFR1
Decoy exosomes comprising IL-1βR
Unmodified exosomes
Untreated control As can be seen from FIG. 9, EAE-mice treated with decoy exosomes displaying signalling-incompetent receptors for IL6, IL-1β and TNFα display a very moderate disease manifestation compared to mock treated control, whereas mice treated with signalling-competent (TNFR1 signalling-competent) therapeutic polypeptide receptor-containing exosome display a worsened disease.

What is claimed is:

1. A method for purifying therapeutic delivery exosomes, comprising:
   (i) introducing at least one polynucleotide construct encoding at least one polypeptide into a cell line capable of producing therapeutic delivery exosomes;
   (ii) collecting the therapeutic delivery exosomes produced by the cell line of step (i); and
   (iii) purifying the therapeutic delivery exosomes collected in step (ii) using ultrafiltration followed by size exclusion liquid chromatography.

2. A method of claim 1, wherein at least one filter is used during ultrafiltration.

3. A method of claim 2, wherein the at least one filter comprises a molecular weight cut-off of 100 kDa.

4. A method of claim 2, wherein the at least one filter comprises a molecular weight cut-off of 200 kDa.

5. A method of claim 2, wherein the at least one filter comprises a molecular weight cut-off of 500 kDa.

6. A method of claim 1, wherein at least two different filters are used during ultrafiltration and wherein the at least two different filters have the same molecular weight cut-off.

7. A method of claim 1, wherein at least two different filters are used during ultrafiltration and wherein the at least two different filters have a different molecular weight cut-off.

8. A method of claim 1, wherein extracellular vesicles purified using ultrafiltration followed by size exclusion liquid chromatography comprise less protein contamination than extracellular vesicles purified using ultracentrifugation alone.

9. A method of claim 1, wherein the at least one polypeptide is a therapeutic polypeptide.

10. A method for purifying therapeutic delivery exosomes, comprising:
    (i) introducing at least one polynucleotide construct encoding at least one polypeptide into a cell line capable of producing therapeutic delivery exosomes and exposing the cell line to oxygen deprivation, serum starvation, or a combination thereof;
    (ii) collecting the therapeutic delivery exosomes produced by the cell line of step (i); and
    (iii) purifying the therapeutic delivery exosomes collected in step (ii) using ultrafiltration followed by size exclusion liquid chromatography.

11. A method of claim 10, wherein the at least one polypeptide is a therapeutic polypeptide.

12. A method for purifying therapeutic delivery exosomes, comprising:
    (i) introducing at least one polynucleotide construct encoding at least one polypeptide into a cell line capable of producing therapeutic delivery exosomes;
    (ii) and exposing the cell line to autophagy-inhibiting substances;
    (ii) collecting the therapeutic delivery exosomes produced by the cell line of step (i); and
    (iii) purifying the therapeutic delivery exosomes collected in step (ii) using ultrafiltration followed by size exclusion liquid chromatography.

13. A method of claim 12, wherein the at least one polypeptide is a therapeutic polypeptide.

* * * * *

UNITED STATES PATENT AND TRADEMARK OFFICE
CERTIFICATE OF CORRECTION

PATENT NO. : 11,649,272 B2
APPLICATION NO. : 16/795429
DATED : May 16, 2023
INVENTOR(S) : Samir El Andaloussi et al.

Page 1 of 1

It is certified that error appears in the above-identified patent and that said Letters Patent is hereby corrected as shown below:

In the Claims

At Column 192, Claim number 12, Line number 30, replace:
"capable of producing therapeutic delivery exosomes;"
With:
--capable of producing therapeutic delivery exosomes--

At Column 192, Claim number 12, Line number 31, replace:
"(ii) and exposing the cell line to autophagy-inhibiting"
With:
--and exposing the cell line to autophagy-inhibiting--

Signed and Sealed this
Twenty-seventh Day of June, 2023

Katherine Kelly Vidal
*Director of the United States Patent and Trademark Office*